US005641663A

United States Patent [19]
Garvin et al.

[11] Patent Number: 5,641,663
[45] Date of Patent: *Jun. 24, 1997

[54] EXPRESSION SYSTEM FOR THE SECRETION OF BIOACTIVE HUMAN GRANULOCYTE MACROPHAGE COLONY STIMULATING FACTOR (GM-CSF) AND OTHER HETEROLOGOUS PROTEINS FROM STEPTOMYCES

[75] Inventors: Robert T. Garvin, Toronto; Lawrence T. Malek, Brampton, both of Canada

[73] Assignee: Cangene Corporation, Mississauga, Canada

[*] Notice: The term of this patent shall not extend beyond the expiration date of Pat. No. 5,200,327.

[21] Appl. No.: 318,193

[22] Filed: Oct. 5, 1994

Related U.S. Application Data

[63] Continuation of Ser. No. 935,314, Aug. 26, 1992, abandoned, which is a continuation-in-part of Ser. No. 844,937, Mar. 4, 1992, abandoned, which is a continuation of Ser. No. 221,346, Jul. 18, 1988, abandoned, and Ser. No. 224,568, Jul. 26, 1988, Pat. No. 5,200,327, each is a continuation-in-part of Ser. No.863,546, Apr. 6, 1992, abandoned, which is a continuation of Ser. No. 646,466, Jan. 25, 1991, abandoned, which is a continuation of Ser. No. 795,331, Nov. 6, 1985, abandoned.

[30] Foreign Application Priority Data

Jul. 27, 1987 [CA] Canada ................................ 542678
Jul. 25, 1988 [CA] Canada ................................ 572956

[51] Int. Cl.⁶ .................... C12N 15/67; C12N 15/09; C12N 15/63; C07H 21/04
[52] U.S. Cl. .................. 435/172.1; 435/69.1; 435/71.2; 435/252.35; 435/320.1; 536/23.1; 536/23.5; 536/24.1; 935/41; 935/48
[58] Field of Search ................ 435/320.1, 69.1, 435/71.2, 169, 172.1, 252.35, 886; 536/23.1, 23.5, 23.4, 24.1, 24.3, 23.7; 935/39, 41, 48

[56] References Cited

U.S. PATENT DOCUMENTS

| | | | |
|---|---|---|---|
| 4,745,056 | 5/1988 | Guteman et al. | 435/69.1 |
| 4,783,415 | 11/1988 | Hoshiko et al. | 435/320.1 |
| 5,200,327 | 4/1993 | Garvin | 435/69.5 |

OTHER PUBLICATIONS

*Bergey's Manual of Determinative Bacteriology*, Buchanan et al., eds., (The Williams & Wilkins Company, 1974) pp: 1231–1232.

(List continued on next page.)

*Primary Examiner*—Mindy Fleisher
*Assistant Examiner*—Nancy J. Degen
*Attorney, Agent, or Firm*—Foley & Lardner

[57] ABSTRACT

A gene expression system is used to produce heterologous biologically active proteins, in particular bioactive granulocyte macrophage colony stimulating factor ("GM-CSF"), secreted from a host selected from the Streptomyces genera. The gene expression system includes a regulatory nucleotide sequence linked to a second nucleotide sequence encoding the heterologous protein. The regulatory sequence, encodes a peptide which directs the secretion of the heterologous protein in bioactive form from a host selected from the Streptomyces genera. The regulatory sequence includes a signal sequence and a promoter sequence. The second nucleotide sequence, which encodes GM-CSF or a biologically active derivative of GM-CSF, may be either natural or synthetic. In particular, the invention relates to an expression system for secreting bioactive, non-glycosylated, oxidized, therapeutically useful GM-CSF from a host selected from the Streptomyces genera.

Also disclosed are similar constructs for expression of interleukin 3 (IL-3), interleukin 6 (IL-6), tumor necrosis factor alpha (TNFα), human stem cell factor (SCF), interleukin 7 (IL-7), erythropoietin (EPO) and interleukin 2 (IL-2). Novel signal peptides of these constructs include hybrids of the signal peptides of *Streptomyces griseus* protease B and *Escherichia coli* ompA, hybrids of *Streptomyces griseus* protease B and *Streptomyces limosus* α-amylase signal peptide.

9 Claims, 31 Drawing Sheets

OTHER PUBLICATIONS

Yang et al Cell 47 3–10 1986.

Otsuka et al. J Immunol 140 2288–2295 1988.

Hirano et al. Nature 324 73–76 1986.

Brakenhoff et al J Immunol 139 4116–4121 1987.

van Damme et al. J. Exp. Med. 165 914–919 1987.

Pennica et al Nature 312 724–729 1984.

Martin et al. Cell 63 203–211 1990.

Goodwin et al. PNAS 86 302–306 1989.

Jacobs et al Nature 313 806–809 1985.

Taniguchi et al Nature 302 305–310 1983.

Buttner et al Cell 52 599–607 1988.

Lathe J Mol Biol. 183 1–12 1985.

Henderson "Characterization and Structure of Genes for Proteases A and B from *Streptomyces griseus*", *J. Bacteriology*, 169: 3778–3784 (1987).

Bibb et al. "The Agarase Gene (dagA) of *Streptomyces coelicolor* A3(2): Affinity Purification . . . ". *J. Gen. Microbiol.* 133: 2089–2096 (1987).

Jurasek et al. "Amino Acid Sequence of *Streptomyces griseus* Protease B, A Major Component of Pronase", *Biochem. and Biophysical Research Communications*, 61(4): 1095–1100 (1974).

Duez et al. "Primary Structure of the *Streptomyces* R61 Extracellular DD–Peptidase . . . ", *Eur. J. Biochem.*, 162: 509–518 (1987).

Burgess et al. "Purification and Properties of Bacterially Synthesized Human Granulocyte–Macrophage Colony Stimulating Factor", *Blood*, 58: 43–51 1987.

Chang, "Engineering for Protein Secretion in Gram–Positive Bacteria", *Methods in Enzymology*, 153: 507–517 (1987).

Ernst et al. "O–Glycosylation and Novel Processing Events During Secretion Of α–Factor/GM–CSF Fusions By *Saccharomyces cerevisiae*", *Biotechnology*, 5: 831–834 (1987).

Lee et al. "Isolation Of cDNA For A Human Granulocyte–Macrophage Colony–Stimulating Factor By Functional Expression In Mammalian Cells", *Proc. Natl. Acad. Sci. USA*, 82: 4360–4364 (1985).

Moonen et al. "Increased Biological Activity of Deglycosylated Recombinant Human Granulocyte/Macrophage Colony–Simulating . . . ", *Proc. Natl. Acad. Sci. USA*, 84: 4428–4431 (1987).

Robbins et al. "Primary Structure of the *Streptomyces* Enzyme Endo–β–N–Acetylglucosaminidase H", *J. Biol. Chem.*, 259: 7577–7583 (1984).

Sjostrom et al. "Signal Peptide Amino Acid Sequences In *Escherichia coli* Contain Information Related to Final Protein Localization . . . ", *EMBO J.*, 6(3): 823–831 (1987).

Wong et al. "Human GM–CSF: Molecular Cloning Of The Complementary DNA And Purification Of The Natural And Recombinant Proteins", *Science* 228: 810–814 (1985).

Bender et al., "Secretory Synthesis of Human Interleukin–2 by *Streptomyces lividans*," *Gene* 86:227–232 (1990).

Chang et al., "Secretion of Heterologous Proteins in *Streptomyces lividans*," Biology of Actinomycetes Okami et al. (ed.), Japan Scientific Societies Press 103–107 (1988).

```
          PstI                    SalI
        GCCCCCGCCGGTCGCCCTCGCCGTCGACCCAGCCGTGGGAGCACGTCAACGCGAT
        ----.----+----.----+----.----+----.----+----.----+----.----+   60
        ACGTCGGGGCGGGCCAGCGGGAGCGGCAGCTGGGTCGGCACCCTCGTGCAGTTGCGCTA

CCAGGAGGCCCGCCGCCTGGTCAACCTCTCGCGGGACACGGCCGCCGAGATGAACGAGAC
        ----.----+----.----+----.----+----.----+----.----+----.----+   120
        GGTCCTCCGGGCGGCGGACGAGTTGGAGAGCGCCCTGTGCCGGCGGCTCTACTTGCTCTG

CGTGGAGGTGATCTCGGAGATGTTCGACTTGCAGGAGCCCACGTGCCTCCAGACCCGCCT
        ----.----+----.----+----.----+----.----+----.----+----.----+   180
        GCACCTCCACTAGAGCCTCTACAAGCTGAACGTCCTCGGGTGCACGGAGGTCTGGGCGGA

CGAGCTGTACAAGCAGGGGCTCCGGGGCAGCCTCACCAAGCTCAAGGGGCCGCTGACCAT
        ----.----+----.----+----.----+----.----+----.----+----.----+   240
        GCTCGACATGTTCGTCCCCGAGGCCCCGTCGGAGTGGTTCGAGTTCCCCGGCGACTGGTA

GATGGCGTCCCACTACAAACAGCACTGCCCCCCCACGCCGGAGACGTCGTGCGCCACCCA
        ----.----+----.----+----.----+----.----+----.----+----.----+   300
        CTACCGCAGGGTGATGTTTGTCGTGACGGGGGGGTGCGGCCTCTGCAGCACGCGGTGGGT

GATCATCACGTTCGAGTCGTTCAAGGAGAACCTGAAGGACTTCCTCCTCGTGATCCCCTT
        ----.----+----.----+----.----+----.----+----.----+----.----+   360
        CTAGTAGTGCAAGCTCAGCAAGTTCCTCTTGGACTTCCTGAAGGAGGAGCACTAGGGGAA
                                              HindIII
        CGACTGCTGGGAGCCGGTGCAGGAGTGA
        ----.----+----.----+----.----+--   392
        GCTGACGACCCTCGGCCACGTCCTCACTTCGA
```

BamHI
```
GATCCGGCCGTTTCCCGCGCCGCCCGCGCCCACGTGGCGCGGTGGGGGATTCCGGCCGAA
----.----+----.----+----.----+----.----+----.----+----.----+  60
GCCGGCAAAGGGCGCGGCGGGCGCGGGTGCACCGCGCCACCCCCTAAGGCCGGCTT

CGCGCCGACGCCCATGTGACCGCCTGCGTGCTGCGCGGCGCCCGCGCCGCAGGCTCGCCG
----.----+----.----+----.----+----.----+----.----+----.----+  120
GCGCGGCTGCGGGTACACTGGCGGACGCACGACGCGCCGCGGGCGCGGCGTCCGAGCGGC

GGGCGGACCCGGACCCGGCCGCCGAGGTCCTCGCCGCCGACCGGGAGGCGTGCGGCCTCG
----.----+----.----+----.----+----.----+----.----+----.----+  180
CCCGCCTGGGCCTGGGCCGGCGGCTCCAGGAGCGGCGGCTGGCCCTCCGCACGCCGGAGC

.CCGCGAGACCGCCGTCCTGCTGCGGCTCACGGAGGCGTACCTCTCGCCCTGCGCGCGGGC
----.----+----.----+----.----+----.----+----.----+----.----+  240
GGCGCTCTGGCGGCAGGACGACGCCGAGTGCCTCCGCATGGAGAGCGGGACGCGCGCCCG

CCTCGACCCCGCCGGGACCTCCGGCACCGGGCCCGCGGGCGACGCCGGGCGCACCGGGTC
----.----+----.----+----.----+----.----+----.----+----.----+  300
GGAGCTGGGGCGGCCCTGGAGGCCGTGGCCCGGGCGCCCGCTGCGGCCCGCGTGGCCCAG

CGCCGGCGCCCCCCACCCCGCACAAGAATGTCCGAAACCCTACGGGCCCCGACGAAAGG
----.----+----.----+----.----+----.----+----.----+----.----+  360
GCGGCCGCGGGGGGGTGGGGCGTGTTCTTACAGGCTTTGGGATGCCCGGGGCTGCTTTCC

CGCGGAACGGCGTCTCCGCCTCTGCCATGATGCCGCCCATGAGGATCAAGCGCACCAGCA
----.----+----.----+----.----+----.----+----.----+----.----+  420
GCGCCTTGCCGCAGAGGCGGAGACGGTACTACGGCGGGTACTCCTAGTTCGCGTGGTCGT

MluI
ACCGCTCGAACGCGGCGAGACGCGTCCGCACCACCGCCGTACTCGCGGGGCTCGCCGCCG
----.----+----.----+----.----+----.----+----.----+----.----+  480
TGGCGAGCTTGCGCCGCTCTGCGCAGGCGTGGTGGCGGCATGAGCGCCCCGAGCGGCGGC

TCGCGGCGCTGGCCGTTCCCACCGCCAATGCAGCCCCCGCCCGGTCGCCCTCGCCGTCGA
----.----+----.----+----.----+----.----+----.----+----.----+  540
AGCGCCGCGACCGGCAAGGGTGGCGGTTACGTCGGGGGCGGGCCAGCGGGAGCGGCAGCT

CCCAGCCGTGGGAGCACGTCAACGCGATCCAGGAGGCCCGCCGCCTGCTCAACCTCTCGC
----.----+----.----+----.----+----.----+----.----+----.----+  600
GGGTCGGCACCCTCGTGCAGTTGCGCTAGGTCCTCCGGGCGGCGGACGAGTTGGAGAGCG

GGGACACGGCCGCCGAGATGAACGAGACCGTGGAGGTGATCTCGGAGATGTTCGACTTGC
----.----+----.----+----.----+----.----+----.----+----.----+  660
CCCTGTGCCGGCGGCTCTACTTGCTCTGGCACCTCCACTAGAGCCTCTACAAGCTGAACG
```

FIG.3b'

```
AGGAGCCCACGTGCCTCCAGACCCGCCTCGAGCTGTACAAGCAGGGGCTCCGGGGCAGCC
||||.|||||||||||||||||||||||||||||||||||||||||||||||||||||||    720
TCCTCGGGTGCACGGAGGTCTGGGCGGAGCTCGACATGTTCGTCCCCGAGGCCCCGTCGG

TCACCAAGCTCAAGGGGCCGCTGACCATGATGGCGTCCCACTACAAACAGCACTGCCCCC
||||||||||||||||||||||||||||||||||||||||||||||||||||||||||||    780
AGTGGTTCGAGTTCCCCGGCGACTGGTACTACCGCAGGGTGATGTTTGTCGTGACGGGGG

CCACGCCGGGAGACGTCGTGCGCCACCCAGATCATCATCACGTTCGAGTCGTTCAAGGAGAACC
||||||||||||||||||||||||||||||||||||||||||||||||||||||||||||    840
GGTGCGGGCCCTCTGCAGCACGCGGTGGGTCTAGTAGTGCAAGCTCAGCAAGTTCCTCTTGG

HindIII
TGAAGGACTTCCTCCTCGTCGTGATCCCCTTCGACTGCTGGGAGCCGGTGCAGGAGTGA
||||||||||||||||||||||||||||||||||||||||||||||||||||||||||||    900
ACTTCCTGAAGGAGGAGCACTAGGGGAAGCTGACGACCCTCGGCCACGTCCTCACTTCGA
```

FIG. 4b

BamHI
```
GATCCGGCCGTTTCCCGCGCCGCCCGCGCCCACGTGGCGCGGTGGGGGATTCCGGCCGAA
----.----+----.----+----.----+----.----+----.----+----.----+   60
    GCCGGCAAAGGGCGCGGCGGGCGCGGGTGCACCGCGCCACCCCCTAAGGCCGGCTT

CGCGCCGACGCCCATGTGACCGCCTGCGTGCTGCGCGGCGCCCGCGCCGCAGGCTCGCCG
----.----+----.----+----.----+----.----+----.----+----.----+  120
GCGCGGCTGCGGGTACACTGGCGGACGCACGACGCGCCGCGGGCGCGGCGTCCGAGCGGC

GGGCGGACCCGGACCCGGCCGCCGAGGTCCTCGCCGCCGACCGGGAGGCGTGCGGCCTCG
----.----+----.----+----.----+----.----+----.----+----.----+  180
CCCGCCTGGGCCTGGGCCGGCGGCTCCAGGAGCGGCGGCTGGCCCTCCGCACGCCGGAGC

CCGCGAGACCGCCGTCCTGCTGCGGCTCACGGAGGCGTACCTCTCGCCCTGCGCGCGGGC
----.----+----.----+----.----+----.----+----.----+----.----+  240
GGCGCTCTGGCGGCAGGACGACGCCGAGTGCCTCCGCATGGAGAGCGGGACGCGCGCCCG

CCTCGACCCCGCCGGGACCTCCGGCACCGGGCCCGCGGGCGACGCCGGGCGCACCGGGTC
----.----+----.----+----.----+----.----+----.----+----.----+  300
GGAGCTGGGGCGGCCCTGGAGGCCGTGGCCCGGGCGCCCGCTGCGGCCCGCGTGGCCCAG

CGCCGGCGCCCCCCACCCCGCACAAGAATGTCCGAAACCCTACGGGCCCCGACGAAAGG
----.----+----.----+----.----+----.----+----.----+----.----+  360
GCGGCCGCGGGGGGGTGGGGCGTGTTCTTACAGGCTTTGGGATGCCCGGGGCTGCTTTCC

CGCGGAACGGCGTCTCCGCCTCTGCCATGATGCCGCCCATGAGGATCAAGCGCACCAGCA
----.----+----.----+----.----+----.----+----.----+----.----+  420
GCGCCTTGCCGCAGAGGCGGAGACGGTACTACGGCGGGTACTCCTAGTTCGCGTGGTCGT

MluI
ACCGCTCGAACGCGGCGAGACGCGTCCGCACCGCGGCCCTGGCCCTCTCCGCTGCCGCCG
----.----+----.----+----.----+----.----+----.----+----.----+  480
TGGCGAGCTTGCGCCGCTCTGCGCAGGCGTGGCGCCGGGACCGGGAGAGGCGACGGCGGC

PstI
CGCTCGTGCTGGGGTCGACGGCCGCCTCCGGGGCGTCTGCAGCCCCCGCCCGGTCGCCCT
----.----+----.----+----.----+----.----+----.----+----.----+  540
GCGAGCACGACCCCAGCTGCCGGCGGAGGCCCCGCAGACGTCGGGGCGGGCCAGCGGGA

CGCCGTCGACCCAGCCGTGGGAGCACGTCAACGCGATCCAGGAGGCCCGCCGCCTGCTCA
----.----+----.----+----.----+----.----+----.----+----.----+  600
GCGGCAGCTGGGTCGGCACCCTCGTGCAGTTGCGCTAGGTCCTCCGGGCGGCGGACGAGT

ACCTCTCGCGGGACACGGCCGCCGAGATGAACGAGACCGTGGAGGTGATCTCGGAGATGT
----.----+----.----+----.----+----.----+----.----+----.----+  660
TGGAGAGCGCCCTGTGCCGGCGGCTCTACTTGCTCTGGCACCTCCACTAGAGCCTCTACA
```

FIG. 4b'

```
TCGACTTGCAGGAGAGCCCACGTGCCTTCCAGACCCGGCCTCGAGCTGTACAAGCAGGGGCTCC
||||.||||+||||.|||||+||||.||||+||||.||||+||||.||||+||||.||||           720
AGCTGAACGTCCTCGGGTGCACGGAGGTCTGGGCCGGAGCTCGACATGTTCGTCCCCGAGG

GGGGCAGCCTCACCAAGCTCAAGGGGCCGCTGACCATGATGGCGTCCCACTACAAACAGC
||||.||||+||||.||||+||||.||||+||||.||||+||||.||||+||||.||||           780
CCCCGTCGGAGTGGTTCGAGTTCCCCGGCGACTGGTACTACCGCAGGGTGATGTTTGTCG

ACTGCCCCCCACGCCGGAGACGTCGTGCGCCACCCAGATCATCACGTTCGAGTCGTTCA
||||.||||+||||.||||+||||.||||+||||.||||+||||.||||+||||.||||           840
TGACGGGGGGTGCGGCCTCTGCAGCACGCGGTGGGTCTAGTAGTGCAAGCTCAGCAAGT

HindIII
AGGAGAACCTGAAGGACTTCCTCCTTCGTGATCCCCTTCGACTGCTGGGAGCCGGTGCAGGAGTGA
||||.||||+||||.||||+||||.||||+||||.||||+||||.||||+||||.||||           909
TCCTCTTGGACTTCCTGAAGGAGGACACTAGGGGAAGCTGACGACCCTCGGCCACGTCCTCACTTCGA
```

FIG. 5b

BamHI
```
GATCCGGCCGTTTCCCGCGCCGCCCGCGCCCACGTGGCGCGGTGGGGGATTCCGGCCGAA
----.----+----.----+----.----+----.----+----.----+----.----+    60
GCCGGCAAAGGGCGCGGCGGGCGCGGGTGCACCGCGCCACCCCCTAAGGCCGGCTT

CGCGCCGACGCCCATGTGACCGCCTGCGTGCTGCGCGGCGCCCGCGCCGCAGGCTCGCCG
----.----+----.----+----.----+----.----+----.----+----.----+    120
GCGCGGCTGCGGGTACACTGGCGGACGCACGACGCGCCGCGGGCGCGGCGTCCGAGCGGC

GGGCGGACCCGGACCCGGCCGCCGAGGTCCTCGCCGCCGACCGGGAGGCGTGCGGCCTCG
----.----+----.----+----.----+----.----+----.----+----.----+    180
CCCGCCTGGGCCTGGGCCGGCGGCTCCAGGAGCGGCGGCTGGCCCTCCGCACGCCGGAGC

CCGCGAGACCGCCGTCCTGCTGCGGCTCACGGAGGCGTACCTCTCGCCCTGCGCGCGGGC
----.----+----.----+----.----+----.----+----.----+----.----+    240
GGCGCTCTGGCGGCAGGACGACGCCGAGTGCCTCCGCATGGAGAGCGGGACGCGCGCCCG

CCTCGACCCCGCCGGGACCTCCGGCACCGGGCCCGCGGGCGACGCCGGGCGCACCGGGTC
----.----+----.----+----.----+----.----+----.----+----.----+    300
GGAGCTGGGGCGGCCCTGGAGGCCGTGGCCCGGGCGCCCGCTGCGGCCCGCGTGGCCCAG

CGCCGGCGCCCCCCCACCCCGCACAAGAATGTCCGAAACCCTACGGGCCCCGACGAAAGG
----.----+----.----+----.----+----.----+----.----+----.----+    360
GCGGCCGCGGGGGGTGGGGCGTGTTCTTACAGGCTTTGGGATGCCCGGGGCTGCTTTCC

CGCGGAACGGCGTCTCCGCCTCTGCCATGATGCCGCCCATGAGGATCAAGCGCACCAGCA
----.----+----.----+----.----+----.----+----.----+----.----+    420
GCGCCTTGCCGCAGAGGCGGAGACGGTACTACGGCGGGTACTCCTAGTTCGCGTGGTCGT

MluI
ACCGCTCGAACGCGGCGAGACGCGTCCGCACCACCGCCGTACTCGCGGGGCTCGCCGCCG
----.----+----.----+----.----+----.----+----.----+----.----+    480
TGGCGAGCTTGCGCCGCTCTGCGCAGGCGTGGTGGCGGCATGAGCGCCCCGAGCGGCGGC

NsiI            XbaI
TCGCGGCGCTGGCCGTTCCCACCGCCAATGCATTCCCGACCATCCCGCTGT
----.----+----.----+----.----+----.----+----.----+.    535
AGCGCCGCGACCGGCAAGGGTGGCGGTTACGTAAGGGCTGGTAGGGCGACAGATC

HindIII
                                              CTAGCAAGCTTG
                                              ---.----+----.--    547
                                              GTTCGAACGATC
```

FIG. 6b

```
BamHI
GATCCGGCCGTTTCCCGCGCCGCCCGCGCCCACGTGGCGCGGTGGGGGATTCCGGCCGAA
----.----+----.----+----.----+----.----+----.----+----.----+   60
     GCCGGCAAAGGGCGCGGCGGGCGCGGGTGCACCGCGCCACCCCCTAAGGCCGGCTT

CGCGCCGACGCCCATGTGACCGCCTGCGTGCTGCGCGGCGCCCGCGCCGCAGGCTCGCCG
----.----+----.----+----.----+----.----+----.----+----.----+   120
GCGCGGCTGCGGGTACACTGGCGGACGCACGACGCGCCGCGGGCGCGGCGTCCGAGCGGC

GGGCGGACCCGGACCCGGCCGCCGAGGTCCTCGCCGCCGACCGGGAGGCGTGCGGCCTCG
----.----+----.----+----.----+----.----+----.----+----.----+   180
CCCGCCTGGGCCTGGGCCGGCGGCTCCAGGAGCGGCGGCTGGCCCTCCGCACGCCGGAGC

CCGCGAGACCGCCGTCCTGCTGCGGCTCACGGAGGCGTACCTCTCGCCCTGCGCGCGGGC
----.----+----.----+----.----+----.----+----.----+----.----+   240
GGCGCTCTGGCGGCAGGACGACGCCGAGTGCCTCCGCATGGAGAGCGGGACGCGCGCCCG

CCTCGACCCCGCCGGGACCTCCGGCACCGGGCCCGCGGGCGACGCCGGGCGCACCGGGTC
----.----+----.----+----.----+----.----+----.----+----.----+   300
GGAGCTGGGGCGGCCCTGGAGGCCGTGGCCCGGGCGCCCGCTGCGGCCCGCGTGGCCCAG

CGCCGGCGCCCCCCACCCCGCACAAGAATGTCCGAAACCCTACGGGCCCCGACGAAAGG
----.----+----.----+----.----+----.----+----.----+----.----+   360
GCGGCCGCGGGGGGTGGGGCGTGTTCTTACAGGCTTTGGGATGCCCGGGGCTGCTTTCC

CGCGGAACGGCGTCTCCGCCTCTGCCATGATGCCGCCCATGAGGATCAAGCGCACCAGCA
----.----+----.----+----.----+----.----+----.----+----.----+   420
GCGCCTTGCCGCAGAGGCGGAGACGGTACTACGGCGGGTACTCCTAGTTCGCGTGGTCGT
              MluI
ACCGCTCGAACGCGGCGAGACGCGTCCGCACCGCGGCCCTGGCCCTCTCCGCTGCCGCCG
----.----+----.----+----.----+----.----+----.----+----.----+   480
TGGCGAGCTTGCGCCGCTCTGCGCAGGCGTGGCGCCGGGACCGGGAGAGGCGACGGCGGC
                                             PstI
CGCTCGTGCTGGGGTCGACGGCCGCCTCCGGGGCGTCTGCAGAGATCACTAGAATCCCAT
----.----+----.----+----.----+----.----+----.----+----.----+   540
GCGAGCACGACCCCAGCTGCCGGCGGAGGCCCCGCAGACGTCTCTAGTGATCTTAGGGTA
```

FIG. 6b'

```
TGTACAAGGGTAAGTCTTTGAGAAGGCCTTGAAGGAACACGGTTTGTTGGAAGACTTCT
|||||||||||||||||||||||||||||||||||||||||||||||||||||||||||   600
ACATGTTCCCATTCAGAAACTCTTCCGGAACTTCCTTGTGCCAAACAACCTTCTGAAGA

TGCAAAAGCAACAATACGGTATCTCCTCCAAGTACTCTGGTTTCGGTGAAGTCGCTTCCG
|||||||||||||||||||||||||||||||||||||||||||||||||||||||||||   660
ACGTTTTCGTTGTTATGCCATAGAGGAGGTTCATGAGACCAAAGCCACTTCAGCGAAGGC

TTCCATTGACCAACTACTTGGACTCCCAATACTTCGGTAAGATCTACTTAGGTACCCCAC
|||||||||||||||||||||||||||||||||||||||||||||||||||||||||||   720
AAGGTAACTGGTTGATGAACCTGAGGGTTATGAAGCCATTCTAGATGAATCCATGGGGTG

CACAAGAATTCACTGTCTTGTTCGACACCGGGTTCTTCTGACTTCTGGGTCCCATCGATTT
|||||||||||||||||||||||||||||||||||||||||||||||||||||||||||   780
GTGTTCTTAAGTGACAGAACAAGCTGTGGCCAAGAAGACTGAAGACCCAGGGTAGCTAAA

SacI/XbaI
ACTGTAAGTCCAACGCTTGTAAGAACCACCAAAGATTCGACCCAAGAAAGAGCT
|||||||||||||||||||||||||||||||||||||||||||||||||||||         838
TGACATTCAGGTTGCGAACATTCTTGGTTTCTAAGCTGGGTTCTTTCTCGAGATC

HindIII
         CTAGCAAGCTTG
         ||||||||||||                                            850
         GTTCGAACGATC
```

FIG.7b

```
BamHI
GATCCGGCCGTTTCCCGCGCCGCCCGCGCCCACGTGGCGCGGTGGGGGATTCCGGCCGAA
----.----+----.----+----.----+----.----+----.----+----.----+   60
    GCCGGCAAAGGGCGCGGCGGGCGCGGGTGCACCGCGCCACCCCCTAAGGCCGGCTT

CGCGCCGACGCCCATGTGACCGCCTGCGTGCTGCGCGGCGCCCGCGCCGCAGGCTCGCCG
----.----+----.----+----.----+----.----+----.----+----.----+  120
GCGCGGCTGCGGGTACACTGGCGGACGCACGACGCGCCGCGGGCGCGGCGTCCGAGCGGC

GGGCGGACCCGGACCCGGCCGCCGAGGTCCTCGCCGCCGACCGGGAGGCGTGCGGCCTCG
----.----+----.----+----.----+----.----+----.----+----.----+  180
CCCGCCTGGGCCTGGGCCGGCGGCTCCAGGAGCGGCGGCTGGCCCTCCGCACGCCGGAGC

CCGCGAGACCGCCGTCCTGCTGCGGCTCACGGAGGCGTACCTCTCGCCCTGCGCGCGGGC
----.----+----.----+----.----+----.----+----.----+----.----+  240
GGCGCTCTGGCGGCAGGACGACGCCGAGTGCCTCCGCATGGAGAGCGGGACGCGCGCCCG

CCTCGACCCCGCCGGGACCTCCGGCACCGGGCCCGCGGGCGACGCCGGGCGCACCGGGTC
----.----+----.----+----.----+----.----+----.----+----.----+  300
GGAGCTGGGGCGGCCCTGGAGGCCGTGGCCCGGGCGCCCGCTGCGGCCCGCGTGGCCCAG

CGCCGGCGCCCCCCCACCCCGCACAAGAATGTCCGAAACCCTACGGGCCCCGACGAAAGG
----.----+----.----+----.----+----.----+----.----+----.----+  360
GCGGCCGCGGGGGGTGGGGCGTGTTCTTACAGGCTTTGGGATGCCCGGGGCTGCTTTCC

CGCGGAACGGCGTCTCCGCCTCTGCCATGATGCCGCCCATGAGGATCAAGCGCACCAGCA
----.----+----.----+----.----+----.----+----.----+----.----+  420
GCGCCTTGCCGCAGAGGCGGAGACGGTACTACGGCGGGTACTCCTAGTTCGCGTGGTCGT
              MluI
ACCGCTCGAACGCGGCGAGACGCGTCCGCACCACCGCCGTACTCGCGGGGCTCGCCGCCG
----.----+----.----+----.----+----.----+----.----+----.----+  480
TGGCGAGCTTGCGCCGCTCTGCGCAGGCGTGGTGGCGGCATGAGCGCCCCGAGCGGCGGC
```

FIG. 7b

```
                                              Pst I
TCGCGGCGCTGGCCGTTCCCACCGCGAACGCTGCAGAGATCACTAGAATCCCATTGTACA
----.----+----.----+----.----+----.----+----.----+----.----+   540
AGCGCCGCGACCGGCAAGGGTGGCGCTTGCGACGTCTCTAGTGATCTTAGGGTAACATGT

AGGGTAAGTCTTTGAGAAAGGCCTTGAAGGAACACGGTTTGTTGGAAGACTTCTTGCAAA
----.----+----.----+----.----+----.----+----.----+----.----+   600
TCCCATTCAGAAACTCTTTCCGGAACTTCCTTGTGCCAAACAACCTTCTGAAGAACGTTT

AGCAACAATACGGTATCTCCTCCAAGTACTCTGGTTTCGGTGAAGTCGCTTCCGTTCCAT
----.----+----.----+----.----+----.----+----.----+----.----+   660
TCGTTGTTATGCCATAGAGGAGGTTCATGAGACCAAAGCCACTTCAGCGAAGGCAAGGTA

TGACCAACTACTTGGACTCCCAATACTTCGGTAAGATCTACTTAGGTACCCCACCACAAG
----.----+----.----+----.----+----.----+----.----+----.----+   720
ACTGGTTGATGAACCTGAGGGTTATGAAGCCATTCTAGATGAATCCATGGGGTGGTGTTC

AATTCACTGTCTTGTTCGACACCGGTTCTTCTGACTTCTGGGTCCCATCGATTTACTGTA
----.----+----.----+----.----+----.----+----.----+----.----+   780
TTAAGTGACAGAACAAGCTGTGGCCAAGAAGACTGAAGACCCAGGGTAGCTAAATGACAT

Sac I \ / Xbal
AGTCCAACGCTTGTAAGAACCACCAAAGATTCGACCCAAGAAAGAGCT
----.----+----.----+----.----+----.----+----.----+--   832
TCAGGTTGCGAACATTCTTGGTGGTTTCTAAGCTGGGTTCTTTCTCGAGATC
```

FIG. 8

```
BamHI
    GATCCGGCCGTTTCCCGCGCCGCCCGCGCCCACGTGGCGCGGTGGGGGATTCCGGGCGAA
    ----.----+----.----+----.----+----.----+----.----+----.----+   60
    GCCGGCAAAGGGCGCGGCGGGCGCGGGTGCACCGCGCCACCCCCTAAGGCCGGCTT

CGCGCCGACGCCCATGTGACCGCCTGCGTGCTGCGCGGCGCCCGCGCCGCAGGCTCGCCG
    ----.----+----.----+----.----+----.----+----.----+----.----+  120
    GCGCGGCTGCGGGTACACTGGCGGACGCACGACGCGCCGCGGGCGCGGCGTCCGAGCGGC

GGGCGGACCCGGACCCGGCCGCCGAGGTCCTCGCCGCCGACCGGGAGGCGTGCGGCCTCG
    ----.----+----.----+----.----+----.----+----.----+----.----+  180
    CCCGCCTGGGCCTGGGCCGGCGGCTCCAGGAGCGGCGGCTGGCCCTCCGCACGCCGGAGC

CCGCGAGACCGCCGTCCTGCTGCGGCTCACGGAGGCGTACCTCTCGCCCTGCGCGCGGGC
    ----.----+----.----+----.----+----.----+----.----+----.----+  240
    GGCGCTCTGGCGGCAGGACGACGCCGAGTGCCTCCGCATGGAGAGCGGGACGCGCGCCCG

HacII
    CCTCGACCCCGCCGGGACCTCCGGCACCGGGCCCGCGGGCGACGCCGGGCGCACCGGGTC
    ----.----+----.----+----.----+----.----+----.----+----.----+  300
    GGAGCTGGGGCGGCCCTGGAGGCCGTGGCCCGGGCGCCCGCTGCGGCCCGCGTGGCCCAG

CGCCGGCGCCCCCCACCCCGCACAAGAATGTCCGAAACCCTACGGGCCCCGACGAAAGG
    ----.----+----.----+----.----+----.----+----.----+----.----+  360
    GCGGCCGCGGGGGGTGGGGCGTGTTCTTACAGGCTTTGGGATGCCCGGGGCTGCTTTCC

NcoI
    CGCGGAACGGCGTCTCCGCCTCTGCCATGATGCCGCC
    ----.----+----.----+----.----+----.----+-   401
    GCGCCTTGCCGCAGAGGCGGAGACGGTACTACGGCGGGTAC
```

FIG. 9

```
BamHI
GATCCACGCGCTGTGCCCGCCGTGCGCCTTCGCCGATCACTTCATCTGCCCGTTCCCGCC
----.----+----.----+----.----+----.----+----.----+----.----+    60
GTGCGCGACACGGGCGGCACGCGGAAGCGGCTAGTGAAGTAGACGGGCAAGGGCGG

CCCGGGCAACACGCTCGCCGCGGCGGTTTTGGCGGGGGAGCGGAACCGGATCGACGCCTG
----.----+----.----+----.----+----.----+----.----+----.----+   120
GGGCCCGTTGTGCGAGCGGCGCCGCCAAAACCGCCCCCTCGCCTTGGCCTAGCTGCGGAC

ACCCGCGCGAGGCCCCACCGGCCCCGGCAGCCGCACGGCTCCCGGGGCCGGTGACGGATG
----.----+----.----+----.----+----.----+----.----+----.----+   180
TGGGCGCGCTCCGGGGTGGCCGGGGCCGTCGGCGTGCCGAGGGCCCCGGCCACTGCCTAC

TGACCCGCGTGGCCGAAAGGCATTCTTGCGTCCCCCGTCCGGCCCCCTCGATACTCCGGT
----.----+----.----+----.----+----.----+----.----+----.----+   240
ACTGGGCGCACCGGCTTTCCGTAAGAACGCAGGGGGCAGGCCGGGGGAGCTATGAGGCCA

CAGCGATTGTCAGGGGCACGGCGAATTCGAAATCCGGACAGGCCCCCGACTGCGCCTCAC
----.----+----.----+----.----+----.----+----.----+----.----+   300
GTCGCTAACAGTCCCCGTGCCGCTTAAGCTTTAGGCCTGTCCGGGGGCTGACGCGGAGTG

GGGCCCGCCACCCCACAGGAGGGCCCCCGATTCCCCTCGGAGGAACCCGAAGTGAGGATC
----.----+----.----+----.----+----.----+----.----+----.----+   360
CCCGGGCGGTGGGGTGTCCTCCCGGGGGCTAAGGGGAGCCTCCTTGGGCTTCACTCCTAG

MluI
AAGCGCACCAGCAACCGCTCGAACGCGGCGAGACGCGTCCGCACCACCGCCGTACTCGCG
----.----+----.----+----.----+----.----+----.----+----.----+   420
TTCGCGTGGTCGTTGGCGAGCTTGCGCCGCTCTGCGCAGGCGTGGTGGCGGCATGAGCGC

HacII
GGGCTCGCCGCCGTCGCGGCGCTGGCCGTTCCCACCGCGAACGCCGAAACCCCCCGGACG
----.----+----.----+----.----+----.----+----.----+----.----+   480
CCCGAGCGGCGGCAGCGCCGCGACCGGCAAGGGTGGCGCTTGCGGCTTTGGGGGGCCTGC

PstI
TTCAGTGCCAACCAGGCTGCA
----.----+----.----+-   501
AAGTCACGGTTGGTCCG
```

FIG. 10

```
      HacII                    NsiI                      XbaI
     TGGCCGTTCCCACCGCCAATGCATTCCCGACCATCCCGCTGT
    ----.----+----.----+----.----+----.----+----.----+   50
     CGCGACCGGCAAGGGTGGCGGTTACGTAAGGGCTGGTAGGGCGACAGATC
```

FIG. 11

```
                                                    MluI
     CATGAGGATCAAGCGCACCAGCAACCGCTCGAACGCGGCGAGA
    ----.----+----.----+----.----+----.----+----.--      47
         TCCTAGTTCGCGTGGTCGTTGGCGAGCTTGCGCCGCTCTGCGC
```

FIG. 12

```
       HacII                  PstI
      TGGCCGTTCCCACCGCGAACGCTGCA
     ----.----+----.----+----.----+   30
      CGCGACCGGCAAGGGTGGCGCTTGCG
```

FIG. 13

```
MluI                                                                    PstI
CGCGTCCGCACCGCGGGCCCTGGCCTCTCCGCTGCCCGCGCTCGTGCTGGGGTCGACGCCCTCCGGGGCGTCTGCA
----+----.----+----.----+----.----+----.----+----.----+----.----+----.----+--
    AGGCGTGGCGCCCGGGACCGGAGAGGGACGCGGCGCGAGCACGACCCCAGCTGCGGGAGGCCCCGCAG
                                                                         B1
```

FIG. 14.

```
MluI                                                                    PstI
CGCGTGTGGATCTCCCTCCTGTTCGCGCTCGCCCTGATCTTCACCATGGCCTTCGGGTCGACGTCCTCCGCCAGGCTGCA
--+----.----+----.----+----.----+----.----+----.----+----.----+----.----+----+--
  ACACCTAGAGGGAGGACAAGCGCGAGCGGGACTAGAAGTGGTACCGGAAGCCCAGCTGCAGGAGGCGGGTCCG
                                                                           B1
```

FIG. 15. is the sequence of the MluI-PstI DNA fragment encoding the carboxy-terminal 27 amino acids of the omp A signal peptide.

```
    MluI                                                              PstI
CGGCGTGCGGACGGCCATCGCCGGTCGCCCTGGCCGCTTCGCCACCGTCGCCGCAGGCTGCA
----.----+----.----+----.----+----.----+----.----+----.----+-     66
    ACGCCTGCCGGTAGCGGCCAGCCGGGACCGGCGAAGCGGTGGCAGCCGCGTCCG
```

FIG. 16. is the sequence of the SacI-MluI DNA fragment containing a portion of the agarase promoter and encoding the amino terminus of the protease B signal peptide.

```
      SacI
      CTCGAATTTGGGCGCCAGGGTCTGCGGAAGTCATTGCCAAATATAAGATTCTTCAGCCAGGCGGG
      ----·----+----·----+----·----+----·----+----·----+----·----+----·----+ 70
      TCGAGAGCTTAAACCCGCGGTCCCAGACGCCTTCAGTAACGGTTTATATTCTAAGAAGTCGGTCCGCCC

MluI
      AATCGAAGAAGGAGAACGATCATGAGGATCAAGCGCACCAGCAACCGCTCGAACGCGGCGAGA
      ----·----+----·----+----·----+----·----+----·----+----·----+----·-- 137
      TTAGCTTCTTCCTCTTGCTAGTACTCCTAGTTCGCGTGGTCGTTGGCGAGCTTGCGCCGCTCTGCGC
```

FIG. 17. is the sequence of the BamHI-SacI DNA fragment of pUC608 containing the remaining portion of the agarase promoter.

```
BamHI                    PstI
GATCCGTCGACCTGCAGCCGTACCGATTGTCACCCTGCGACACTCCGTGTAGCATTCGGGAAACCGTT
----+----|----+----|----+----|----+----|----+----|----+----|----+----  70
CTAGGCAGCTGGACGTCGGCATGGCTAACAGTGGGACGCTGTGAGGCGACATCGTAAGCCCTTTGGCAA

CACCTCATTGAATGATCAGGCGAGCGAAAGCCCAGAAACTTACCTCCTGGAGCCTAGTCTCCTCCTGCGCC
----+----|----+----|----+----|----+----|----+----|----+----|----+----  140
GTGGAGTAACTTACTAGTCCGCTCGCTTTCGGGTCTTTGAATGGAGGACCTCGGATCGAGGAGGACGCGG

SacI
GTGGAATGATCGTGCCACGTGGGCGTTCCGGAACTTTTTGCACGCACGCGAGCT
----+----|----+----|----+----|----+----|----+----|----  194
CACCTTACTAGCACGGTGCACCCGCAAGGCCTTGAAAAACGTGCCGTGCGC
```

FIG. 18. is the DNA sequence of the PstI-XbaI fragment encoding IL-3.

```
PstI
    GCGCCGATGACGCAGACCACGTCGCTGAAGACGTCGTGGGTGAACTGCTCCAACAT
    ----.----+----.----+----.----+----.----+----.----+----.----+   60
    ACGTCGCGGCTACTGCGTCTGGTGCAGCGACTTCTGCAGCACCCACTTGACGAGGTTGTA

GATCGACGAGATCATCACGCACCTGAAGCAGCCCCCGCTCCCCCTGCTCGACTTCAACAA
    ----.----+----.----+----.----+----.----+----.----+----.----+   120
    CTAGCTGCTCTAGTAGTGCGTGGACTTCGTCGGGGGCGAGGGGGACGAGCTGAAGTTGTT

CCTGAACGGCGAGGACCAGGACATCCTCATGGAGAACAACCTCCGCCGCCCGAACCTCGA
    ----.----+----.----+----.----+----.----+----.----+----.----+   180
    GGACTTGCCGCTCCTGGTCCTGTAGGAGTACCTCTTGTTGGAGGCGGCGGGCTTGGAGCT

GGCCTTCAACCGGGCCGTCAAGTCCCTCCAGAACGCCTCGGCCATCGAGAGCATCCTGAA
    ----.----+----.----+----.----+----.----+----.----+----.----+   240
    CCGGAAGTTGGCCCGGCAGTTCAGGGAGGTCTTGCGGAGCCGGTAGCTCTCGTAGGACTT

GAACCTGCTGCCCTGCCTGCCGCTCGCCACGGCGGCCCCCACCCGGCACCCCATCCACAT
    ----.----+----.----+----.----+----.----+----.----+----.----+   300
    CTTGGACGACGGGACGGACGGCGAGCGGTGCCGCCGGGGGTGGGCCGTGGGGTAGGTGTA

CAAGGACGGGGACTGGAACGAGTTCCGGCGCAAGCTCACGTTCTACCTCAAGACGCTGGA
    ----.----+----.----+----.----+----.----+----.----+----.----+   360
    GTTCCTGCCCCTGACCTTGCTCAAGGCCGCGTTCGAGTGCAAGATGGAGTTCTGCGACCT

XbaI
    GAACGCGCAGGCCCAGCAGACGACCCTCTCCCTCGCGATCTT
    ----.----+----.----+----.----+----.----+----.-   406
    CTTGCGCGTCCGGGTCGTCTGCTGGGAGAGGGAGCGCTAGAAGATC
```

FIG. 19. is the DNA sequence of the SacI-HindIII fragment encoding IL-6.

```
SacI
     CCGAGCGCATCGACAAGCAGATCCGGTACATCCTCGACGGCATCTCGGCGCTGCGG
----.----+----.----+----.----+----.----+----.----+----.----+   60
     TCGAGGCTCGCGTAGCTGTTCGTCTAGGCCATGTAGGAGCTGCCGTAGAGCCGCGACGCC

AAGGAGACGTGCAACAAGTCCAACATGTGCGAGTCGTCGAAGGAGGCCCTCGCGGAGAAC
----.----+----.----+----.----+----.----+----.----+----.----+   120
TTCCTCTGCACGTTGTTCAGGTTGTACACGCTCAGCAGCTTCCTCCGGGAGCGCCTCTTG

AACCTCAACCTCCCCAAGATGGCCGAGAAGGACGGGTGCTTCCAGAGCGGGTTCAACGAA
----.----+----.----+----.----+----.----+----.----+----.----+   180
TTGGAGTTGGAGGGGTTCTACCGGCTCTTCCTGCCCACGAAGGTCTCGCCCAAGTTGCTT

GAGACCTGCCTGGTCAAGATCATCACCGGGCTGCTCGAGTTCGAGGTCTACCTGGAGTAC
----.----+----.----+----.----+----.----+----.----+----.----+   240
CTCTGGACGGACCAGTTCTAGTAGTGGCCCGACGAGCTCAAGCTCCAGATGGACCTCATG

CTGCAAAACCGCTTCGAGTCGAGCGAGGAGCAGGCGCGGGCCGTGCAGATGTCGACCAAG
----.----+----.----+----.----+----.----+----.----+----.----+   300
GACGTTTTGGCGAAGCTCAGCTCGCTCCTCGTCCGCGCCCGGCACGTCTACAGCTGGTTC

GTCCTCATCCAGTTCTTGCAGAAGAAGGCGAAGAACCTGGACGCGATCACCACGCCCGAC
----.----+----.----+----.----+----.----+----.----+----.----+   360
CAGGAGTAGGTCAAGAACGTCTTCTTCCGCTTCTTGGACCTGCGCTAGTGGTGCGGGCTG

CCCACGACGAACGCCTCCCTGCTGACGAAGCTGCAGGCCCAGAACCAGTGGCTCCAGGAC
----.----+----.----+----.----+----.----+----.----+----.----+   420
GGGTGCTGCTTGCGGAGGGACGACTGCTTCGACGTCCGGGTCTTGGTCACCGAGGTCCTG

ATGACCACCCACCTGATCCTGCGGAGCTTCAAGGAGTTCCTCCAGTCCAGCCTCCGGGCC
----.----+----.----+----.----+----.----+----.----+----.----+   480
TACTGGTGGGTGGACTAGGACGCCTCGAAGTTCCTCAAGGAGGTCAGGTCGGAGGCCCGG
             HindIII
CTGCGCCAGATGTA
----.----+----.---  498
GACGCGGTCTACATTCGA
```

FIG. 20. is the sequence of the DNA fragment encoding the amino terminal 23 amino acids of IL-6.

```
                                                SacI     HindIII
CCGGTCCCCCGGGCGAGGACTCCAAGGACGTCGCCGCCCCCACCGCCCAGCCGCTCACGAGCTCCTAA
----.----+----.----+----.----+----.----+----.----+----.----+----.--  77
ACGTGGCCAGGGGGCCCGCTCCTGAGGTTCCTGCAGGTTCCTGAGGTTCCTGCAGCGGCGGGGGTGGCGGTCGGCGAGTGCTCGAGGATTCGA
```

FIG. 21. is the DNA sequence of the PstI-HindIII fragment encoding EPO.

```
PstI                          XhoI
      GCCCCCCGCGCCTCATCTGCGACAGCCGCGTCCTCGAGCGGTACCTGCTCGAAGC
   ----.----+----.----+----.----+----.----+----.----+----.----+    60
      ACGTCGGGGGGCGCGGAGTAGACGCTGTCGGCGCAGGAGCTCGCCATGGACGAGCTTCG

CAAGGAGGCGGAGAATATCACGACGGGGTGCGCCGAGCACTGCTCCCTCAACGAGAACAT
   ----.----+----.----+----.----+----.----+----.----+----.----+   120
      GTTCCTCCGCCTCTTATAGTGCTGCCCCACGCGGCTCGTGACGAGGGAGTTGCTCTTGTA

CACCGTCCCCGACACCAAGGTCAACTTCTACGCCTGGAAGCGCATGGAGGTGGGCCAGCA
   ----.----+----.----+----.----+----.----+----.----+----.----+   180
      GTGGCAGGGGCTGTGGTTCCAGTTGAAGATGCGGACCTTCGCGTACCTCCACCCGGTCGT

GGCGGTCGAGGTCTGGCAGGGGCTCGCGCTCCTCTCCGAGGCGGTCCTCCGCGGCCAGGC
   ----.----+----.----+----.----+----.----+----.----+----.----+   240
      CCGCCAGCTCCAGACCGTCCCCGAGCGCGAGGAGAGGCTCCGCCAGGAGGCGCCGGTCCG

CCTCCTGGTGAACTCGTCCCAGCCGTGGGAGCCGCTCCAGCTGCACGTCGACAAGGCCGT
   ----.----+----.----+----.----+----.----+----.----+----.----+   300
      GGAGGACCACTTGAGCAGGGTCGGCACCCTCGGCGAGGTCGACGTGCAGCTGTTCCGGCA

CTCCGGGCTCCGGTCCCTGACCACGCTGCTGCGCGCCCTCGGTGCCCAGAAGGAGGCCAT
   ----.----+----.----+----.----+----.----+----.----+----.----+   360
      GAGGCCCGAGGCCAGGGACTGGTGCGACGACGCGCGGGAGCCACGGGTCTTCCTCCGGTA

CTCGCCCCCGGACGCCGCCAGCGCCGCCCCGCTGCGGACGATCACGGCGGACACCTTCCG
   ----.----+----.----+----.----+----.----+----.----+----.----+   420
      GAGCGGGGGCCTGCGGCGGTCGCGGCGGGGCGACGCCTGCTAGTGCCGCCTGTGGAAGGC

CAAGCTGTTCCGGGTCTACTCGAACTTCCTGCGGGGGAAGCTGAAGCTCTACACCGGCGA
   ----.----+----.----+----.----+----.----+----.----+----.----+   480
      GTTCGACAAGGCCCAGATGAGCTTGAAGGACGCCCCCTTCGACTTCGAGATGTGGCCGCT

StuI                HindIII
      GGCCTGCCGCACGGGCGACCGGTA
   ----.----+----.----+----.---   508
      CCGGACGGCGTGCCCGCTGGCCATTCGA
```

FIG. 22. is the sequence of the DNA fragment encoding the carboxy terminal 25 amino acids of the modified protease B signal peptide.

```
MluI                                                                    PstI
CGGCGTCCGCACCGGCGTACTCGGCGGCCTGGCTCGCGGCGCTCGCGGCCGTAGCCGTTCCCACGCCCGCCGCTGCA
----.----+----.----+----.----+----.----+----.----+----.----+----.----+----.   75
     AGGCGTGGTGGCGGCATGAGCCGCCGGACCGAGCGCCGGCAGCCGCCGGATCGGCAAGGGTGCGGGCGGGCG
```

FIG. 23. is the DNA sequence of the PstI-HindIII fragment encoding SCP.

PstI
```
        GAGGGGATCTGCCGCAACCGGGTCACGAACAACGTGAAGGACGTGACGAAGCTCGT
        ----.----+----.----+----.----+----.----+----.----+----.----+   60
        ACGTCTCCCCTAGACGGCGTTGGCCCAGTGCTTGTTGCACTTCCTGCACTGCTTCGAGCA

CGCGAACCTGCCGAAGGACTACATGATCACGCTCAAGTACGTCCCCGGCATGGACGTGCT
        ----.----+----.----+----.----+----.----+----.----+----.----+  120
        GCGCTTGGACGGCTTCCTGATGTACTAGTGCGAGTTCATGCAGGGGCCGTACCTGCACGA

CCCGTCCCACTGCTGGATCAGCGAGATGGTGGTGCAGCTGAGCGACAGCCTGACGGACCT
        ----.----+----.----+----.----+----.----+----.----+----.----+  180
        GGGCAGGGTGACGACCTAGTCGCTCTACCACCACGTCGACTCGCTGTCGGACTGCCTGGA

CCTGGACAAGTTCTCGAACATCTCCGAGGGCCTCTCCAACTACTCCATCATCGACAAGCT
        ----.----+----.----+----.----+----.----+----.----+----.----+  240
        GGACCTGTTCAAGAGCTTGTAGAGGCTCCCGGAGAGGTTGATGAGGTAGTAGCTGTTCGA

GGTCAACATCGTGGACGACCTGGTGGAGTGCGTCAAGGAGAACTCGAGCAAGGACCTCAA
        ----.----+----.----+----.----+----.----+----.----+----.----+  300
        CCAGTTGTAGCACCTGCTGGACCACCTCACGCAGTTCCTCTTGAGCTCGTTCCTGGAGTT

GAAGAGCTTCAAGTCCCCCGAGCCCCGCCTGTTCACGCCCGAGGAGTTCTTCCGGATCTT
        ----.----+----.----+----.----+----.----+----.----+----.----+  360
        CTTCTCGAAGTTCAGGGGGCTCGGGGCGGACAAGTGCGGGCTCCTCAAGAAGGCCTAGAA

CAACCGCTCGATCGACGCCTTCAAGGACTTCGTCGTGGCGTCCGAGACCTCCGACTGCGT
        ----.----+----.----+----.----+----.----+----.----+----.----+  420
        GTTGGCGAGCTAGCTGCGGAAGTTCCTGAAGCAGCACCGCAGGCTCTGGAGGCTGACGCA

GGTCAGCTCGACCCTCAGCCCGGAGAAGGACTCGCGGGTGTCGGTCACCAAGCCGTTCAT
        ----.----+----.----+----.----+----.----+----.----+----.----+  480
        CCAGTCGAGCTGGGAGTCGGGCCTCTTCCTGAGCGCCCACAGCCAGTGGTTCGGCAAGTA
```
HindIII
```
        GCTGCCCCCGTCGCCTA
        ----.----+----.----+--  502
        CGACGGGGGCAGCGGATTCGA
```

FIG. 24. is the sequence of the DNA fragment encoding the carboxy terminal 24 amino acids of the protease B-streptavidin hybrid signal peptide.

```
      MluI                                                                    PstI
     CGGCGTCCGGATCGTCGTTGCAGCCATCGCCCGTTCCCTGACCACGGTCTCGATTACGGCCAGCGCGTCTGCA
  ---.----+----.----+----.----+----.----+----.----+----.----+----.----+--  72
     AGGCCTAGCAGCAACGTCGGTAGCGGGCAAAGGGACTGGTGCCAGAGCTAATGCCGGTCGCGCAG
```

FIG. 25. is the DNA sequence of the PstI-HindIII fragment encoding IL-7.

PstI
```
      GACTGCGACATCGAGGGGAAGGACGGCAAGCAGTACGAGTCGGTGCTGATGGTGTC
      ----.----+----.----+----.----+----.----+----.----+----.----+   60
      ACGTCTGACGCTGTAGCTCCCCTTCCTGCCGTTCGTCATGCTCAGCCACGACTACCACAG

CATCGACCAGTTGCTGGACTCGATGAAGGAGATCGGCTCCAACTGCCTCAACAACGAGTT
      ----.----+----.----+----.----+----.----+----.----+----.----+   120
      GTAGCTGGTCAACGACCTGAGCTACTTCCTCTAGCCGAGGTTGACGGAGTTGTTGCTCAA

CAACTTCTTCAAGCGCCACATCTGCGACGCCAACAAGGAGGGAATGTTCCTGTTCCGGGC
      ----.----+----.----+----.----+----.----+----.----+----.----+   180
      GTTGAAGAAGTTCGCGGTGTAGACGCTGCGGTTGTTCCTCCCTTACAAGGACAAGGCCCG

CGCGCGCAAGCTGCGCCAGTTCCTCAAGATGAATTCCACCGGGGACTTCGACCTCCACCT
      ----.----+----.----+----.----+----.----+----.----+----.----+   240
      GCGCGCGTTCGACGCGGTCAAGGAGTTCTACTTAAGGTGGCCCCTGAAGCTGGAGGTGGA

GCTCAAGGTCTCGGAGGGCACGACCATCCTGCTGAACTGCACGGGCCAGGTCAAGGGACG
      ----.----+----.----+----.----+----.----+----.----+----.----+   300
      CGAGTTCCAGAGCCTCCCGTGCTGGTAGGACGACTTGACGTGCCCGGTCCAGTTCCCTGC

GAAGCCCGCCGCCCTCGGGGAGGCCCAGCCGACGAAGAGCTTGGAGGAAAACAAGTCCCT
      ----.----+----.----+----.----+----.----+----.----+----.----+   360
      CTTCGGGCGGCGGGAGCCCCTCCGGGTCGGCTGCTTCTCGAACCTCCTTTTGTTCAGGGA

GAAGGAGCAGAAGAAGCTCAACGACCTGTGCTTCCTGAAGCGGTTGCTCCAGGAGATCAA
      ----.----+----.----+----.----+----.----+----.----+----.----+   420
      CTTCCTCGTCTTCTTCGAGTTGCTGGACACGAAGGACTTCGCCAACGAGGTCCTCTAGTT

HindIII
      GACGTGCTGGAACAAGATCCTCATGGGCACCAAGGAACACTGA
      ----.----+----.----+----.----+----.----+.--   467
      CTGCACGACCTTGTTCTAGGAGTACCCGTGGTTCCTTGTGACTTCGA
```

FIG. 26. is the DNA sequence of the PstI-XbaI fragment encoding TNFα.

```
PstI
        GTGCGGTCCTCGTCCCGCACCCCGTCCGACAAGCCCGTGGCGCACGTGGTGGCGAA
    ----.----+----.----+----.----+----.----+----.----+----.----+    60
        ACGTCACGCCAGGAGCAGGGCGTGGGGCAGGCTGTTCGGGCACCGCGTGCACCACCGCTT

CCCCCAGGCGGAGGGGCAGCTCCAGTGGCTGAACCGGCGCGCGAACGCGCTGCTCGCCAA
    ----.----+----.----+----.----+----.----+----.----+----.----+   120
        GGGGGTCCGCCTCCCCGTCGAGGTCACCGACTTGGCCGCGCGCTTGCGCGACGAGCGGTT

CGGCGTCGAGCTCCGCGACAACCAGCTCGTGGTCCCGAGCGAGGGCCTGTACCTCATCTA
    ----.----+----.----+----.----+----.----+----.----+----.----+   180
        GCCGCAGCTCGAGGCGCTGTTGGTCGAGCACCAGGGCTCGCTCCCGGACATGGAGTAGAT

CTCGCAGGTGCTGTTCAAGGGCCAGGGGTGCCCGTCGACCCACGTCCTGCTGACGCACAC
    ----.----+----.----+----.----+----.----+----.----+----.----+   240
        GAGCGTCCACGACAAGTTCCCGGTCCCCACGGGCAGCTGGGTGCAGGACGACTGCGTGTG

CATCTCGCGCATCGCGGTGTCCTACCAGACCAAGGTGAACCTCCTGTCCGCCATCAAGTC
    ----.----+----.----+----.----+----.----+----.----+----.----+   300
        GTAGAGCGCGTAGCGCCACAGGATGGTCTGGTTCCACTTGGAGGACAGGCGGTAGTTCAG

CCCGTGCCAGCGGGAGACGCCCGAGGGCGCGGAGGCCAAGCCCTGGTACGAGCCGATCTA
    ----.----+----.----+----.----+----.----+----.----+----.----+   360
        GGGCACGGTCGCCCTCTGCGGGCTCCCGCGCCTCCGGTTCGGGACCATGCTCGGCTAGAT

CCTGGGCGGCGTGTTCCAGCTCGAGAAGGGGGACCGGCTGAGCGCCGAGATCAACCGCCC
    ----.----+----.----+----.----+----.----+----.----+----.----+   420
        GGACCCGCCGCACAAGGTCGAGCTCTTCCCCCTGGCCGACTCGCGGCTCTAGTTGGCGGG

XbaI
        CGACTACCTCGACTTCGCCGAGTCCGGGCAGGTGTACTTCGGCATCATCGCGCT
    ----.----+----.----+----.----+----.----+----.----+----.---     478
        GCTGATGGAGCTGAAGCGGCTCAGGCCCGTCCACATGAAGCCGTAGTAGCGCGAGATC
```

FIG. 27. is the DNA sequence of the PstI-HindIII fragment encoding IL-2.

```
PstI
      GCCCCGACGTCCTCGTCGACCAAGAAGACCCAGCTCCAGCTCGAACACCTGCTGCT
      ----.----+----.----+----.----+----.----+----.----+----.----+   60
      ACGTCGGGGCTGCAGGAGCAGCTGGTTCTTCTGGGTCGAGGTCGAGCTTGTGGACGACGA

CGACCTCCAGATGATCCTGAACGGGATCAACAACTACAAGAACCCGAAGCTCACCCGCAT
      ----.----+----.----+----.----+----.----+----.----+----.----+   120
      GCTGGAGGTCTACTAGGACTTGCCCTAGTTGTTGATGTTCTTGGGCTTCGAGTGGGCGTA

GCTGACGTTCAAGTTCTACATGCCGAAGAAGGCCACCGAGCTGAAGCACCTCCAGTGCCT
      ----.----+----.----+----.----+----.----+----.----+----.----+   180
      CGACTGCAAGTTCAAGATGTACGGCTTCTTCCGGTGGCTCGACTTCGTGGAGGTCACGGA

GGAGGAGGAGCTCAAGCCGCTCGAGGAGGTCCTGAACCTCGCGCAGAGCAAGAACTTCCA
      ----.----+----.----+----.----+----.----+----.----+----.----+   240
      CCTCCTCCTCGAGTTCGGCGAGCTCCTCCAGGACTTGGAGCGCGTCTCGTTCTTGAAGGT

CCTGCGCCCCCGGGACCTGATCTCCAACATCAACGTGATCGTCCTGGAACTGAAGGGGTC
      ----.----+----.----+----.----+----.----+----.----+----.----+   300
      GGACGCGGGGGCCCTGGACTAGAGGTTGTAGTTGCACTAGCAGGACCTTGACTTCCCCAG

GGAGACCACCTTCATGTGCGAGTACGCCGACGAGACCGCCACCATCGTCGAATTCCTCAA
      ----.----+----.----+----.----+----.----+----.----+----.----+   360
      CCTCTGGTGGAAGTACACGCTCATGCGGCTGCTCTGGCGGTGGTAGCAGCTTAAGGAGTT
                                                       HindIII
      CCGGTGGATCACCTTCTGCCAGAGCATCATCAGCACCCTCACCTAGGA
      ----.----+----.----+----.----+----.----+----.----+--        412
      GGCCACCTAGTGGAAGACGGTCTCGTAGTAGTCGTGGGAGTGGATCCTTCGA
```

EXPRESSION SYSTEM FOR THE SECRETION OF BIOACTIVE HUMAN GRANULOCYTE MACROPHAGE COLONY STIMULATING FACTOR (GM-CSF) AND OTHER HETEROLOGOUS PROTEINS FROM STEPTOMYCES

This application is a continuation, of application Ser. No. 07/935,314, filed Aug. 26, 1992, abandoned, which is a continuation-in-part of Ser. Nos. (1) 07/844,937 filed Mar. 4, 1992, now abandoned, which is a continuation of Ser. No. 07/221,346 filed Jul. 18, 1988; and (2) 07/224,568 filed Jul. 26, 1988, now U.S. Pat. No. 5,200,327, now abandoned, each of which is a continuation-in-part of Ser. No. 07/863, 546 filed Apr. 6, 1992 now abandoned, which is a continuation of Ser. No. 07/646,466 filed Jan. 25, 1991 now abandoned, which is a continuation of Ser. No. 06/795,331 filed Nov. 6, 1985, now abandoned.

FIELD OF THE INVENTION

This invention relates to secretion of heterologous bioactive proteins, in particular, granulocyte macrophage colony stimulating factor ("GM-CSF") by an expression system inserted into a host selected from the Streptomyces genera.

BACKGROUND OF THE INVENTION

In producing commercially viable proteins, the ability of the microorganism to secrete the protein into the broth in bioactive form is important. However, there are many proteins encoded by genetically engineered DNA constructs which may not be secreted by the cells in which the DNA is expressed or which may not secrete the protein in bioactive form. If the protein is not secreted into the broth, downstream processing is necessary. This means that the cells must be harvested, the cell walls must be broken open, the desired proteins must be recovered in pure form and then such proteins must be chemically re-natured to restore their bioactivity. If the protein is secreted into the broth, but not in its bioactive form, the protein must be treated after secretion to restore its bioactivity.

Some cells and microorganisms carry out the biological equivalent of downstream processing by secreting proteins in bioactive form. The mechanism which directs the secretion of some proteins through the cellular exterior into the outside environment of the cell is not yet fully understood. For example, the species *Streptomyces griseus* secretes many extracellular proteins in bioactive form. It would be expedient if heterologous proteins of commercial value, whose bioactivity is a function of their particular three dimensional molecular structure, could be secreted from Streptomyces at the levels observed for natural extracellular proteins.

Some of the literature relating to genetically engineered DNA constructs has assumed that the production of a functional protein using the information contained in DNA was solved by decoding the DNA. This assumption was based on the principle that the information needed to specify the complex-three-dimensional structure of a protein molecule is contained in the primary amino acid sequence of the protein. However, Canadian Application No. 449,456 entitled *Production of Active Proteins Containing Cystine Residues* filed by Cangene Corporation on Nov. 1, 1985 illustrates that the bioactivity of certain proteins derived from genetically engineered DNA constructs is dependent upon the formation of correctly positioned disulphide bonds. A more effective means was sought than conventional methods for the expression of heterologous genes in a host cell or microorganism. Thus, that invention identified that heterologous proteins could be secreted from a host microorganism in bioactive form without resorting to downstream processing. The use of certain microorganisms in conjunction with an expression system facilitates the formation of disulphide bonds upon expression of the genetically engineered DNA construct. Bioactivity of engineered proteins having cystine residues as an integral and necessary portion of their active structure was achieved by using a regulatory nucleotide sequence selected from a cell or microorganism capable of expressing and excreting homologous disulphide-bonded proteins, the nucleotide sequence being operably linked to a second nucleotide sequence encoding a disulphide bond-containing heterologous protein. The regulatory nucleotide sequence encoded a protein which resulted in heterologous protein secretion from the cell or microorganism. The heterologous protein could be natural or designed.

In Canadian Patent Application no. 542,628 entitled *Characterization and Structure of Genes for Protease A and Protease B from Streptomyces Griseus* filed on Jul. 21, 1987 by Cangene Corporation, a homologous gene expression system was disclosed. That invention related to a regulatory nucleotide sequence which directed the secretion of Protease A and Protease B from *Streptomyces griseus*. Protease A and Protease B are naturally-occurring proteins in *Streptomyces griseus*, thus the terminology "homologous". That application disclosed the regulatory nucleotide sequence which was responsible for one type of homologous secretion in Streptomyces. A gene expression system responsible for homologous expression was useful in constructing various other expression systems for heterologous expression.

Granulocyte macrophage colony stimulating factor ("GM-CSF") is a protein which stimulates the production of white blood cells. GM-CSF holds great promise as a biopharmaceutical for use in association with cancer treatment to aid in the restoration of white blood cells. Naturally occurring GM-CSF is a glycoprotein containing 127 amino acids and two disulphide bonds. GM-CSF is present in only trace quantities in the natural human source, which has prevented detailed structural analysis of the naturally isolated protein. Thus, most of the structural data for the natural GM-CSF is obtained from analysis of the complementary DNA sequence and the expression of a complementary DNA clone in mammalian cells. The GM-CSF which is expressed in mammalian cells contains 127 amino acids and two disulphide bonds, and is present in different glycosylated forms ranging in size from 14 to 35 kilodaltons. Some forms of GM-CSF may contain two N-linked carbohydrate groups and/or three O-linked carbohydrate groups, which accounts for the apparent size heterogeneity.

Moonen, P. J., et al., 1987 (*Proc. Natl. Acad. Sci. U.S.A.*) a process is described for the production of GM-CSF by secretion from chinese hamster ovary cells. The GM-CSF is secreted as a 26-kilodalton glycoprotein which is biologically active. However, the biological activity is increased 20-fold by enzymatically removing the carbohydrate groups, indicating that an unglycosylated form of GM-CSF should be superior for clinical use.

In Ernst, J. F. et al., 1987 (*Bio/Technol.* 5:831–834) a process is described for the production of GM-CSF by secretion from the yeast *Saccharomyces cerevisiae* by using the alpha mating factor precursor. The GM-CSF is secreted as a heterogeneous mixture of glycoproteins ranging in size from 35 to 100 kilodaltons. Only a fraction of the secreted GM-CSF had been correctly processed from the alpha mating factor precursor. The specific biological activity of the glycosylated GM-CSF made in yeast and in mammalian cells was approximately the same. However, the structure of the attached carbohydrate groups of the GM-CSF produced in yeast were different from the natural carbohydrate groups of the GM-CSF produced in mammalian cells.

In Burgess, A. W., et al 1987 (*Blood* 58:43–51) a process is described for the production of an unglycosylated GM-CSF-like polypeptide from the cytoplasm of *E. coli*. The GM-CSF-like polypeptide as isolated from the *E. coli* cells, had an amino terminal methionine, and was reduced, denatured, and biologically inactive. The conversion of the biologically inactive GM-CSF-like polypeptide isolated from *E. coli* to a bioactive form required oxidative renaturation in vitro. The renatured GM-CSF-like polypeptide was still not equivalent to an unglycosylated form of GM-CSF due to the presence of an amino-terminal methionine in the *E. coli* produced protein.

The GM-CSF which is secreted by mammalian cells or yeast is bioactive, but glycosylated. The GM-CSF which is isolated from *E. coli* is unglycosylated, but not bioactive. Thus, the conventional processes for producing GM-CSF require expensive, time consuming, or inefficient downstream processing to convert the form of GM-CSF from the culture to the bioactive, unglycosylated GM-CSF which is preferred for clinical use.

Consequently, a need exists for an expression system which will provide bioactive protein, in particular bioactive GM-CSF, upon secretion. Such a protein product would be different as a structure of matter than conventional protein products since structure determines bioactivity.

SUMMARY OF THE INVENTION

This invention relates to a number of expression systems directing the secretion of heterologous proteins, in particular, granulocyte macrophage colony stimulating factor ("GM-CSF") in bioactive form from a host selected from the Streptomyces genera. In this document, unless the context otherwise requires, "GM-CSF" means substantially pure, non-glycosylated, oxidized GM-CSF protein. The bioactive GM-CSF produced in accordance with this invention is not glycosylated, however, in other respects it mimics its natural counterpart. The GM-CSF of this invention, like its natural counterpart, has correctly positioned intramolecular disulphide bonds. The new product produced in accordance with this invention is termed GM-CSF noglytein. GM-CSF noglytein has full bioactivity upon secretion from the host organism, namely, a host selected from the Streptomyces genera and exhibits all of the structural features of the natural GM-CSF glycoprotein.

In accordance with this invention, a gene expression system is used having a regulatory nucleotide sequence linked to a second nucleotide sequence encoding a heterologous protein. The regulatory sequence includes a signal sequence and a promoter sequence. The signal sequence encodes a peptide which directs the secretion of the heterologous protein in bioactive form from a host selected from the Streptomyces genera. The second nucleotide sequence, which may be natural or synthetic or a combination of natural and synthetic sequences, encodes a heterologous protein.

The expression systems described direct the secretion from Streptomyces hosts of encoded proteins in bioactive form. It is contemplated that the expression systems of this invention could be used in other hosts. In addition, these expression systems may be used to direct the secretion of heterologous proteins other than GM-CSF, in accordance with the teaching of this invention.

In particular, this invention relates to a gene expression system for the secretion of granulocyte macrophage colony stimulating factor ("GM-CSF") in bioactive form from a host selected from the Streptomyces genera. The gene expression system includes a regulatory nucleotide sequence linked to a second nucleotide sequence encoding GM-CSF. The regulatory sequence includes a signal sequence and a promoter sequence. The signal sequence encodes a peptide which directs the secretion of GM-CSF in bioactive form from a host selected from the Streptomyces genera. The second nucleotide sequence, which may be natural or synthetic or a combination of natural and synthetic sequences, may encode GM-CSF.

The signal sequence encodes a signal peptide which directs secretion of the heterologous protein from a host selected from the Streptomyces genera. The signal sequence may encode the signal peptide of *Streptomyces griseus* protease B, *Streptomyces plicatus* endo-B-N-acetylglucosaminidase H, a hybrid of any of these peptides, or any other signal peptide which directs secretion of the heterologous protein, in particular GM-CSF, from a host selected from the Streptomyces genera. The signal sequence may encode the signal peptides of gram positive bacteria, gram negative bacteria, or a hybrid of these peptides. Furthermore, the signal sequence may encode a hybrid of signal peptides of Streptomyces and other bacteria.

The promoter sequence, which directs the synthesis of an RNA encoding a fusion protein composed of the signal peptide joined to the amino terminus of the heterologous protein permits the specific binding of and transcription by at least one type of Streptomyces RNA polymerase holoenzyme. The promoter sequence may include a sequence from the aminoglycoside phosphotransferase gene ("aph") of *Streptomyces fradiae* which permits the specific binding of and transcription by at least one type of Streptomyces RNA polymerase holoenzyme.

The expression system is inserted into a vector capable of transformation and replication in Streptomyces, and the vector is inserted into a host selected from the Streptomyces genera.

According to another aspect of the invention, a process of producing granulocyte macrophage colony stimulating factor in bioactive form secreted from a host selected from the Streptomyces genera is used. The process includes linking a sequence encoding a peptide which directs secretion of GM-CSF in bioactive form and a sequence encoding GM-CSF, inserting the sequences into a vector capable of transformation and replication in Streptomyces, inserting the vector into a host selected from the Streptomyces genera, growing the transformed host, and recovering bioactive GM-CSF.

In accordance with the invention, a signal peptide fused to a heterologous protein is produced by heterologous expression in a host selected from the Streptomyces genera.

In accordance with the invention, a signal peptide fused to GM-CSF is produced by heterologous expression in a host selected from the Streptomyces genera.

In accordance with the invention, bioactive protein is produced by heterologous expression in a host selected from the Streptomyces genera.

In accordance with the invention, bioactive GM-CSF is produced by heterologous expression in a host selected from the Streptomyces genera.

Recombinant DNA derived GM-CSF is secreted in bioactive form from a suitable host, in particular, a host selected from the Streptomyces genera. The GM-CSF is unglycosylated and has intramolecular disulphide bonds upon secretion.

BRIEF DESCRIPTION OF THE DRAWINGS

With reference to the Figures, a variety of short forms have been used to identify restriction sites, deoxyribonucleic acids, vectors and related information. Standard nomenclature has been used in identifying all of these components as is readily appreciated by those skilled in the art.

Preferred embodiments of the invention are described with respect to the drawings, wherein:

FIG. 1. is the DNA sequence (SEQ ID NO: 1) of the PstI-Hind III fragment encoding GM-CSF;

Figure 4A:
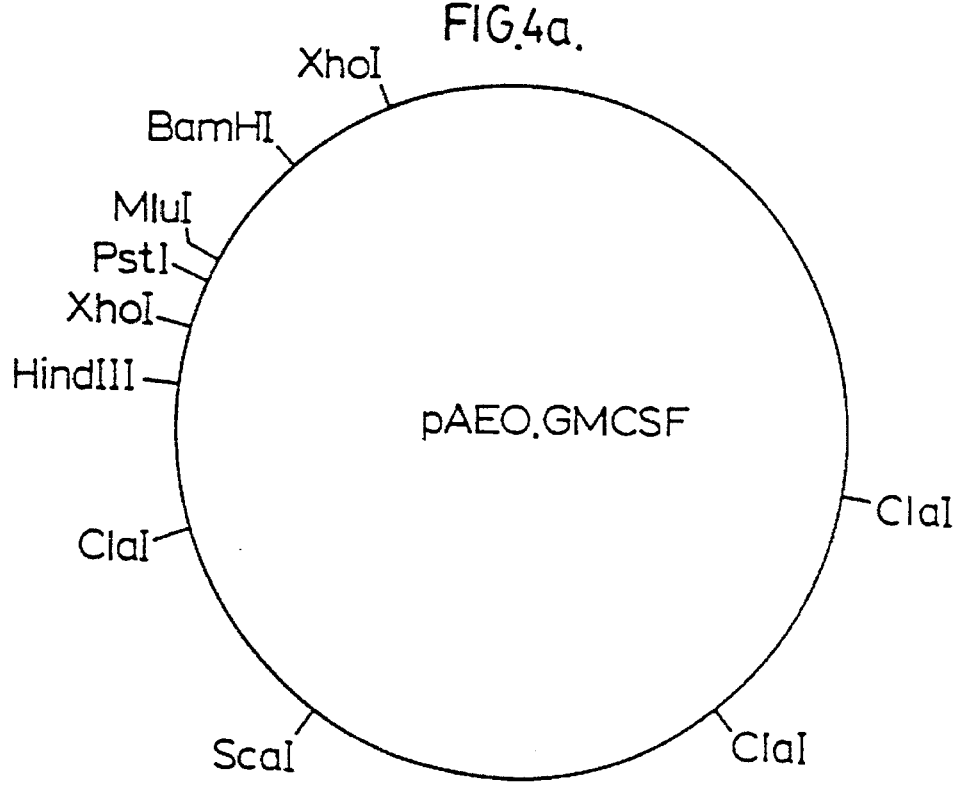
Figure 5A:
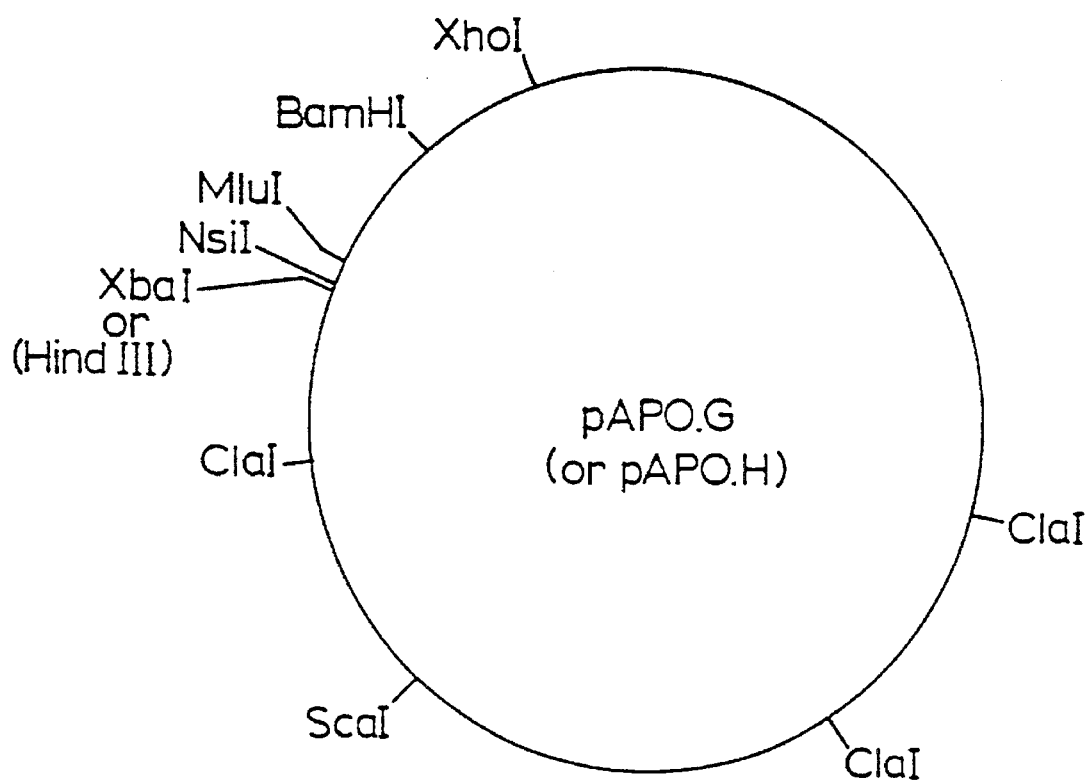
Figure 6A:
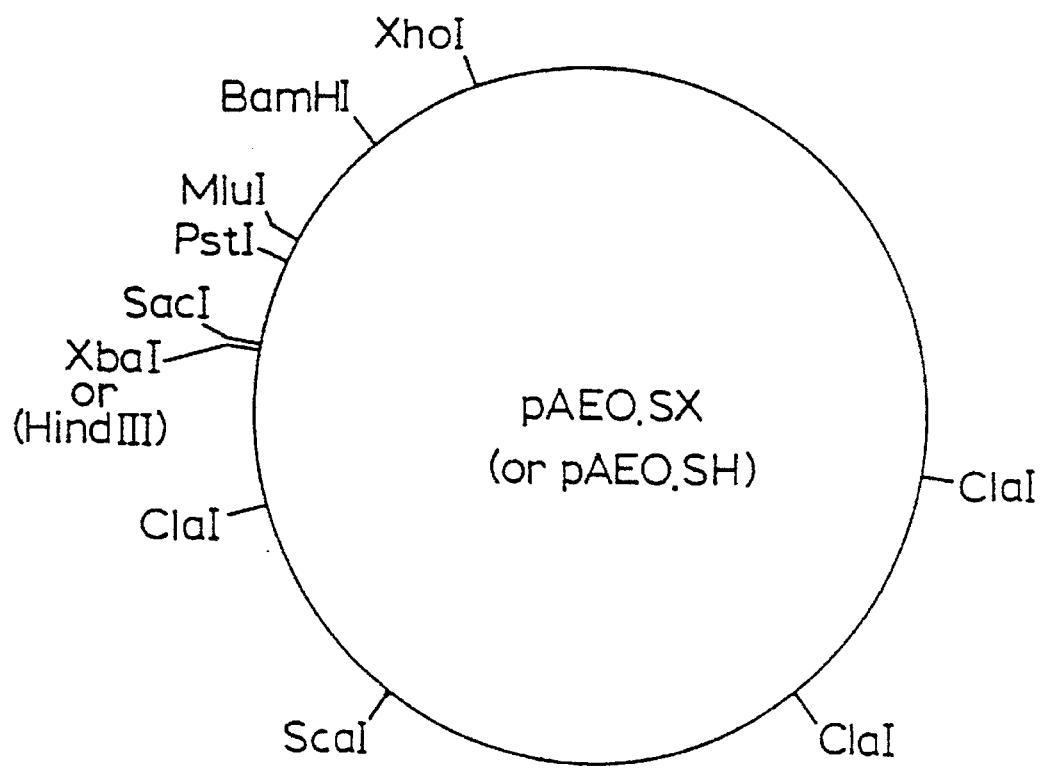
Figure 7A:
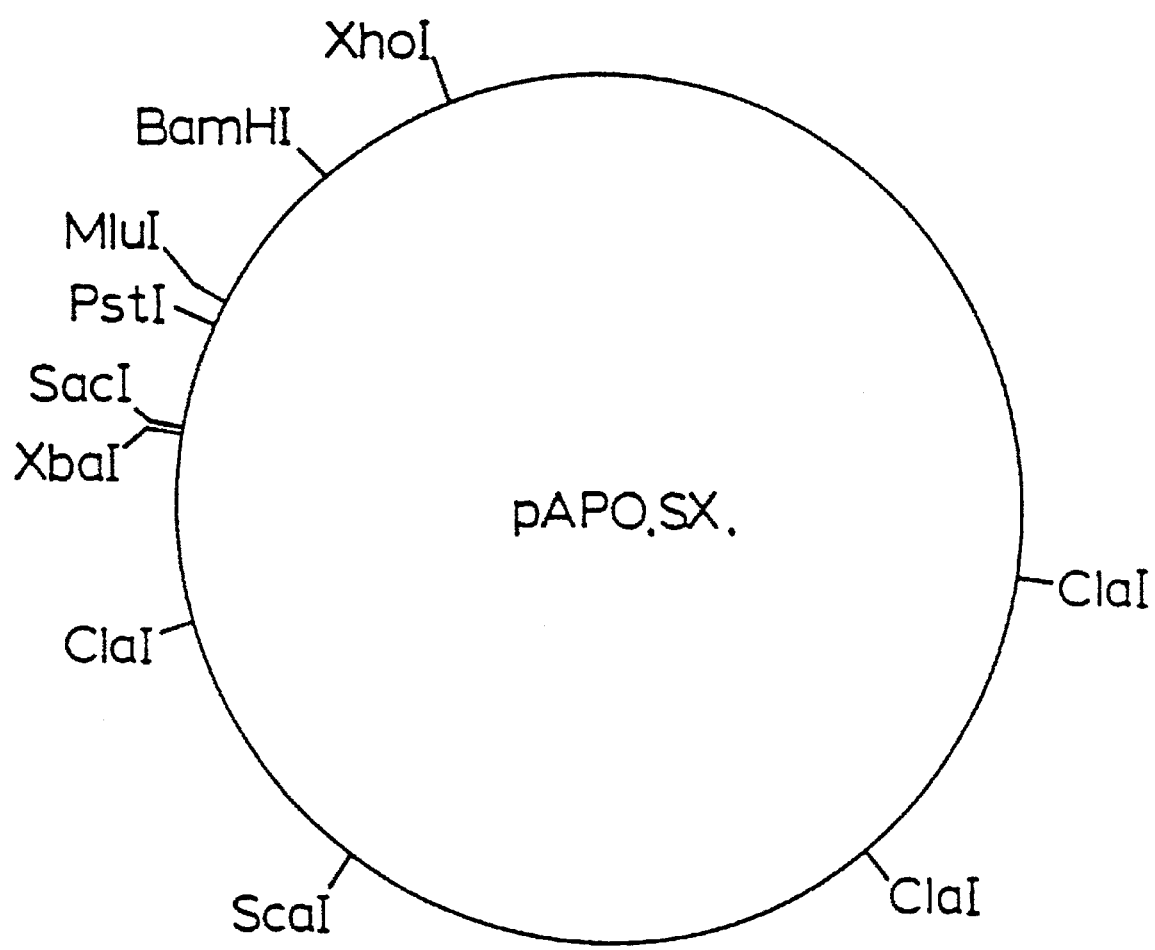

(b') the continuation of the sequence, SEQ ID NO: 7;

FIG. 4. is (a) a restriction map of the expression vector pAEO.G-MCSF; and (b) the sequence (SEQ ID NO: 9) of the inserted BamHI-HindIII DNA fragment;

(b') the continuation of the sequence, SEQ ID NO: 9;

FIG. 5. is (a) a restriction map of the expression vector pAPO.G (or pAPO.H); and (b) the sequence (SEQ ID NO: 11) of the inserted BamHI-XbaI (or BamHI-HindIII) DNA fragment;

FIG. 6. is (a) a restriction map of the expression vector pAEO.SX (or pAEO.SH); and (b) the sequence (SEQ ID NO: 13) of the inserted BamHI-XbaI (or BamHI-Hind III) DNA fragment;

(b') the continuation of the sequence, SEQ ID NO: 13;

FIG. 7. is (a) a restriction map of the expression vector pAPO.SX; and (b) the sequence (SEQ ID NO: 15) of the inserted BamHI-XbaI DNA fragment;

(b') the continuation of the sequence, SEQ ID NO: 15;

FIG. 8. is the sequence (SEQ ID NO: 17) of the BamHI-NcoI DNA fragment containing the aph promoter;

FIG. 9. is the sequence (SEQ ID NO: 23) of the BamHI-Pst DNA fragment of pPP1 containing the protease B promoter and encoding the protease B signal peptide and the amino-terminal 10 amino acids of the protease B propeptide;

FIG. 10. is the sequence (SEQ ID NOS: 20 and 21) of the HaeII-XbaI DNA fragment encoding the carboxy terminus of the protease B signal peptide and the amino terminus of human growth hormone;

FIG. 11. is the sequence (SEQ ID NOS: 25 and 26) of the DNA fragment encoding the amino terminus of the protease B signal peptide;

FIG. 12. is the sequence (SEQ ID NOS: 28 and 29) of the HaeII-PstI DNA fragment encoding the carboxy terminus of the protease B signal peptide;

FIG. 13. is the sequence (SEQ ID NOS: 31 and 32) of the MluI-PstI DNA fragment encoding the carboxy terminal 27 amino acids of the endo H signal peptide;

FIG. 14. is the sequence (SEQ ID NOS: 37 and 38) of the MluI-PstI DNA fragment encoding the carboxy terminal 25 amino acids of the apr signal peptide;

FIG. 15 is the sequence (SEQ ID NOS: 44 and 45) of the MluI-PstI DNA fragment encoding the carboxy terminal 27 amino acids of the omp A signal peptide.

FIG. 16 is the sequence (SEQ ID NO:50) of the SacI-MluI DNA fragment containing a portions of the agarase promoter and encoding the amino terminus of the protease B signal peptide.

FIG. 17 is the sequence (SEQ ID NO:51) of the BamHI-SacI DNA fragment of pUC608 containing the remaining portion of the agarase promoter.

FIG. 18 is the DNA sequence (SEQ ID NO:52) of a PstI-XbaI fragment encoding interleukin-3 (IL-3).

FIG. 19 is the DNA sequence (SEQ ID NO:59) of a SacI-HindIII fragment encoding interleukin 6 (IL-6).

FIG. 20 is the DNA sequence of a double-stranded DNA fragment, comprising a 69-mer (SEQ ID NO:61) and a 77-mer (SEQ ID NO:62), encoding the amino terminal 23 amino acids of interleukin 6 (IL-6).

FIG. 21 is the DNA sequence (SEQ ID NO:69) of a PstI-HindIII fragment encoding erythropoietin (EPO).

FIG. 22 is the sequence (SEQ ID NOS:72 and 73) of the DNA fragment encoding the carboxy terminal 25 amino acids of a modified protease B signal peptide.

FIG. 23 is the DNA sequence (SEQ ID NO:76) of the PstI-HindIII fragment encoding human stem cell factor (SCF).

FIG. 24 is the sequence (SEQ ID NOS:78 and 79) of the DNA fragment encoding the carboxy terminal 24 amino acids of a protease B-streptavidin hybrid signal peptide.

FIG. 25 is the DNA sequence (SEQ ID NO:83) of the PstI-HindIII fragment encoding interleukin 7 (IL-7).

FIG. 26 is the DNA sequence (SEQ ID NO:85) of the PstI-XbaI fragment encoding TNFα.

FIG. 27 is the DNA sequence (SEQ ID NO:88) of the PstI-HindIII fragment encoding interleukin 2 (IL-2).

DETAILED DESCRIPTION OF THE PREFERRED EMBODIMENTS

The present invention describes a process for the production of a biologically active form of human GM-CSF by direct secretion from Streptomyces by using an expression system. It also describes expression vectors which could be used for the production of other heterologous proteins. An expression system contains a gene encoding a particular protein; a nucleic acid sequence encoding a signal peptide which directs secretion of the correctly processed protein into the growth medium; and a promoter capable of directing transcription of mRNA, which encodes the protein. As is known to those skilled in the art, expression systems would include additional nucleic acid sequences for termination of transcription and initiation and termination of translation.

In the preferred embodiment, the gene contained within an expression system encodes the protein human GM-CSF (Lee, F., et al., 1985, *Proc. Natl. Acad. Sci. U.S.A.* 82:4360–4364; Wang, G. G., et al., 1985, *Science* 228:810–814). The GM-CSF gene, specifically the one represented by the DNA sequence (SEQ ID NO: 1) in FIG. 1, is a synthetic DNA which was created following the codon usage of Streptomyces; that is, codons with C or G in the third position (Bibb et al., 1985). The gene could be the natural cDNA sequence for GM-CSF (SEQ ID NO: 2), or any other DNA sequence encoding GM-CSF, with either Streptomyces codon usage, or any other biased or completely random codon usage. The gene could encode a biologically active derivative of GM-CSF in which one or more amino acids are substituted, inserted, or deleted in the natural amino acid sequence.

The heterologous gene contained within an expression system could be natural cDNA or a synthetic DNA sequence encoding another useful protein. The particular protein encoded by the recombinant DNA sequence may include eukaryotic secretory enzymes, such as chymosin, chymotrypsin, trypsins, amylases, ligninases, elastases, lipases, and cellulases; prokaryotic secretory enzymes, such as glucose isomerase, amylases, lipases, pectinases, cellulases, proteinases, oxidases, ligninases; enzyme inhibitors, such as hirudin, B-lactamase inhibitor, and alpha 1-antitrypsin; metalloenzymes, such as superoxide dismutase; blood factors, such as Factor VIII, Factor IX, tissue-type plasminogen activator and urokinase; hormones, such as proinsulin; lymphokines, such as beta and gamma-interferon, and interleukin-2; cytotoxins, such as tumour necrosis factor, lymphotoxin, and interleukin-1; growth factors, such as nerve growth factors, epidermal growth factors, transforming growth factor, platelet-derived growth factors, and fibroblast growth factors; other colony stimulating factors, such as interleukin-3 and granulocyte colony stimulating factor; immunoglobulin-related molecules, such as synthetic, designed, or engineered antibody molecules; cell receptors, such as cholesterol receptor; viral antigens, such as viral hemaglutinins, AIDS antigen and immunogen, hepatitis B antigen and immunogen, foot-and-mouth disease virus antigen and immunogen; bacterial surface effectors, such as protein A; toxins such as protein insecticides, algicides, fungicides, and biocides; and systemic proteins of medical importance, such as myocardial infarct protein (MIP), weight control factor (WCF), and caloric rate protein (CRP).

The gene could encode an inactive precursor (zymogen) of a biologically active protein, which could be processed into an active form either in vitro or in culture. The gene could encode a biologically active derivative of a useful protein in which one or more amino acids are substituted, inserted, or deleted in the natural amino acid sequence. In addition, the gene could encode a biologically active fusion protein of two or more useful proteins, or a hybrid of two or more homologous proteins, which could be created by exchanging single amino acids or blocks of amino acids from homologous positions within the sequences.

The signal sequence could encode any amino acid sequence which, when biosynthesized as an amino-terminal fusion protein, and is linked to a heterologous protein, is capable of directing the secretion of the heterologous protein, with a correct amino terminus, into the medium. In the preferred embodiment, the signal peptide of *Streptomyces griseus* protease B (Canadian Application No. 542,648 filed on Jul. 21, 1987 by Cangene Corporation) is used to direct the secretion of GM-CSF: specifically, a 38-amino acid peptide of the sequence (SEQ ID NO: 3) MRIKRTSNRSNAARRVRTTAVLAG-LAAVAALAVPTANA. In another embodiment, the signal peptide which is used to direct the secretion of GM-CSF is a hybrid composed of the first 15 amino acids of the *S. griseus* protease B signal peptide joined at the amino terminus to amino acids 9 through 34 of the *Streptomyces plicatus* endo-B-N-acetylglucosaminidase H (endo H) signal peptide (Robbins, P. W., et al., 1985, *J. Biol. Chem.* 259:7587–7583) specifically, a 41-amino acid peptide of the sequence (SEQ ID NO: 4) MRIKRTSNRSNAARRVR-TAALALSAAAALVLGSTAASGASA. The secretion of GM-CSF could also be directed by the signal peptide of *S. plicatus* endo H, which is detailed in this invention; specifically a 34-amino acid peptide of the sequence (SEQ ID NO: 5) MFTPVRRRVRTAALALSAAAALVLGSTAASGASA.

The secretion could, in addition, be directed by another Streptomyces signal peptide: specifically, that of *S. griseus* protease A, *S. griseus* amylase, Streptomyces R61 DD-peptidase, or another Streptomyces signal peptide known in the art (Chang, S., 1985, In METHODS IN ENZYMOLOGY (Wu, R. L. & Grossman, L., eds., Academic Press, Inc., New York). Secretion could also be performed under the direction of a hybrid of the above signal peptides or one with a totally synthetic amino acid sequence. The signal peptide could be one from Gram-positive bacteria: specifically the signal peptide of *Bacillus subtilus* alkaline protease (apr), or another signal peptide of a Gram-positive bacteria known in the art (Chang, 1987). The signal peptide could also be from Gram-negative bacteria: specifically, the signal peptide of *Escherichia coli* outer membrane protein A, or another signal peptide of Gram-negative bacteria known in the art (Sjostrom et al., 1987). The signal peptide could also be a hybrid of two or more bacterial signal peptides. In one embodiment, the signal peptide which is used to direct the secretion of GM-CSF is a hybrid composed of the first 15 amino acids of the *S. griseus* protease B signal peptide joined at the amino terminus to amino acids 6 through 30 of the *B. subtilus* apr signal peptide: specifically a 40-amino acid peptide of the sequence (SEQ ID NO: 6) MRIKRTSNRSNAARRVWIS-LLFALALIFTMAFGSTSSAQA. In addition to GM-CSF, other heterologous proteins could be secreted from Streptomyces with the signal peptides detailed in this invention or other bacterial signal peptides known in the art. Levels of secretion that could be achieved are greater than 1 ug/L of culture, but preferably greater than 1 mg/L.

The promoter directs the synthesis of an RNA encoding a fusion protein composed of the signal peptide joined to the amino terminus of the heterologous protein. The promoter permits the specific binding of and transcription by at least one type of Streptomyces RNA polymerase holoenzyme. In the preferred embodiment, the promoter of the *Streptomyces fradiae* aminoglycoside phosphotransferase gene ("aph") (Thompson and Gray, 1983) is used to transcribe the mRNA encoding the signal peptide fused to GM-CSF. This promoter permits the binding of and transcription by at least one type of Streptomyces RNA polymerase holoenzyme. The promoter could be from another Streptomyces spp, including that of *Streptomyces erythreus* erythromycin E, *Streptomyces coelicolor* agarase, or any sequence of known or undetermined origin that has promoter activity as demonstrated by methods known in the art. The promoter may be a hybrid of more than one natural or completely synthetic promoter sequences. The promoter may be a natural or hybrid sequence in which one or more bases have been substituted, inserted or deleted to obtain a mutant version of the promoter with improved function. The mutation events may occur chemically or enzymatically, in either a random or site directed manner, and either in vitro or within a prokaryotic host cell.

The promoter may be either a single promoter with one transcription initiation site or a multiple promoter with two or more transcription initiation sites. In the preferred embodiment, the aph promoter is located on a DNA fragment which has two sites for initiation of transcription. Site 1 would begin transcription at the A of the translation initiator ATG, whereas site 2 would begin transcription 313 bases further upstream from site 1. In another embodiment, the aph promoter with only initiation site 1 is used to transcribe the mRNA encoding the signal peptide fused to GM-CSF. Each transcription initiation site of a multiple promoter may be recognized by the same or different type of RNA polymerase holoenzyme, and may be active at the same or different growth time or developmental state. The promoter with multiple transcription initiation sites may be a natural sequence or a hybrid sequence composed of more than one natural or synthetic single promoter sequences. The promoter, single or multiple, may be active at all times during the culturing (constitutive), or it may be regulated by the presence or absence of certain media components, metabolites, or chemical agents. In addition, the promoter may be regulated by changing the temperature or chemical environment of the culture.

In the preferred embodiment, the aph promoter is joined to a nucleic acid sequence encoding a signal peptide, which is joined in-frame to a nucleic acid sequence encoding a protein, in particular GM-CSF. The aph promoter was joined to synthetic oligonucleotides, which encode a signal peptide, by using an NcoI restriction endonuclease site. This site contains the natural initiator ATG of the aph gene, which in this configuration represents the amino-terminal methionine of the signal peptide. A DNA sequence which is complementary to the 3' end of the 18S ribosomal RNA of *Streptomyces lividans* may be included at this NcoI site to augment the initiation of translation. For convenience, a PstI or NsiI site is positioned at the signal processing site to join a DNA sequence encoding the protein to be secreted. The GCA codon in the PstI or NsiI site represents the alanine at the carboxy terminus of the signal peptide. In the preferred embodiment, the DNA sequences are configured so that the carboxy terminus of the encoded signal peptide is fused directly to the amino terminus of the encoded protein of interest. An additional peptide encoding sequence may be inserted at the PstI or NsiI site to facilitate secretion or processing of the signal peptide. The resulting protein with an amino-terminal extension may be removed either in culture by a natural process or in vitro by known chemical or enzymatic methods.

It is contemplated that the signal peptides which are described in this invention, specifically, the 38-amino acid protease B signal peptide, the 34-amino acid endo H signal peptide, the 41-amino acid protease B-endo H hybrid signal peptide, and the 40-amino acid protease B-apr hybrid signal peptide, may be used with expression systems other than those described in this invention, for the secretion of heterologous proteins. The signal peptides which are described in this invention may be used in other expression systems, particularly expression systems for other gram positive bacteria (Chang 1987), specifically expression systems for *Bacillus subtilis* and *Staphylococcus aureus*. It is also contemplated that a fusion protein may be synthesized by a natural process in a bacterial host other than Streptomyces, and from an expression system, which includes a DNA segment which functions as a promoter, linked to a DNA segment which encodes one of the signal peptides described in this invention, linked to a DNA segment which encodes a heterologous protein. The fusion protein would have at its amino terminus one of the signal peptides which are described in this invention, and at its carboxy terminus a heterologous protein which may be GM-CSF. The carboxy terminus of the signal peptide may be joined directly to the amino terminus of the heterologous protein to form the fusion protein. The fusion protein would be useful for secretion of the heterologous protein in the bacterial host.

The genetic expression system, consisting of a promoter, a nucleic acid sequence encoding a signal peptide, and a nucleic acid sequence encoding the particular protein of interest, is situated in a DNA vector which is capable of transformation and replication in Streptomyces. This vector could contain a derivative of a naturally occurring plasmid of Streptomyces including pIJ101, pSLP1.2, pSCP2*, or a naturally occurring phage of Streptomyces including ØC31, or any non-streptomycete plasmid or bacteriophage which is capable of replication in Streptomyces. The vector may be capable of autonomous replication in the host organism, or may require integration into the chromosome or a large extrachromosomal element of the host organism. In the latter case, the vector would contain appropriate nucleic acid sequences capable of facilitating in vivo recombination with either a specific or undefined DNA sequence in the host genome. These sequences could include a plasmid or phage att site, a recombinogenic sequence of a transposable element, or any sequence with sufficient homology with a segment of the host genome to promote integration. It is contemplated that DNA segments which are naturally amplified in the genome of Streptomyces, specifically the 5.7-kb amplifiable unit of DNA (AUD) of *Streptomyces coelicolor*, may be included in the vector, and used to obtain multiple-copy integration of the genetic expression system. The vector also contains an appropriate gene to provide selection for the transformed strain of the host organism, both during transformation and subsequent culturing of the transformant. This selection marker could provide resistance to an antibiotic such as thiostrepton, kanamycin, viomycin, hygromycin, or it could complement an auxotrophic or conditional lethal mutant of the host organism.

Figure 2:
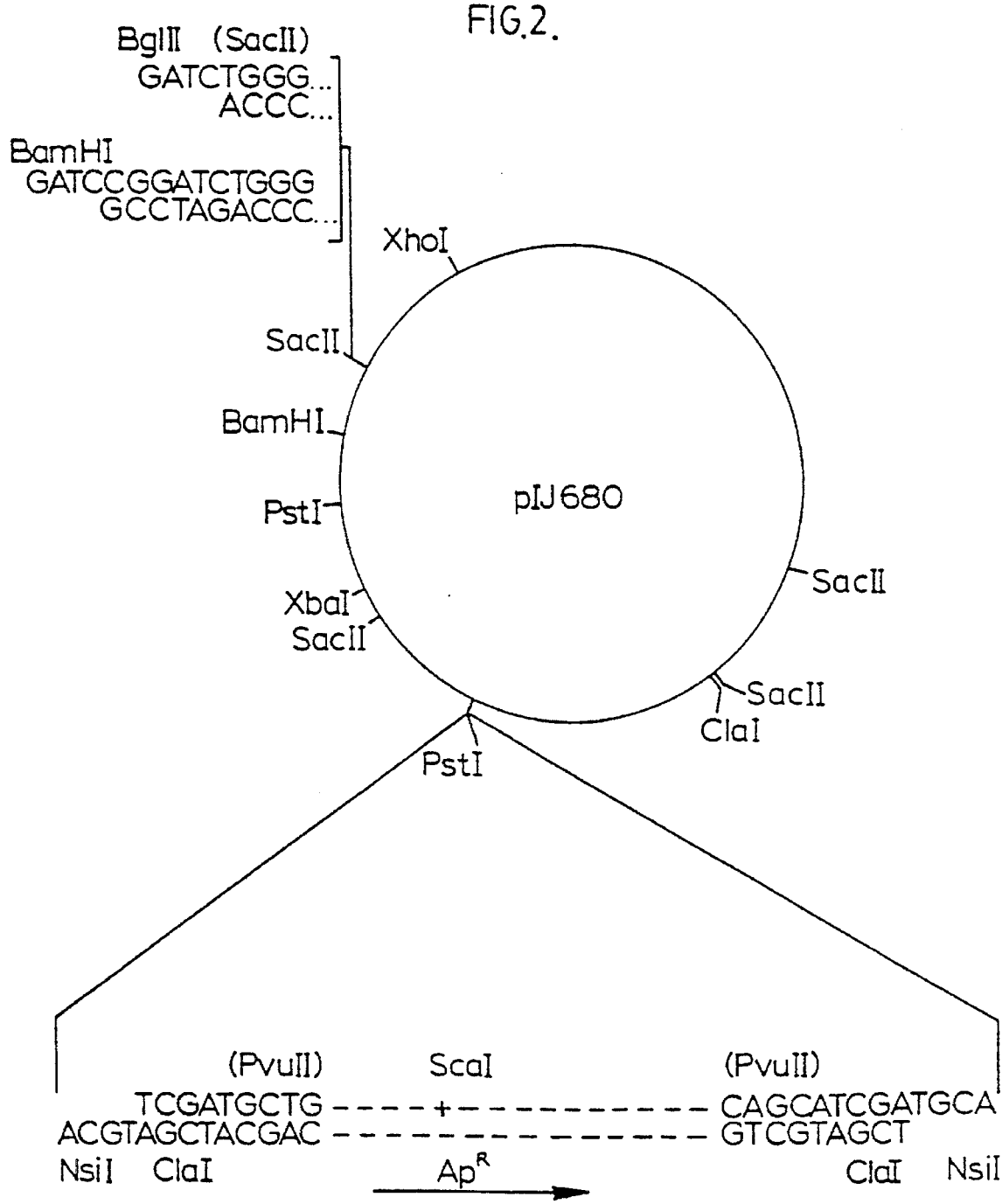
FIG. 2. illustrates the specific alterations of the vector pIJ680.

In the preferred embodiment, the plasmid pIJ680 was adapted for service as a vector according to the modifications outlined in FIG. 2. In the first stage, the 2354-base pair PvuII fragment of the *E. coli* plasmid pUC8 was introduced into the PstI site at position 3390 (site number 16) of pIJ680 (Hopwood, D. A., et al., 1985, GENETIC MANIPULATION OF STREPTOMYCES. A LABORATORY MANUAL. The John Innes Foundation, Norwich, UK). The blunt-ended PvuII fragment was joined to the -TGCA 3' end of the PstI site with a synthetic adaptor as shown in FIG. 2. Vectors with the *E. coli* plasmid inserted at the PstI site are capable of replication in either *E. coli*, under ampicillin selection, or Streptomyces with selection for thiostrepton resistance. It will be appreciated that the *E. coli* plasmid portion of the vector only facilitates assembly of the expression systems in the vector and is not required once the completed plasmid is ready for transformation of Streptomyces. For example, the *E. coli* plasmid segment could be removed prior to transforming Streptomyces by partial digestion with ClaI followed by recircularization of the vector with DNA ligase.

In the second stage, the promoter and coding region of the aph gene was replaced with a synthetic DNA sequence to facilitate future constructions. This involved the alteration of the SacII site at position 4883 (site number 32) of pIJ680 (Hopwood et al, 1985) by ligating a synthetic BglII linker GAGATCTC to the second C in the CCGCGG SacII site. In one embodiment, the BglII site is converted to a BamHI site by ligating a synthetic linker CGGATCCG to the C in the AGATCT BglII site, resulting in the vector pSS2. In another embodiment, the XbaI site is converted to a Hind III site by ligating a synthetic linker CAAGCTTG to the G in the TCTAGA XbaI site.

The BamHI-XbaI fragment of pSS2 could be replaced with an expression system composed of a promoter, a nucleic acid sequence encoding a signal peptide, and a nucleic acid sequence encoding the particular protein of interest. Although the restriction sites BamHI, and XbaI were chosen for convenience, it should be understood that any other restriction site could be used in place of or in addition to these for joining the genetic expression system to the vector. The expression system could be inserted between the BamHI and XbaI sites in either direction, although the preferred orientation would allow transcription in a counter-clockwise direction, as defined by FIG. 2. This would allow utilization of the aph transcription terminator which is adjacent the XbaI site [located between positions 3955 (site 21) and 3843 (site 19) of the original pIJ680 (Hopwood et al, 1985)]. However, any transcription terminator known in the art could be used in place of, or in addition to, the one for aph. The pSS2 vector may have sites for initiation of transcription which are not utilized for expression of the heterologous gene.

Figure 3A:
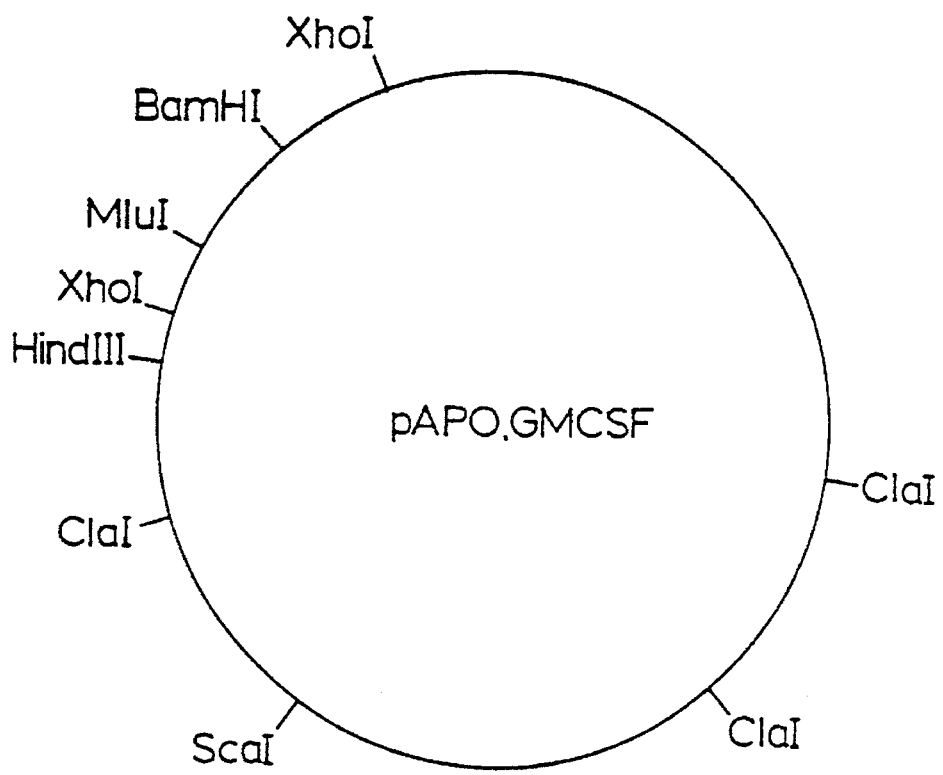
FIG. 3. is (a) a restriction map of the expression vector pAPO.G-MCSF; and (b) the sequence (SEQ ID NO: 7) of the inserted BamHI-HindIII DNA fragment.

Expression vectors can be constructed by inserting various genetic expression systems into the pSS2 vector. According to one embodiment, an expression system pAPO.GMCSF (FIG. 3 and SEQ ID NOS: 7 and 8) contains an aph promoter joined to a nucleic acid sequence encoding the protease B signal peptide which is joined to a nucleic acid sequence encoding GM-CSF. According to another embodiment, an expression system pAEO.GMCSF (FIG. 4 and SEQ ID NOS: 9 and 10) contains an aph promoter joined to a nucleic acid sequence encoding the protease B-endo H hybrid signal peptide which is joined to a replaceable nucleic acid sequence encoding GM-CSF. In another embodiment, an expression system pAPO.G (FIG. 5 and SEQ ID NOS: 11 and 12) contains an aph promoter joined to a nucleic acid sequence encoding the protease B signal peptide which is joined to a replaceable nucleic acid sequence. In a further embodiment, an expression system pAPO.H was constructed from pAPO.G by the insertion of a synthetic DNA (SEQ ID NO: 91) (CTAGCAAGCTTG) into the XbaI site. An expression system pAEO.SX (FIG. 6 and SEQ ID NOS: 13 and 14) contains an aph promoter joined to a nucleic acid sequence encoding the protease B-endo H hybrid signal peptide which is joined to a replaceable nucleic acid sequence. In a further embodiment, an expression system pAE0.SH was constructed from pAE0.SX by the insertion of a synthetic DNA (SEQ ID NO: 91) (CTAGCAAGCTTG) into the XbaI site. Another alternative is an expression system pAP0.SX (FIG. 7 and SEQ ID NOS: 15 and 16) which contains an aph promoter joined to a nucleic acid sequence encoding the protease B signal peptide which is joined to a replaceable nucleic acid sequence.

The BamHI-MluI fragments in all the expression vectors can be replaced with a DNA fragment containing a different promoter and/or encoded signal peptide amino terminus. Also, either the MluI-PstI fragment of pAEO.GMCSF, pAEO.SX, pAEO.SH, or pAPO.SX; or the MluI-NsiI fragment of pAPO.G, or pAPO.H can be replaced with a DNA fragment encoding an alternative signal peptide. Similarly, either the PstI-Hind III fragment of pAEO.GMCSF or pAEO.SH; or the PstI-XbaI fragment of pAEO.SX or pAPO.SX; or the NsiI-HindIII fragment of pAPO.H; or the NsiI-XbaI fragment of pAPO.G can be replaced with another DNA fragment encoding a protein.

Preferred embodiments of the invention are exemplified in the following procedures. Such procedures and results are by way of example and are not intended to be in any way limiting to the scope of the appended claims.

PREPARATIONS

Strains and plasmids

*Streptomyces lividans* 66 (Bibb, M. J., et al., 1980, *Nature* 284:526–531) and plasmids pIJ61 (disclosed by Thompson, C. J., et al., 1982, (*Nature* 286:525–527) and can be isolated from *S. lividans* 66/TC73) and pIJ680 (disclosed by Hopwood et al., 1985, and can be isolated from *S. lividans* TK24/TK425) were from the John Innes Institute. *E. coli* strain HB101 (ATCC 33694) was used for all transformations. Plasmids pUC8 (Vieira, J., et al., 1982, *Gene* 19:259–268), and pUC18 and pUC19 (Norrander, J., et al., 1983, *Gene* 26:101–106) were purchased from Bethesda Research Laboratories. Plasmid pUC680T was deposited with the American Type Culture Collection on Jun. 28, 1988 under accession number 40466.

Materials

Oligonucleotides were synthesized using an Applied Biosystems 380A DNA synthesizer. Columns, phosphoramidites, and reagents used for oligonucleotide synthesis were obtained from Applied Biosystems, Inc. through Technical Marketing Associates. Oligonucleotides were purified by polyacrylamide gel electrophoresis followed by DEAE cellulose chromatography. Enzymes for digesting and modifying DNA were purchased from New England Biolabs, and used according to the supplier's recommendations. Radioisotopes [α-32P]dATP (3000 Ci/mmol) and [γ-32P]ATP (3000 Ci/mmol) were from Amersham. Thiostrepton was donated by Squibb Corporation of New York.

Isolation of DNA

Plasmid DNA of transformed *S. lividans* was prepared by an alkaline lysis procedure (Hopwood et al., 1985). *E. coli* transformants were grown on YT medium (Miller, J. H., 1972, EXPERIMENTS IN MOLECULAR GENETICS. Cold Spring Harbor Laboratory, Cold Spring Harbor, N.Y., p. 433) containing 50 ug/ml ampicillin. Plasmid DNA from *E. coli* was purified by a rapid boiling method (Holmes, D. S., et al., 1983, *Anal. Biochem.* 114:193–197). DNA fragments and vectors used for all constructions were separated by electrophoresis on low melting point agarose, and purified from the molten agarose by phenol extraction and ethanol precipitation (Maniatis et al., 1982).

DNA sequencing

Plasmid DNA, which was purified by HPLC (Edwardson, P. A. D., et al., 1986, *Anal. Biochem.* 152:215–220), was sequenced by using a modification (Hattori, M., et al., 1985, *Nucleic Acids Res.* 13:7813–7827) of the dideoxy method (Sanger, F., et al., 1977, *Proc. Natl. Acad. Sci. U.S.A.* 74:5463–5467). When necessary, subclones were prepared in the M13 bacteriophages mp18 and mp19 (Norrander et al., 1983) and the dideoxy sequencing reactions were run using the -20 universal primer (New England Biolabs). In some areas of strong secondary structure, compressions and polymerase failure necessitated the use of deazaguanosine (Mizusana, S., et al., 1986, *Nucleic Acids Res.* 14:1319–1324) (Boehringer Mannheim) analogs in the dideoxy reactions to clarify the sequence. The sequences were compiled with the software of DNASTAR™ (Doggette, et al., 1985, *Nucleic Acids Res.* 14:611–619).

EXAMPLE 1

Construction of pUC680T

The Streptomyces plasmid pIJ680 (1–2 ug) was linearized by partial digestion with 1.2 units of PstI for 4 min. The 5.3-kb PstI DNA fragments representing the linearized pIJ680 plasmid were mixed with the *E. coli* plasmid pUC8 which had been digested with PstI and calf intestinal alkaline phosphatase. The mixture was then ligated with T4 DNA ligase and transformed into *E. coli*. The transformants were screened by analysis of the plasmid DNA for the correct recombinant. One plasmid, pUC680, had the pUC8 plasmid inserted into the PstI site at position 3390 (site number 16) of pIJ680.

A subclone of pIJ680 was constructed to facilitate the replacement of the aph promoter and coding region. This subclone, pCM680B, contains the 0.41-kb SacII-XhoI DNA fragment of pIJ680 (Hopwood et al, 1985) from positions 4883 to 5290 (between site numbers 32 and 1). The SacII site has been changed to BglII by ligation of the synthetic linkers GAGATCTC to the SacII site which had been made blunt-ended with the Klenow fragment of DNA polymerase I. The newly created BglII site is adjacent to 0.92 kb of synthetic DNA which ends with an XbaI site.

The 1.33-kb XbaI-XhoI DNA fragment of pCM680B, which contains the synthetic DNA fragment joined to the pIJ680 subclone, was mixed with the 6.6-kb XbaI-XhoI DNA fragment of pUC680, which contains the E. coli vector. The mixture was ligated with T4 DNA ligase and transformed into E. coli. The resultant plasmid pUC680T was found by analyzing the plasmid DNA of the transformants. The plasmid pUC680T was deposited with the American Type Culture Collection on Jun. 28, 1988 under accession number 40466.

EXAMPLE 2

Construction of pSS2

The 2.36-kb PvuII fragment of pUC8 was ligated to phosphorylated ClaI linkers (New England Biolabs) of the sequence CATCGATG, using T4 DNA ligase. The ligation reaction was terminated by heating at 65° C. and digested with NsiI, which utilizes the sites generated by the ligation of consecutive linkers. The 2.36-kb NsiI fragment was isolated and mixed with the 5.3-kb PstI fragment of pUC680T. The mixture was ligated using T4 DNA ligase in the presence of NsiI and PstI. The ligation reaction was terminated by heating at 65° C., digested with NsiI, and transformed into E. coli. The plasmid pSS1, which was found by analyzing plasmid DNA of the transformants, contained the E. coli plasmid segment inserted into the former PstI site in the orientation shown in FIG. 2.

The unique BglII site of pSS1 was changed to BamHI to facilitate exchange of promoter sequences. The plasmid pSS1 was digested with BglII and the ends of the linearized plasmid were filled in with the Klenow fragment of DNA polymerase I. The blunt-ended DNA fragment was then ligated to phosphorylated BamHI linkers (New England Biolabs) of the sequence CGGATCCG, using T4 DNA ligase. The ligation reaction was terminated by heating at 65° C., and digested with BamHI. The purified linear plasmid with BamHI ends was then recircularized by using T4 DNA ligase and transformed into E. coli. The resultant plasmid, pSS2, with a unique BamHI site replacing the original BglII site, was found by analyzing the plasmid DNA of the transformants.

EXAMPLE 3

Subcloning a DNA fragment containing the aph promoter

A 2.1-kb EcoRV-NcoI fragment of the Streptomyces plasmid pIJ61 was digested with Sau3AI and ligated into the BamHI and NcoI sites of an appropriate vector. Among the recombinants was found the subclone of pIJ61, pAPH.4, which contained the 0.40-kb Sau3AI-NcoI fragment with a sequence (SEQ ID NO: 17) corresponding to the aph promoter (FIG. 8). The NcoI site contains the initiator ATG of the aph gene.

EXAMPLE 4

Subcloning the DNA fragment containing the protease B promoter and Signal peptide A subclone of the protease B gene was prepared from the 1.4-kb BssHII fragment of plasmid containing the 2.8-kb BglII fragment which contained the protease B gene (Canadian Application No. 542,648 filed on July 21, 1987 by Cangene Corporation). The ends of the BssHII fragment were filled in by using the Klenow fragment of DNA polymerase I, and then ligated to phosphorylated BamHI linkers, following the teaching of Example 2. The resulting 1.4-kb fragment with BamHI ends was ligated into a pUC8 vector which had been digested with BamHI and treated with alkaline phosphatase. The resulting plasmid pSPRB1.4 contained the entire protease B gene.

The plasmid pUC8 was adapted for further subcloning by the ligation of two annealed oligonucleotides (SEQ ID NOS: 18 and 19, respectively), GGCCTCGTCTAGA and AAGCTTCTAGACGAGGCCTGCA, into the PstI and HindIII sites, resulting in the plasmid pUC.PXH. The plasmid pSPRB1.4 was digested with PvuII and ligated to phosphorylated PstI linkers (New England Biolabs) of the sequence GCTGCAGC, using T4 DNA ligase. The ligation reaction was terminated by heating at 65° C., and digested with PstI and BamHI. The 0.49-kb BamHI-PstI fragment was purified and then ligated into the BamHI and PstI sites of the pUC.PXH vector. The resulting plasmid, pPP1, contained the promoter, signal peptide and the first 10 amino acids of the propeptide, all of the protease B gene.

EXAMPLE 5

Construction of expression systems using the protease B Signal peptide

Adaptation of the protease B signal for heterologous protein secretion involved the use of two synthetic oligonucleotides, a 42-mer (SEQ ID NO: 20) and a 50-mer (SEQ ID NO: 21), encoding the carboxy-terminal 9 amino acids of the protease B signal peptide and the amino-terminal 8 amino acids of human growth hormone (SEQ ID NO: 22) (FIG. 10 and SEQ ID NOS: 20 and 21). The synthetic oligonucleotides were joined in a 3-way ligation to a 0.44-kb BamHI-HaeII fragment of the protease B subclone pPP1 (FIG. 9 and SEQ ID NOS: 23 and 24), and the vector fragment of pSS2 which was digested with BamHI and XbaI. The resulting plasmid, pPP0.G, had a 0.46-kb BamHI-NsiI segment containing the protease B promoter and signal peptide. The NsiI site contained a GCA codon for the alanine residue immediately preceding the processing site (−1 position).

The signal peptide of protease B was adapted for expression from the aph promoter by using two synthetic 43-mers (SEQ ID NOS: 25 and 26) encoding the first 15 amino acids of the protease signal peptide (SEQ ID NO: 27) (FIG. 11 SEQ ID NOS: 25 and 26). The synthetic oligonucleotides were joined in a 3-way ligation to the 0.40-kb BamHI-NcoI fragment containing the aph promoter (FIG. 8 and SEQ ID NO: 17), and the BamHI-MluI vector fragment of pPP0.G, following the teaching of this example. The resulting expression vector, pAP0.G, had a 0.51-kb BamHI-NsiI segment containing the aph promoter joined to a sequence encoding the protease B signal peptide, and a 0.03-kb NsiI-XbaI segment containing a replaceable sequence encoding a protein (FIG. 5 and SEQ ID NO: 11).

EXAMPLE 6

Construction of alternative expression systems using the protease B signal peptide A plasmid pPCM, containing a 1.1-kb PstI-XbaI fragment which encodes a protein, was digested with PstI and XbaI, and the 1.1-kb fragment was ligated into the PstI and XbaI sites of the pPP1 vector. The resulting plasmid, pPP1.PCM, contained in a single vector the 0.49-kb BamHI-PstI fragment of pPP1 joined to the 1.1-kb PstI-XbaI fragment of pPCM.

Further adaptation of protease B signal for heterologous protein secretion involved the use of two synthetic 26-mer oligonucleotides (SEQ ID NOS: 28 and 29), encoding the carboxy-terminal 9 amino acids of the protease B signal peptide (SEQ ID NO: 30) (FIG. 12 and SEQ ID NOS: 28 and 29). The synthetic oligonucleotides were joined in a 3-way ligation to the 0.44-kb BamHI-HaeII fragment of pPP1 and the vector fragment of pPP1.PCM which was digested with BamHI and PstI. The resulting plasmid pPPO.PCM had a 0.46-kb BamHI-PstI segment containing the protease B promoter and signal peptide. The PstI site contained a GCA codon for an alanine residue immediately following the processing site (+1 position).

The 1.6-kb BamHI-XbaI fragment of pPPO.PCM was then ligated to the BamHI-XbaI vector fragment of pSS2. The resulting plasmid, pPPO-PCM/S2, contained the protease B promoter and signal peptide, joined to a synthetic DNA segment encoding a protein, all in the pSS2 vector.

The signal peptide of protease B in the pPPO.PCM/S2 construction was adapted for expression from the aph promoter by following the teaching of Example 5. The 43-mer oligonucleotides encoding the first 15 amino acids of the protease B signal peptide were joined in a 3-way ligation to the 0.40-kb BamHI-NcoI fragment containing the aph promoter, and the BamHI-MluI vector fragment of pPPO.PCM. The resulting expression vector, pAPO.PCM, had a 0.51-kb BamHI-PstI segment containing the aph promoter joined to a sequence encoding the protease B signal peptide.

For convenience, the DNA segment encoding the protein in the vector pAPO.PCM was shortened by deleting the 0.8-kb SacI-XbaI fragment. The vector pAPO.PCM was digested with SacI and XbaI, and the vector fragment was recircularized by ligation to the synthetic oligonucleotide CTAGAGCT. The resulting expression vector pAPO.SX (FIG. 7 and SEQ ID NO: 15), which retains sites for both SacI and XbaI, has a 0.51-kb BamHI-PstI segment containing the aph promoter joined to a sequence encoding the protease B signal peptide, and a 0.32-kb PstI-XbaI (or PstI-SacI) segment containing a replaceable sequence encoding a protein.

EXAMPLE 7

Construction of expression systems using the protease B-endo H hybrid signal peptide A synthetic DNA sequence was designed using the amino acid sequence of the endo H signal peptide and the codon usage for Streptomyces. The synthetic sequence and its complement were divided into six oligonucleotides. The first two of these, S1.END (SEQ ID NO: 34) and S2.END (SEQ ID NO: 35), were joined to the aph promoter (see Example 11). The next four of these, S3.END through S6.END, encoded the remaining 27 amino acids of the endo H signal peptide (FIG. 13 and SEQ ID NOS: and 32). The oligonucleotides S4.END and S5.END (2 ug each), were phosphorylated separately in 20-ul reactions containing 10 mM TrisHCl (pH 7.5), 10 mMMgCl2, 5 mM DTT, 0.5 mMATP and 5 units T4 polynucleotide kinase, at 37° C. for 30 min. The phosphorylated oligonucleotides (10 ul of each) were mixed with 1 ug each of unphosphorylated S3.END and S6.END, and 3 ul 500 mM TrisHCl (pH 7.8)-100 mMMgCl2, in a final volume of 31 ul. Annealing of the oligonucleotides was at 90° C. for 10 min, followed by slow cooling to room temperature for 12 to 16 h. The annealed oligonucleotides (15 ul) were ligated together in a 200-ul reaction containing 50 mM TrisHCl (pH 7.8), 10 mMMgCl2, 1 mMATP, and 1600 Units T4 DNA ligase, at 16° C. for 4 h. The completed synthetic gene segment encoding the endo H signal peptide was then ligated to the MluI and PstI sites of the expression vector pAPO.SX, which contained the aph promoter, the protease B signal peptide, and a replaceable synthetic DNA segment (FIG. 7 and SEQ ID NO: 15). This joined the amino-terminal 15 amino acids of the protease B signal to the carboxy-terminal 26 amino acids of the endo H signal, to form a protease B-endo H hybrid signal peptide. The PstI site contains a GCA codon for the alanine at the −1 position of the signal peptide. The resulting expression vector, pAEO.SX, had a 0.52-kb BamHI-PstI fragment containing the aph promoter joined to a sequence encoding the protease B-endo H hybrid signal peptide, and a 0.32-kb PstI-XbaI (or PstI-SacI) segment containing a replaceable sequence encoding a protein (FIG. 6 and SEQ ID NO: 13).

EXAMPLE 8

Construction of a synthetic gene encoding GM-CSF

A synthetic DNA sequence was designed by back translation of the GM-CSF amino acid sequence using a codon selection for Streptomyces. This DNA sequence and its reverse complement were used for the synthesis of 16 oligonucleotides, which were annealed and ligated together, following the teaching of Example 7. The completed 0.48-kb synthetic GM-CSF gene (FIG. 1 and SEQ ID NO: 1) was then ligated into the PstI and XbaI sites of pUC18 and used to transform E. coli. The PstI site contained a GCA codon for the alanine at the −1 position, which is compatible with the protease B and endo H expression systems. After screening the transformants by restriction analysis of the plasmid DNA, the synthetic GM-CSF gene was determined to be authentic by DNA sequence analysis.

EXAMPLE 9

Construction of expression vectors for GM-CSF Using the protease B signal peptide The XbaI site of pAPO.G was converted to a HindIII site to facilitate the insertion of the synthetic GM-CSF gene. The vector pAPO.G was digested with XbaI, and the resulting ends of the linear vector were filled in by using the Klenow fragment of DNA polymerase I, and then ligated to phosphorylated HindIII linkers (New England Biolabs) of the sequence CAAGCTTG, using T4 DNA ligase. The reaction was terminated by heating at 65° C., and digested with HindIII. The purified linear plasmid with HindIII ends was then recircularized by using T4 DNA ligase. The resulting expression vector, pAPO.H, has a 0.51-kb BamHI-NsiI segment containing the aph promoter joined to a sequence encoding the protease B signal peptide, and a 0.03-kb NsiI-HindIII segment containing a replaceable sequence encoding a protein.

The 0.48-kb PstI-XbaI fragment of pUC.GMCSF, containing the GM-CSF gene was ligated to the BamHI-PstI vector fragment of pAPO.G, containing the aph promoter and encoding the protease B signal peptide, by using T4 DNA ligase. In the resulting expression vector, pAP0.GMCSF, the carboxy terminus of the encoded signal peptide is fused directly to the amino terminus of the encoded GM-CSF protein.

EXAMPLE 10

Construction of expression vectors for GM-CSF using the protease B-endo H hybrid signal peptide The XbaI site of pAE0.SX was converted to a HindIII site, by following the teaching of Example 9. The resulting expression vector, pAE0.SH, has a 0.52-kb BamHI-PstI segment containing the aph promoter joined to a sequence encoding the protease B-endo H hybrid signal peptide, and a 0.32-kb PstI-HindIII (or PstI-SacI) segment containing a replaceable sequence encoding a protein.

The 0.48-kb PstI-Hind III of pUC.GMCSF, containing the GM-CSF gene, was ligated to the PstI-Hind III vector fragment of pAE0.SH, containing the aph promoter and encoding the protease B - endo H hybrid signal peptide. In the resulting expression vector, pAE0.GMCSF, the carboxy terminus of the encoded signal peptide is fused directly to the amino terminus of the encoded GM-CSF protein.

EXAMPLE 11

Construction of expression systems using the endo H signal peptide

The amino terminus of the signal peptide in pAEO.GMCSF, was changed from protease B to endo H by replacing the 0.44-kb BamHI-MluI fragment, in a 3-way ligation, with the 0.40-kb BamHI-NcoI fragment of pAPH.4 and the annealed oligonucleotides S1.END (SEQ ID NO: 35) (CATGTTCACTCCCGTTCGGAGA) and S2.END (SEQ ID NO: 35) (CGCGTCTCCGAACCGGAGTGAA) following the teaching of Example 5. The resulting expression vector, pAEO-1.GMCSF, had a 0.50-kb BamHI-PstI fragment containing the aph promoter joined to a sequence encoding the endo H signal peptide.

EXAMPLE 12

Construction of expression vectors for GM-CSF Using the protease B-apr hybrid signal peptide A synthetic DNA sequence was designed using the amino acid sequence of the apr signal peptide and the codon usage for Streptomyces. Construction of the protease B-apr hybrid signal peptide expression vector involved the use of two synthetic oligonucleotides, a 81-mer and a 73-mer, encoding amino acid 15 of the protease B signal peptide and the carboxy terminal 25 amino acids of the apr signal peptide (FIG. 14 and SEQ ID NOS: 37 and 38). The synthetic oligonucleotides were annealed and then ligated to the MluI and PstI sites of the expression vector pAEO.SH (FIG. 6 and SEQ ID NO: 13). The resulting plasmid, pAapr.SH, contained the aph promoter, a sequence encoding the protease B-apr hybrid signal peptide, and a replaceable synthetic DNA segment. The protease B-apr hybrid signal peptide contains the amino terminal 15 amino acids of the protease B signal peptide joined to the carboxy terminal 25 amino acids of the apr signal peptide.

The synthetic GM-CSF gene was adapted to the pAapr. SH expression vector by using two synthetic oligonucleotides, a 21-mer (SEQ ID NO: 40) (CCCGCCCGGTCGCCCTCGCCG) and a 29-mer (SEQ ID NO: 41) (TCGACGGCGAGGGCGACCGGGCGGGTGCA), encoding the amino terminal 9 amino acids (SEQ ID NO: 42) of GM-CSF. The synthetic oligonucleotides were annealed and then joined in a 3-way ligation to a 0.36-kb SalI-HindIII fragment of pUC.GMCSF (FIG. 1) and the vector fragment of pAapr. SH which had been digested with PstI and HindIII. In the resulting expression vector, pAapr.GMCSF, the carboxy terminus of the encoded signal peptide is fused directly to the amino terminus of the encoded GM-CSF protein.

EXAMPLE 13

Construction of expression vectors for GM-CSF Using an aph promoter with a single transcription initiation site The expression vector pAPO.GMCSF was digested with SacII, and the resulting fragments were made blunt-ended by treatment with the Klenow fragment of DNA polymerase I. The blunt-ended SacII fragments were then ligated to phosphorylated BamHI linkers following the teaching of Example 2. The ligation mixture was digested with BamHI and HindIII, and the 0.62-kb fragment was purified. The 0.62-kb BamHI-HindIII fragment, was then ligated to the vector fragment of pAPO.H which had been digested with BamHI and HindIII. The resulting expression vector, pA*PO.GMCSF, had the 0.12-kb aph promoter segment joined to a sequence encoding the protease B signal peptide which was joined to a sequence encoding GM-CSF.

EXAMPLE 14

Transformation of S. lividans with GM-CSF expression systems

Protoplasts of S. lividans 66 that were used for transformations. Cultures of S. lividans 66 were grown in YEME medium (Hopwood et al., 1985) including 0.5% glycine, at 30° C. for 40 h. Protoplasts were prepared from the harvested mycelium by treatment with lysozyme and purified by filtration through Miracloth (Calbiochem Hoechst) as described (Hopwood et al., 1985). Protoplasts ($4 \times 10^9$) were transformed with plasmid DNA of the expression vectors (1 ug) and spread onto R2YE plates as described (Hopwood et al., 1985). After incubating at 30° C. for 22 h, the plates were overlayed with Soft Nutrient Agar, containing thiostrepton (30 ug/ml), and allowed to incubate at 30° C. until sporulation occurred.

EXAMPLE 15

Growth of S. lividans transformants

Ten colonies of S. lividans 66, which had been transformed with a GM-CSF expression vector, were inoculated into 15 ml of LB medium, containing thiostrepton (5 ug/ml), and grown at 32° C. for 65 h. The culture was dispersed by using a 15-ml tissue homogenizer (Tenbroeck-Bellco) and used as inoculum for a second culture. A 2-1 baffled shake flask, containing 200 ml LB medium, plus thiostrepton (5 ug/ml), was inoculated to A600 of 0.2 and incubated at 32° C. for 2–4 days in an environment shaker (240 rpm). Two 10-ml aliquots were removed from the culture at suitable time points between 0 and 96 h of growth. The mycelia, which was used for dry weight determination, were removed by centrifugation at 4000 rpm for 10 min. in a clinical centrifuge at 4° C. The supernatant fractions which contained secreted proteins including GM-CSF, were frozen at −20° C. prior to analysis.

EXAMPLE 16

Monitoring Secretion of GM-CSF

The supernatant fraction described in Example 15 which contain secreted proteins including GM-CSF were analyzed by polyacrylamide gel electrophoresis and the protein or proteins of interest visualized either by staining with a protein specific stain or by analysis by Western blotting. 1.5 ml aliquots of the culture supernatants were concentrated by addition of a 50% (w/v) solution (on ice) of trichloroacetic acid (TCA) to a final concentration of 10% (w/v) and incubation of the resulting mixture at approximately 4° C. for approximately 15–30 minutes. The precipitate which forms, which includes secreted proteins including GM-CSF, was collected by centrifugation in an Eppendorf centrifuge at maximum speed for 5 minutes at room temperature. The precipitated samples were prepared for electrophoresis according to the method described by Laemmli, 1970 (Nature 227:680–685), including a modification to adjust the pH of the resuspended TCA precipitates to that of the sample buffer by the addition of 2N NaOH. Polyacrylamide gels (15% acrylamide) were run according to the procedure described by Laemmli, (1970).

The profile of proteins separated by the procedure described above was visualized by staining with Coomassie Brilliant Blue. A novel protein band is present in the cells containing the GM-CSF gene which runs with an apparent molecular weight of approximately 15,500 Daltons when compared to Pharmacia Low Molecular Weight standards. This band was identified as GM-CSF by its cross-reaction with a monoclonal antibody against GM-CSF. This analysis was performed by Western blotting of the proteins separated by gel electrophoresis where the novel protein band found in the GM-CSF transformants cross-reacts with the antibody raised against GM-CSF. Western blotting was performed according to the procedure of Towbin, H., et al., 1979 (*Proc. Natl. Acad. Sci. U.S.A.* 76:4350–4354 as modified by Burnette, W. N., 1981 (Anal. Biochem. 112:195–203).

Quantitation of the level of secretion of GM-CSF was performed by scanning both Coomassie Brilliant Blue stained gels and Western blots, (Table I). Total protein in the supernatants was determined by Bio-Rad protein assay.

The levels of secreted GM-CSF are highest in the S, lividans containing pAPO.GMCSF. Slightly lower levels of secreted GM-CSF were observed for pA*PO.GMCSF (lanes 11–12), which contained the aph promoter with the single initiation site. Substitution of the carboxy-terminal 23 amino acids of the protease B signal peptide in pAPO.GMCSF, with the carboxy-terminal 26 amino acids of the endo H signal peptide in pAEO.GMCSF, or with the carboxy-terminal 25 amino acids of the aph signal peptide in pAapr.GMCSF, resulted in approximately 3 fold lower levels of secreted GM-CSF. However, the levels of secreted GM-CSF were higher by using the protease B-endo H hybrid signal peptide of pAEO.GMCSF than by using the endo H signal peptide of pAEO-1.GMCSF, indicating than the hybrid signal peptide is better than the natural signal peptide.

EXAMPLE 17

Testing biological activity of GM-CSF

The biological activity for secreted GM-CSF was determined by the methylcellulose colony stimulating assay whereby the cells are scored for their ability to stimulate the growth of colonies in soft agar. In summary non-adherent bone marrow cells for the hematopoietic colony-stimulating activity assay were prepared from samples obtained from healthy adult human subjects as described by Gregory, G. J., et al., 1977 (*Blood* 49:855–864). For assays the cells were plated at a final concentration of approximately $5 \times 10^4$ cells/ml. The culture medium contained 0.8% methylcellulose, 30% fetal Calf Serum (Flow), 1% deionized bovine serum albumin (BSA, Sigma Chemical Co., St. Louis), 0.1 mM 2-mercaptoethanol and alpha medium as described by Coulombel et al (1983) and Cashman et al (1985). Cells were incubated in the presence of the media containing the growth factor for a time period of generally 7–14 days at 37° C. in a fully humidified atmosphere of 5% $CO_2$ in air. Colonies were scored in situ under an inverted microscope.

The analysis of biological activity was performed for both pAPO.GMCSF and pAEO.GMCSF (Table II) and in both cases there was demonstration of the significant stimulation of Granulocyte/Macrophage type colonies with a low level of stimulation of large Erythroid/Mixed colonies in the same ratio as found with 10% human leucocyte conditioned media (containing human GM-CSF).

TABLE I

Expression of GM-CSF from different constructs transformed in *S. lividans* 66.

| CONSTRUCT | TIME (h) | DRY WT (g/l) | GM-CSF (mg/l) |
| --- | --- | --- | --- |
| pAPO.GMCSF | 28 | 1.9 | 14.5 |
| pAEO.GMCSF | 28 | 2.0 | 4.0 |
| pAEO-1.GMCSF | 28 | 2.2 | <0.1 |
| pAapr.GMCSF | 28 | 2.2 | 4.0 |
| pA*PO.GMCSF | 28 | 2.2 | 12.0 |

TABLE II

Colony stimulating activity of supernatants of pAPO.GMCSF and pAEO.GMCSF and also a negative control sample transformed with a different heterologous gene.

| | | # Of Colonies Stimulated | |
| --- | --- | --- | --- |
| CONSTRUCT | TIME | Large Erythroid/ Mixed | Granulocyte/ Macrophage |
| pAPO.GMCSF | 22 | 14 | 118 |
| pAPO.GMCSF | 29 | 13 | 124 |
| pAEO.GMCSF | 22 | 16 | 113 |
| pAEO.GMCSF | 29 | 9 | 106 |
| pAPO.CONTROL | 22 | 0 | 5 |
| pAPO.CONTROL | 29 | 0 | 3 |
| AUTHENTIC HUMAN GM-CSF | N/A* | 22 | 120 |

*Not applicable.

EXAMPLE 18

Purification of GM-CSF

GM-CSF was purified in small quantities by elution of the GM-CSF band from a polyacrylamide gel. 10 ml of supernatant proteins were harvested at approximately 24 h of growth and the mycelia removed by centrifugation at 4000 rpm for 10 min. in a clinical centrifuge at 4° C. The supernatant proteins which include GM-CSF were concentrated according to the teaching of Example 16 and separated on a 15% polyacrylamide gel run according to the procedure of Laemmli (1970) with the modifications for the sample preparation and running of the gel described by Hunkapiller, M. W., et al., 1983 (*Methods in Enzymology* 91:227–236). The GM-CSF protein band was isolated by the gel elution procedure described by Hunkapiller et al., (1983) and the resulting protein solution concentrated by freeze drying. The purity and nature of the eluted band was analyzed following the teaching of Example 16.

EXAMPLE 19

Analysis of amino-terminal sequence of GM-CSF

A sample of GM-CSF, which was purified from a sample of culture supernatant as described in Example 18, was analyzed by the Institut de Recherche en Biotechnologie, Montreal, Canada. Amino-terminal sequencing was performed on an Applied Biosystems Gas Phase Sequenator employing the Edman automated degradation cycling technique (Edman, P., et al., 1987, *Eur. J. Biochem.* 1:80–91. The sequence (SEQ ID NO: 43) obtained for the first 9 amino acids of the protein was APARSPSPS which agrees with the expected amino acid sequence.

EXAMPLE 20

Construction of an expression vector for GM-CSF using the protease B-omp.A hybrid signal peptide A synthetic DNA sequence was designed using the amino acid sequence of signal peptide of the *E. coli* outer membrane protein A (omp A) (Sjostrom, et al., 1987) and the codon usage for Streptomyces. Construction of an expression vector with the protease B-omp A hybrid signal peptide involved the use of two synthetic oligonucleotides, a 66-mer (SEQ ID NO:44) and a 58-mer (SEQ ID NO:45), encoding amino acids 15 through 17 of the protease B signal peptide and the carboxy terminal 18 amino acids of the omp A signal peptide, plus an additional carboxy terminal alanine (FIG. 15). The amino acid sequence translated from nucleotides 1 through 66 of SEQ ID NO:44 is disclosed in SEQ ID NO:46. The complete exemplary hybrid signal peptide has the amino acid sequence disclosed in SEQ ID NO:47.

More generally, the amino acid sequence of a protease B-omp A hybrid signal peptide of this invention is constructed by substituting the positively-charged amino terminal amino acids, for instance, from one to about 17, and preferably 17 of the amino terminal amino acids of protease B for the corresponding positively-charged amino terminus of a signal peptide selected from a Gram-negative bacteria.

Following the teaching of Example 12, the synthetic oligonucleotides were annealed and then ligated to the MluI and PstI sites of the expression vector pAE0.SH (FIG. 6). The resulting plasmid, pAM0.SH, contained the aph promoter, a sequence encoding the protease B-omp A hybrid signal peptide, plus an additional carboxy terminal alanine, and a replaceable synthetic DNA segment. The exemplary protease B-omp A hybrid signal peptide contains the amino terminal 17 amino acids of the protease B signal peptide joined to the carboxy terminal 18 amino acids of the omp A signal peptide.

Further following Example 12, the synthetic GM-CSF gene was adapted to the pAM0.SH expression vector by using two synthetic oligonucleotides, a 21-met (CCCGCGCGCTCCCCCAGCCCG; SEQ ID NO:48) and a 29-mer (TCGACGGGCTGGGGGAGCGCGCGGGTGCA; SEQ ID NO:49), encoding the amino terminal 9 amino acids of GM-CSF, minus the amino terminal alanine. The protein sequence translated from nucleotide 1 through 21 of SEQ ID NO:48 is presented in SEQ ID N0:42. The synthetic oligonucleotides were annealed and then joined in a 3-way ligation to a 0.36-kb SalI-HindIII fragment of pUC.GMCSF (FIG. 1; and nucleotides 29 through 392 of SEQ ID NO:1) and the vector fragment of pAM0.SH which had been digested with PstI and HindIII. In the resulting expression vector, pAM0.GMCSF, the carboxy terminus of the encoded protease B-omp A hybrid signal peptide is fused directly to the amino terminus of the encoded GM-CSF protein.

EXAMPLE 21

Construction of an expression vector for GM-CSF using the agarase promoter

The plasmid pMT608, which is a pIJ702 vector containing a subclone of the agarase gene from *S. coelicolor* (Buttner, M. J., et al., 1988, *Cell* 52:599–607) was digested with PvuII and ligated to HindIII linkers as described in Example 9. The ligation reaction was digested with HindIII and PstI, and the 1.95-kb fragment, which contained the agarase gene, was ligated to the HindIII-PstI vector fragment of pUC8 to form the plasmid pUC608. The agarase promoter was adapted for the GM-CSF expression vector by using a synthetic DNA segment which contained the 91-bp region of the agarase promoter preceding the initiation codon joined to a 46-bp region encoding the amino terminal 14 amino acids of the protease B signal peptide. The sequence of this synthetic DNA segment is presented in FIG. 16 and SEQ ID NO:50, and the encoded amino acid sequence translated from nucleotides 92 through 133 is disclosed in SEQ ID NO:27.

The synthetic DNA segment was divided into four oligonucleotides which were phosphorylated and annealed as described in Example 7. The synthetic DNA was joined in a 3-way ligation to the 0.19-kb BamHI-SacI fragment of pUC608 containing part of the agarase promoter (FIG. 17 and SEQ ID NO:51), and the BamHI-MluI vector fragment of pAP0.GMCSF as described in Example 5. In the resulting expression vector, pGP0.GMCSF, the agarase promoter is joined to a sequence encoding the protease B signal peptide which is fused to the GM-CSF protein.

EXAMPLE 22

Secretion of GM-CSF using various signal peptides and promoters

Protoplasts of *S. lividans* 66 were prepared and transformed with the GM-CSF expression vectors according to Example 14. Single colonies of the resulting transformants were grown in liquid culture, and supernatant fractions were collected as in Example 15. As described by Laemmli, 1970, supra, samples were prepared from aliquots (45 µl) of the supernatant fractions, and 15% polyacrylamide gels were run at 9 mA for 16 h. The profile of separated proteins was visualized by silver staining. The relative level of GM-CSF secretion was determined by scanning the silver-stained gel with an optical densitometer. Total protein in the culture supernatants was determined by Bio-Rad protein assay. The separated proteins were also analyzed by Western blotting (Towbin et al., 1979, supra; Burnette, 1981, supra) using rabbit antiserum raised against GM-CSF and an alkaline phosphatase conjugated goat antibody raised against rabbit whole immunoglobulin G (Bethesda Research Laboratories). For Western blot analysis, 100 µl aliquots of the supernatant fractions were used.

The amount of GM-CSF antigen was determined by ELISA assay. Briefly, 100 µl aliquots of appropriate dilutions of the culture supernatants containing GM-CSF were bound to wells of microtiter plates. The bound GM-CSF was reacted with a mouse monoclonal antibody raised against a recombinant GM-CSF (Genzyme) which was reacted with an alkaline phosphatase conjugated goat antibody raised against mouse whole immunoglobulin G (Sigma). The bound enzyme is then detected using the ELISA Amplification System (Bethesda Research Laboratories).

A novel protein band was present in the culture supernatant of cells containing the GM-CSF expression vector, but was absent in a control culture supernatant of cells containing an expression vector without the GM-CSF gene. The novel protein band migrated with an apparent molecular weight of approximately 15.5 kilo- Daltons relative to Pharmacia Low Molecular Weight standards. The novel protein band also reacts uniquely with the antibody raised against GM-CSF.

The maximum level of secreted GM-CSF was observed in the cultures of cells containing the expression vector pAP0.GMCSF. Replacement of the protease B signal with the endo H signal (pAE0-1.GMCSF) resulted in a 10 to 20 fold reduction in the level of secreted GM-CSF. However, when only the carboxy terminal 20 amino acids of the protease B signal peptide were replaced with the carboxy terminal 23 amino acids of the endo H to form the protease B-endo H hybrid signal (pAE0.GMCSF), the reduction in GM-CSF secretion was approximately two-fold. Thus, the protease B-endo H hybrid signal peptide functioned significantly better than the natural endo H signal peptide for the secretion of GM-CSF.

Still lower levels of GM-CSF were observed in culture supernatants of cells containing expression vectors with either the protease B-apr hybrid signal (pAapr. GMCSF) or the protease B-omp A hybrid signal (pAM0.GMCSF). Lower levels of secreted GM-CSF were observed in culture supernatants of cells containing expression vectors in which the aph promoter of pAP0.GMCSF was altered or replaced. Shortening the aph promoter by 276 bp (pAEP0.GMCSF) or replacing the aph promoter with the agarase promoter (pGP0.GMCSF) each resulted in two-fold reductions in the levels of GM-CSF secretion. The amounts of GM-CSF that were secreted into the culture supernatants of cells containing each GM-CSF expression vector is summarized in Table III.

A DNA sequence encoding this IL-3 gene is presented in FIG. 18 and SEQ ID NO:52, and the amino acid sequence translated from nucleotide 5 through 403 is disclosed in SEQ ID NO:53.

A gene encoding a natural variant of human IL-3 (Otsuka, T., et al., 1988, *J. Immunol.* 140:2288–2295) which has a proline instead of serine at amino acid number seven was also constructed. The 0.41-kb PstI-XbaI fragment encoding IL-3S was ligated into the PstI and XbaI sites of pT7T3 19U (Pharmacia), resulting in the plasmid pT7T3.IL3S. The DNA fragment encoding the amino terminal eleven amino acids of IL-3S was replaced with a DNA fragment composed of two 34-mer oligonucleotides, (GCGCCGATGACGCAGACCACGCCGCTGAAGACGT; SEQ ID N0:54 and CTTCAGCGGCGTGGTCTGCGT-CATCGGCGCTGCA; SEQ ID N0:55), encoding the amino acid sequence, disclosed in SEQ ID NO:56, that was translated from nucleotides 1 through 33 of SEQ ID NO:54. These were annealed together and ligated into the PstI and AatII sites of pT7T3.IL3S. The PstI-XbaI fragment of the resulting plasmid, pT7T3.IL3P, which encodes a form of IL-3 with a proline at amino acid number seven ("IL-3P"), was determined to be authentic by DNA sequence analysis. The PstI site of each gene contained a GCA codon for the alanine at the −1 position, which is compatible with the protease B and endo H expression systems.

The 0.41-kb PstI-XbaI fragment of pUC.IL3S was ligated to the NsiI-XbaI vector fragment of pAP0.G, containing the aph promoter and encoding the protease B signal peptide, by using T4 DNA ligase. In the resulting expression vector, pAP0.IL3S, the carboxy terminus of the encoded protease B signal peptide is fused directly to the amino terminus of the

TABLE III

Secretion of GM-CSF from *S. lividans* which was transformed with expression vectors containing various signal peptides and promoters.

| Expression Vector | Time (h) | Dry Weight of Cells (g/l) | Total Secreted Protein (mg/l) | Relative GM-CSF Secretion** | GM-CSF Antigen by ELISA (mg/l) |
|---|---|---|---|---|---|
| pGP0.GMCSF | 19 | 0.77 | 71 | 0.56 | 2.2 |
| pA*P0.GMCSF | 17 | 0.99 | 63 | 0.69 | 3.3 |
| pAP0.GMCSF | 19 | 0.95 | 63 | 1.00 | 7.2 |
| pAE0-1.GMCSF | 17 | 1.24 | 60 | 0.05 | 0.7 |
| pAE0.GMCSF | 19 | 0.95 | 61 | 0.42 | 4.0 |
| pAapr.GMCSF | 19 | 0.88 | 64 | 0.16 | 2.1 |
| pAM0.GMCSF | 19 | 0.78 | 54 | 0.21 | 2.5 |

**The product of total secreted protein and the % of GM-CSF, normalized to the highest level of secretion. The % of GM-CSF was determined by densitometer scanning of gel in which the secreted proteins were separated by SDS-PAGE and visualized by silver staining.

EXAMPLE 23

Use of the Streptomyces expression system for secretion of bioactive human interleukin-3 ("IL-3")

A synthetic DNA sequence was designed by reverse translation ("backtranslation") of the IL-3 amino acid sequence (Yang, Y., et al., 1986, Cell 47:3–10) using a codon selection optimized for Streptomyces. This DNA sequence and its reverse complement were used for the synthesis of 12 oligonucleotides which were annealed and ligated together as in Example 7. The completed 0.41-kb synthetic IL-3 gene was then ligated into the PstI and XbaI sites of pUC18 and used to transform *E. coli*. The 0.41-kb PstI-XbaI fragment of the resulting plasmid, pUC.IL3S, which encodes a form of IL-3 with a serine at amino acid number seven ("IL-3S"), was determined to be authentic by DNA sequence analysis.

encoded IL-3S protein. The same 0.41-kb PstI-XbaI fragment of pUC.IL3S was also ligated to the PstI-XbaI vector fragment of pAE0.SX, containing the aph promoter and encoding the protease B-endo H hybrid signal peptide, by using T4 DNA ligase. In the resulting expression vector, pAE0.IL3S, the carboxy terminus of the encoded protease B-endo H hybrid signal peptide is fused directly to the amino terminus of the encoded IL-3S protein. The aph promoter of pAEO.IL3S was replaced with the agarase promoter according to Example 21. In the resulting expression vector, pGEO.IL3S, the agarase promoter is joined to a sequence encoding the protease B-endo H hybrid signal peptide which is fused to the IL-3S protein.

As shown above in this example, pT7T3.IL3P and pAP0.G were used to construct the expression vector pAP0.IL3P, in which the carboxy terminus of the encoded protease B signal peptide is fused directly to the amino terminus of the encoded IL-3P protein.

Protoplasts of *S. lividans* 66 were prepared and transformed with the IL-3 expression vectors (Example 14). Single colonies of the resulting transformants were grown in liquid culture, and supernatant fractions were collected (Example 15). The proteins that were secreted into culture supernatant fractions were analyzed by polyacrylamide gel electrophoresis and Western blotting as in Example 22. The profile of separated proteins, as visualized by silver staining, shows that a novel protein band was present in the culture supernatants of cells transformed with an IL-3 expression vector, but was absent in a control culture supernatant of cells containing an expression vector without the IL-3 gene. The novel protein migrated with an apparent molecular weight of approximately 15,000 Daltons.

Western blot analysis of the proteins separated by gel electrophoresis indicates that the novel protein band found for IL-3 transformants reacts uniquely with the antibody raised against IL-3. The level of secreted IL-3 was approximately 10 times higher from an *S. lividans* transformant containing pAP0.IL3S (7.5 µl aliquot) than from one containing pAE0.IL3S (30 µl aliquot). Also, the level of secreted IL-3S from an *S. lividans* transformant containing pGE0.IL3S (30 µl aliquot) was slightly lower than from that containing pAE0.IL3S. The level of IL-3 secretion was slightly higher from a transformant containing pAP0.IL3P, than from that containing pAP0.IL3S, due to enhanced stability of IL-3P.

The SDS-polyacrylamide gel analysis indicates that at least two forms of IL-3S were secreted over an 8 h time interval. One form appeared initially at 15 h, but was gradually replaced with another form, which predominated at 23 h. In contrast, the migration of IL-3P remained constant from 15 h to 23 h. To investigate these various forms of IL-3, the amino terminal sequences were analyzed. *S. lividans* which contained the pAP0.IL3S and pAP0.IL3P expression vectors were grown in TSB medium for 17 h and 23 h, according to Example 15. The proteins that were secreted into the culture supernatant fractions were concentrated by ultrafiltration, separated by SDS-polyacrylamide gel electrophoresis, and transferred to a PVDF membrane as described (Matsudaira, P., 1987, *J. Biol. Chem.* 262:10035–10038). The bands containing the IL-3 proteins were excised from the membrane and analyzed as described in Example 19.

The protein which was present in the 17 h culture supernatant of the pAP0.IL3S transformant had an amino terminal sequence of XPMTQTTSXK (SEQ ID NO:57), which agrees with the expected amino terminal sequence of IL-3S. (X indicates a mixture of more than one amino acid was recovered at a particular cycle.) However, the sequence of the faster-migrating protein from the 23 h culture supernatant indicated that the amino terminal seven amino acids of IL-3S were missing. In contrast, the protein which was present in the 23 h culture supernatant of the pAP0.IL3P transformant had the amino terminal sequence of XPMTQT-TPXX (SEQ ID N0:58), which agrees with the expected sequence for intact IL-3P. Thus, both IL-3S and IL-3P were initially secreted as intact proteins, but IL-3S was gradually degraded in culture to a form which is missing the amino terminal seven amino acids. The IL-3P form, which has a proline instead of serine at the amino terminal side of the potential scissile bond, was resistant to the proteolytic activity present in the 23 h culture.

The biological activity of the secreted IL-3 was determined by using the activity assay for GM-CSF as described in Example 17. As shown in Table IV, culture supernatants of cells containing an IL-3 expression vector had a level of activity corresponding to the estimated level of secreted IL-3 protein. By comparison, no IL-3 activity was observed in control cultures of *S. lividans* transformed with an expression vector lacking the IL-3 gene.

TABLE IV

Colony stimulating activity of culture supernatants of *S. lividans* transformed with either pAP0.IL3S, pAE0.IL3S, or a negative control vector containing a different heterologous gene.

| EXPRESSION VECTOR | TIME (h) | # OF COLONIES STIMULATED | |
|---|---|---|---|
| | | Erythroid/ Mixed | Granulocyte/ Macrophage |
| pAP0.IL3S | 22 | 11 | 76 |
| pAP0.IL3S | 28 | 10 | 98 |
| pAP0.IL3S | 34 | 18 | 120 |
| pAP0.IL3S | 47 | 8 | 19 |
| pAE0.IL3S | 22 | 9 | 66 |
| pAE0.IL3S | 28 | 13 | 56 |
| pAE0.IL3S | 34 | 12 | 78 |
| pAE0.IL3S | 47 | 11 | 79 |
| pAP0.control | 28 | 0 | 3 |
| pAP0.control | 34 | 1 | 3 |
| 10 ng/ml recombinant human IL-3 | | 14 | 112 |
| 10% human leucocyte conditioned medium | | 5 | 172 |
| Medium (negative control) | | 0 | 4 |

EXAMPLE 24

Use of the Streptomyces expression system for secretion of bioactive human interleukin-6 ("IL-6")

A synthetic DNA sequence was designed by backtranslation of the IL-6 amino acid sequence (Hirano, T., et al., 1986, *Nature* 324:73–76), using a codon selection optimized for Streptomyces. This DNA sequence and its reverse complement were used for the synthesis of 18 oligonucleotides, 16 of which were annealed and ligated together, following the teaching of Example 7. The resulting 0.50-kb synthetic gene segment, encoding the carboxy terminal 164 amino acids of the IL-6 protein, was then ligated into the SacI and HindIII sites of pT7T3 19U and used to transform *E. coli*. The 0.50-kb SacI-HindIII fragment of the resulting plasmid, pT7T3.IL6, which contains the synthetic IL-6 gene segment, was determined to be authentic by DNA sequence analysis. A DNA sequence of this gene segment is presented in FIG. 19 and SEQ ID NO:59, and the amino acid sequence translated from nucleotides 1 to 492 is disclosed in SEQ ID NO:60.

The remaining two synthetic oligonucleotides, a 69-mer (SEQ ID NO:61) and a 77-mer (SEQ ID NO:62) encoded the amino terminal 23 amino acids of the IL-6 protein (FIG. 20). The amino acid sequence of these amino terminal amino acids of the IL-6 protein, which was translated from nucleotides 1 through 60 of SEQ ID NO:61, is disclosed SEQ ID NO:63. These two synthetic oligonucleotides were annealed and then ligated to the NsiI-HindIII vector fragment of pAP0.H, containing the aph promoter and encoding the protease B signal peptide, by using T4 DNA ligase. In the resulting expression vector, pAP0.IL6S1, the carboxy terminus of the encoded protease B signal peptide is fused directly to the amino terminus of the encoded IL-6 amino terminal peptide. The 0.50-kb SacI-HindIII fragment of pT7T3.IL6, encoding the remaining carboxy terminal 164 amino acids of IL-6, was then ligated to the SacI-HindIII vector fragment of pAP0.IL6S1, encoding the first amino terminal 20 amino acids of IL-6. In the resulting expression vector, pAP0.IL6, the carboxy terminus of the encoded protease B signal peptide is fused to the amino terminus of the encoded and complete IL-6 protein.

The same two synthetic oligonucleotides, encoding the amino terminal 20 amino acids of IL-6, were annealed and then ligated to the NsiI-HindIII vector fragment of pAE0.SH, containing the aph promoter and encoding the protease B signal peptide, by using T4 DNA ligase. In the resulting expression vector, pAP0.IL6S1, the carboxy terminus of the encoded protease B -endo H hybrid signal peptide is fused directly to the amino terminus of the encoded IL-6 amino terminal peptide. The 0.50-kb SacI-HindIII fragment of pT7T3.IL6, encoding the remaining carboxy terminal 164 amino acids of IL-6, was then ligated to the SacI-HindIII vector fragment of pAP0.IL6S1, encoding the first amino terminal 20 amino acids of IL-6. In the expression vectors pAE0.IL6, the carboxy terminus of the encoded protease B-endo H hybrid signal peptide is fused to the amino terminus of the encoded and complete IL-6 protein.

A natural variant of the IL-6 protein has been characterized (Brakenhoff J. P., et al., 1987, J. Immunol. 139:4116–4121; van Damme, J., et al., 1987, J. Exp. Med. 165: 914–919) which contains an additional alanine at the amino terminus ("aIL-6"). The construction of expression vectors for aIL-6 involved the use of expression vectors with PstI sites which contained a GCA codon for an alanine residue that immediately followed the signal peptide processing site (+1 position). An alternative expression vector encoding the protease B signal peptide, plus an additional alanine, pAP0.SX, was described in Example 6 and FIG. 7.

An alternative expression vector encoding the protease B-endo H hybrid signal peptide, plus an additional alanine, was constructed by using two synthetic oligonucleotides, a 30-mer (TCGACGGCCGCCTCCGGGGCGTCGGCTGCA; SEQ ID NO:64) and a 22-mer (GCCGACGCCCCGGAGGCGGCCG; SEQ ID NO:65), encoding the carboxy-terminal nine amino acids of the endo H signal peptide, plus an additional alanine. This amino acid sequence, translated from nucleotides 1 through 30 of SEQ ID NO:64, is disclosed in SEQ ID NO:66. The synthetic oligonucleotides were joined in a 3-way ligation to the 0.50-kb BamHI-SalI fragment of pAE0.SX and the BamHI-PstI vector fragment of pAP0.SX, following the teaching of Example 5. The resulting expression vector, pAE1.SX, had a 0.52-kb BamHI-PstI segment containing the aph promoter joined to a sequence encoding the protease B-endo H hybrid signal peptide, and a 0.32-kb PstI-XbaI (or PstI-SacI) segment containing a replaceable sequence encoding a protein. The PstI site contained a GCA codon for an alanine residue immediately following the processing site (+1 position).

The same two synthetic oligonucleotides, encoding the amino terminal 20 amino acids of IL-6, were annealed and then ligated into the PstI and HindIII sites of an expression vector containing the aph promoter and encoding the protease B signal peptide, plus an additional alanine, of pAP0.SX. In the resulting expression vector, pAP0.aIL6S1, the carboxy terminus of the encoded protease B signal peptide is fused via the additional alanine residue to the amino terminus of the encoded IL-6 amino terminal peptide. The 0.50-kb SacI-HindIII fragment of pT7T3.IL6, encoding the remaining carboxy terminal 164 amino acids of IL-6, was then ligated to the SacI-HindIII vector fragment of pAP0.aIL6S1, encoding the first amino terminal 21 amino acids of aIL-6. In the resulting expression vector, pAP0.aIL6, the carboxy terminus of the encoded protease B signal peptide is fused to the amino terminus of the encoded and complete aIL-6 protein.

The same two synthetic oligonucleotides, encoding the amino terminal 20 amino acids of IL-6, were annealed and then ligated into the PstI and HindIII sites of an expression vector containing the aph promoter and encoding the protease B-endo H hybrid signal peptide, plus an additional alanine, of pAE1.SX. In the resulting expression vector, pAE0.aIL6S1, the carboxy terminus of the encoded protease B -endo H hybrid signal peptide is fused via the additional alanine residue to the amino terminus of the encoded IL-6 amino terminal peptide. The 0.50-kb SacI-HindIII fragment of pT7T3.IL6, encoding the remaining carboxy terminal 164 amino acids of IL-6, was then ligated to the SacI-HindIII vector fragment of pAE0.aIL6S1, encoding the first amino terminal 21 amino acids of aIL-6. In the resulting expression vector, pAE0.aIL6, the carboxy terminus of the encoded protease B-endo H hybrid signal peptide is fused to the amino terminus of the encoded and complete aIL-6 protein.

Protoplasts of S. lividans 66 were prepared and transformed with the IL-6 expression vectors (Example 14). The resulting transformants were grown in liquid culture, and supernatant fractions were collected (Example 15). The proteins that were secreted into the culture supernatant fractions (30 µl aliquots) were analyzed by polyacrylamide gel electrophoresis and Western blotting (Example 22).

The profile of separated proteins, as visualized by silver staining, shows that a novel protein band was present in the culture supernatants of cells transformed with three of the IL-6 expression vectors, but was absent in a control culture supernatant of cells containing an expression vector without the IL-6 gene. The novel protein band migrated with an apparent molecular weight of approximately 21,000 Daltons. Western blot analysis of the proteins separated by gel electrophoresis indicates that the novel protein band found for IL-6 transformants reacts uniquely with the antibody raised against IL-6.

The levels of secreted IL-6 were higher from the S. lividans transformants containing pAE0.aIL6 than from those containing pAP0.aIL6. There was no significant difference in the levels of secreted IL-6 from S. lividans transformants containing either pAE0.aIL6 or pAE0.IL6; however, the secreted IL-6 from S. lividans transformed with pAE0.IL6 appeared to migrate more slowly on the gel than the IL-6 secreted from S. lividans transformed with either pAE0.aIL6 or pAP0.aIL6. Also, there was no detectable IL-6 secretion from the pAP0.IL6 transformant.

The cells which contained the three IL-6 expression vectors were grown in TSB medium as described in Example 15. The proteins that were secreted into the culture supernatant fractions were concentrated by ultrafiltration, separated by SDS-polyacrylamide gel electrophoresis, and transferred to a PVDF membrane as described (Matsudaira, P., 1987, supra). The band containing the IL-6 protein was excised from the membrane and analyzed as described in Example 19. The protein from the pAP0.aIL6 and pAE0.aIL6 transformants had the same amino terminal sequence (XPVPPGEDSK; SEQ ID NO:67), which agreed with the amino terminal sequence of a IL-6. (X indicates a mixture of more than one amino acid was recovered at the first cycle. An alanine residue would be expected at this position.)

However, the amino terminal sequence of the IL-6 that was secreted from the pAE0.IL6 transformant was XXPVP- PGEDS (SEQ ID NO:68), which was one amino acid longer than the IL-6 from the other two vectors and two amino acids longer than the anticipated product. As evidenced by the secretion from pAP0.aIL6 but not pAP0.IL6, the signal peptidase of *S. lividans* seems to be incapable of hydrolysing a peptide bond between alanine and proline residues. The secretion from pAE0.IL6 transformants of an IL-6 protein with two extra amino acids at its amino terminus could be explained by the use of an alternative processing site after -3 in the endo H signal peptide, which could be made possible by the extended (10 amino acid) beta-bend region of the carboxy terminus of the endo H signal peptide, which is not found in the protease signal peptide. Accordingly, the two extra amino acids indicated by XX in the sequence would be serine-alanine.

Transformants of *S. lividans* containing pAP0.aIL6, pAE0.aIL6, or pAE0.IL6 were grown in TSB medium plus thiostrepton, and supernatant fractions were collected following the teaching of Example 15. The harvested supernatant fractions were sterilized by filtration, and the biological activity of the secreted IL-6 was assayed for $^3$H-thymidine incorporation into murine hybridoma B9 cells (Brakenhoff, et al., 1987; Landsdorp, P. M., et al., 1986, Immunol. 132:105). As shown in Table V, culture supernatants of cells containing an IL-6 expression vector had a level of activity corresponding to the estimated level of secreted IL-6 protein. By comparison, no IL-6 activity was observed in control cultures of *S. lividans* transformed with an expression vector lacking the IL-6 gene.

TABLE V

Biological activity of culture supernatants of *S. lividans* transformed with either various IL-6 expression vectors or a negative control vector without the IL-6 gene.

| EXPRESSION VECTOR | TIME (h) | CONCENTRATION OF IL-6* (mg/l) |
|---|---|---|
| pAP0.aIL6 | 16 | 2.9 |
| pAP0.aIL6 | 23 | 12.2 |
| pAE0.aIL6 | 16 | 2.0 |
| pAE0.aIL6 | 23 | 8.0 |
| pAE0.IL6 | 16 | 3.0 |
| pAE0.IL6 | 23 | 14.5 |
| pAP0.control | 19 | <0.0001 |
| pAP0.control | 23 | <0.0001 |

*Estimated concentration of IL-6 determined by activity assay relative to a recombinant IL-6 standard.

EXAMPLE 25

Use of the Streptomyces expression system for secretion of bioactive human erythropoietin ("EPO")

A synthetic DNA sequence was designed by backtranslation of the EPO amino acid sequence (Jacobs, K., et al., 1985, *Nature* 313:806–809), using a codon selection optimized for Streptomyces. This DNA sequence and its reverse complement were used for the synthesis of 16 oligonucleotides which were annealed and ligated together as in Example 7. The completed 0.51-kb synthetic EPO gene was then ligated into the PstI and HindIII sites of pT7T3 19U and used to transform *E. coli*. After screening the transformants by restriction analysis of the plasmid DNA, the synthetic EPO gene was determined to be authentic by DNA sequence analysis. A DNA sequence encoding this EPO gene is presented in FIG. 21 and SEQ ID NO:69, and the amino acid sequence translated from nucleotide 5 through 502 is disclosed in SEQ ID NO:70. The PstI site contained a GCA codon for the alanine at the -1 position, which is compatible with the protease B and endo H expression systems.

Following the teaching of Example 9, the 0.51-kb PstI-HindIII fragment of the resulting plasmid, pT7T3.EPO, containing the EPO gene, was ligated to the NsiI-HindIII vector fragment of pAP0.H, containing the aph promoter and encoding the protease B signal peptide, by using T4 DNA ligase. In the resulting expression vector, pAP0.EPO, the carboxy terminus of the encoded protease B signal peptide is fused directly to the amino terminus of the encoded EPO protein. As taught in Example 10, the same 0.51-kb PstI-HindIII fragment of pT7T3.EPO was also ligated to the PstI-HindIII vector fragment of pAE0.SH, containing the aph promoter and encoding the protease B-endo H hybrid signal peptide, by using T4 DNA ligase. In the resulting expression vector, pAE0.EPO, the carboxy terminus of the encoded protease B-endo H hybrid signal peptide is fused directly to the amino terminus of the encoded EPO protein.

The amino terminal sequence of EPO (APP) is identical to that of the α-amylase from *Streptomyces limosus* (Long, C. M., et al., 1987, *J. Bacteriol.* 169:5745–5754). The positions of prolines in the α-amylase precursor, at -6, -4, +2 and +3 relative to the signal peptide processing site, may be important for the efficient processing of the signal peptide from the mature protein. Thus, to increase the secretion of EPO from Streptomyces, an alternative expression vector was constructed which encoded a modified protease B signal peptide, specifically a 39-amino-acid peptide of the sequence MRIKRTSNRSNAARRVRTTAVLAGLAAVAALAVPTPAAA (SEQ ID NO:71). The specific alterations from the natural protease B signal peptide of this exemplary modified protease B signal peptide are the insertion of a proline between the threonine at -4 and the alanine at -3, and the replacement with an alanine for the asparagine at -2 (positions are numbered leftward from the carboxy terminus of the signal peptide). The modified protease B signal peptide could be equally described as a hybrid signal peptide in which the amino terminal 33 (34 or 35) amino acids of the protease B signal peptide are joined to the carboxy terminal 6 (5 or 4) amino acids of the α-amylase signal peptide.

Construction of an expression vector with the altered protease B signal peptide involved the use of two synthetic oligonucleotides, a 75-mer (SEQ ID NO:72) and a 67-mer (SEQ ID NO:73), encoding the carboxy terminal 25 amino acids of the altered protease B signal peptide (FIG. 22). This amino acid sequence, translated from nucleotides 1 through 75 of SEQ ID NO:72, is disclosed in SEQ ID NO:74. As in Example 12, the synthetic oligonucleotides were annealed and then ligated to the MluI and PstI sites of the expression vector pAEO.SH (FIG. 6). The resulting expression vector pAPz. SH, contained the aph promoter, a sequence encoding the altered protease B signal peptide, and a replaceable synthetic DNA segment.

More specifically, the synthetic oligonucleotides were annealed and then ligated to the MluI and PstI sites of the expression vector pAEO.EPO, containing the aph promoter, and encoding the amino terminal 15 amino acids of the protease B signal peptide, and encoding the EPO protein. Alternatively, the 0.51-kb PstI-HindIII fragment of pT7T3.EPO, containing the EPO gene, was ligated to the PstI-HindIII vector fragments of pAPz. SH, containing the aph promoter and encoding the altered protease B signal peptide, by using T4 DNA ligase. In the resulting expression vector, pAPz.EPO, the carboxy terminus of the encoded altered protease B signal peptide is fused directly to the amino terminus of the encoded EPO protein. The aph promoter of pAPz. EPO was replaced with the agarase promoter following Example 21. In the resulting expression vector, pGPz.EPO, the agarase promoter is joined to a sequence encoding the altered protease B signal peptide which is fused to the EPO protein.

Protoplasts of *S. lividans* 66 were prepared and transformed with the EPO expression vectors (Example 14). Single colonies of the resulting transformants were grown in TSB medium without thiostrepton, and supernatant fractions were collected (Example 15). (Omission of thiostrepton avoids confusing the secreted EPO with a co-migrating thiostrepton-inducible protein.) The proteins that were secreted into the culture supernatant fractions (30 μl aliquots) were analyzed by polyacrylamide gel electrophoresis and Western blotting as in Example 22.

The profile of separated proteins, as visualized by silver staining, shows that a novel protein band was present in the culture supernatants of cells transformed with an EPO expression vector, but was absent in a control culture supernatant of cells containing an expression vector without the EPO gene. The novel protein band migrated with an apparent molecular weight of approximately 20,000 Daltons. Western blot analysis of the proteins separated by gel electrophoresis indicates that the novel protein band found for EPO transformants reacts uniquely with the antibody raised against EPO.

The level of secreted EPO was approximately three times higher from an *S. lividans* transformant containing the protease B signal (pAP0.EPO) than from one containing a protease B-endo H hybrid signal (pAE0.EPO). In addition, the level of secreted EPO was approximately five times higher from an *S. lividans* transformant containing an altered protease B signal (pAPz.EPO) than from one containing pAP0.EPO. A two-fold decrease in secreted EPO was observed when the aph promoter of pAPz.EPO was replaced with the agarase promoter (pGPz.EPO). For control constructions in which the proline at amino acid +3 of EPO was replaced with alanine, both altered and natural protease signal peptides gave the same level of secreted EPO derivative which was equivalent to the level of EPO secreted from cells containing pAPz.EPO. Thus, the proline at amino acid +3 of EPO is relevant to the relatively lower level of secretion observed with the natural protease B signal peptide.

The cells which contained the pAPz.EPO expression vector were grown in TSB medium without thiostrepton, as described in Example 15. The proteins that were secreted into the culture supernatant fractions were concentrated by ultrafiltration, separated by SDS-polyacrylamide gel electrophoresis, and transferred to a PVDF membrane as described (Matsudaira, 1987, supra). The band containing the EPO protein was excised from the membrane and analyzed as described in Example 19. The protein from the pAPz.EPO transformant had an amino terminal sequence of XPPXLIXDSR (SEQ ID NO:75), which agreed with the expected amino terminal sequence of EPO. (X indicates a mixture of more than one amino acid was recovered at a particular cycle.)

Transformants of *S. lividans* containing pAPz.EPO were grown in TSB medium without thiostrepton, and supernatant fractions were collected as in Example 15. The harvested supernatant fractions were sterilized by filtration, and the biological activity of the secreted EPO was assayed for $^3$H-thymidine incorporation into spleen cells from phenylhydrazine treated mice (Krystal, G., 1983, Exp. Hematol. 11:649–660). As shown in Table VI, culture supernatants of cells containing pAPz.EPO had a level of EPO activity corresponding to a few mg/l relative to a recombinant EPO standard. By comparison, no EPO production was observed in control cultures of *S. lividans* transformed with an expression vector lacking the EPO gene.

TABLE VI

Biological activity of culture supernatants of *S. lividans* which was transformed with either pAPz.EPO or a negative control vector without the EPO gene.

| EXPRESSION VECTOR | TIME (h) | CONCENTRATION OF EPO* (mg/l) |
|---|---|---|
| pAPz.EPO | 19 | >2.8 |
| pAPz.EPO | 23 | >2.8 |
| pAP0.control | 19 | <0.0001 |
| pAP0.control | 23 | 0.0001 |

*Estimated concentration of EPO determined by activity assay relative to a recombinant EPO standard.

EXAMPLE 26

Use of the Streptomyces expression system for secretion of bioactive human stem cell factor ("SCF")

A synthetic DNA sequence was designed by reverse translation of the SCF amino acid sequence (Martin, F. H., et al., 1990, *Cell* 63: 203–211) using a codon selection optimized for Streptomyces. This DNA sequence and its reverse complement were used for synthesis of 16 oligonucleotides which were first divided into two centrally overlapping groups (one group comprising the amino terminal ten oligonucleotides, the other group comprising the carboxy terminal eight oligonucleotides), which were each annealed and ligated together according to Example 7. The annealed and ligated groups of oligonucleotides were digested with XhoI, purified by agarose gel electrophoresis and then ligated together into the PstI and HindIII sites of pT7T3 19U, which was used to transform *E. coli*. After screening the transformants by restriction analysis of the plasmid DNA, the synthetic SCF gene was determined to be authentic by DNA sequence analysis. A DNA sequence encoding this SCF gene is presented in FIG. 23 and SEQ ID NO:76, and the amino acid sequence translated from nucleotides 5 to 496 is disclosed in SEQ ID NO:77. The PstI site contained a GCA codon for the alanine at the −1 position, which is compatible with the protease B and endo H expression systems.

As taught in Example 9, the 0.50-kb PstI-HindIII fragment of the resulting plasmid, pT7T3.SCF, containing the SCF gene, was ligated to the NsiI-HindIII vector fragment of pAP0.H, containing the aph promoter and encoding the protease B signal peptide, by using T4 DNA ligase. In the resulting expression vector, pAP0.SCF, the carboxy terminus of the encoded protease B signal peptide is fused directly to the amino terminus of the encoded SCF protein. Following Example 24, the same 0.50-kb PstI-HindIII fragment of pT7T3.SCF was also ligated to the PstI-HindIII vector fragment of pAPz. SH, containing the aph promoter and encoding the altered protease B signal peptide, by using T4 DNA ligase. In the resulting expression vector, pAPz. SCF, the carboxy terminus of the encoded altered protease B signal peptide is fused directly to the amino terminus of the encoded SCF protein. Following the teaching of Example 10, the same 0.50-kb PstI-HindIII fragment of pT7T3.SCF was also ligated to the PstI-HindIII vector fragment of pAE0.SH, containing the aph promoter and encoding the protease B-endo H hybrid signal peptide, by using T4 DNA ligase. In the resulting expression vector, pAE0.EPO, the carboxy terminus of the encoded protease B-endo H hybrid signal peptide is fused directly to the amino terminus of the encoded EPO protein.

An alternative expression vector was constructed which encoded a protease B-streptavidin hybrid signal peptide. A synthetic DNA sequence was designed using the amino acid sequence of the *Streptomyces avidinii* streptavidin signal peptide (Argarana, C. E. et al., 1986, *Nucleic Acids Res.* 14:1871–1882) and the codon usage optimized for Streptomyces. Construction of the protease B-streptavidin hybrid signal peptide expression vector involved the use of two synthetic oligonucleotides, a 72-mer (SEQ ID NO:78) and a 64-mer (SEQ ID NO:79), encoding amino acids 15 through 17 of the protease B signal peptide and the carboxy terminal 21 amino acids of the streptavidin signal peptide (FIG. 24). This amino acid sequence, translated from nucleotides 1 through 72 of SEQ ID NO:78, is disclosed in SEQ ID NO:80. This exemplary hybrid signal has the amino acid sequence disclosed in SEQ ID NO:81. More generally, the amino acid sequence of a protease B-streptavidin hybrid signal peptide of this invention is selected to improve the processing of the SCF protein from the signal peptide, since both SCF and streptavidin have an amino terminal acidic amino acid.

According to Example 12, the MluI-PstI fragment of pAE0.SH was replaced with the annealed synthetic oligonucleotides to construct the expression vector pAS0.SH. As in Example 10, the same 0.50-kb PstI-HindIII fragment of T7T3.SCF was also ligated to the PstI-HindIII vector fragment of pAS0.SH, containing the aph promoter and encoding the protease B-streptavidin hybrid signal peptide, by using T4 DNA ligase. In the resulting expression vector, pAS0.SCF, the carboxy terminus of the encoded protease B-streptavidin hybrid signal peptide is fused directly to the amino terminus of the encoded SCF protein.

Protoplasts of *S. lividans* 66 were prepared and transformed with the SCF expression vectors (Example 14). Single colonies of the resulting transformants were grown in TSB medium without thiostrepton, and supernatant fractions were collected (Example 15). The proteins that were secreted into the culture supernatant fractions (15 μl aliquots) were analyzed by polyacrylamide gel electrophoresis (Example 22). The profile of separated proteins, as visualized by silver staining, shows that a novel protein band was present in the culture supernatants of cells transformed with an SCF expression vector, but was absent in a supernatants from control cultures of cells containing an expression vector without the SCF gene.

The novel protein band from 18-hour culture supernatants migrated with an apparent molecular weight of approximately 18,000 Daltons. However, after 24 hours of culture a faster-migrating protein had appeared, which by 30 hours had replaced the 18,000 Dalton protein. To investigate the structures of these two proteins, the amino terminal sequences were analyzed. *S. lividans* which contained the pAPz.SCF expression vector were grown in TSB medium for 18 h and 30 h (Example 15). The proteins that were secreted into the culture supernatant fractions were concentrated by ultrafiltration, separated by SDS-polyacrylamide gel electrophoresis, and transferred to a PVDF membrane as described (Matsudaira, 1987, supra). The bands containing the proteins were excised from the membrane and analyzed (Example 19).

The protein which was present in the 18 h culture supernatant of the pAPz. SCF transformant had an amino terminal sequence of XGIXXNXVTN (SEQ ID NO:82), which agrees with he expected amino terminal sequence of SCF. However, the faster-migrating protein from the 30 h culture supernatant had the same amino terminal sequence. Thus the smaller form of SCF in later cultures appeared to be truncated at the carboxy terminus. Based upon the previous example with IL-3S, the most probable processing site is SS↓T, which is situated between domains of SCF.

The highest level of secreted SCF was observed from *S. lividans* transformants containing either the altered protease B signal (pAPz. SCF) or the hybrid protease B-endo H signal (pAE0.SCF). The level of secreted SCF was approximately five times lower from *S. lividans* transformants containing either the protease B signal (pAP0.EPO) or the protease B-streptavidin hybrid signal (pAS0.SCF). The culture supernatant of pAE0.SCF also contained an additional novel protein which migrated more slowly than 18,000 Daltons. A similar situation was observed with pAE0.IL6 (Example 24), in which an alternative processing site within the endo H signal peptide was utilized, resulting in secreted protein with an additional two amino acids at the amino terminus.

Transformants of *S. lividans* containing pAPz. SCF were grown in TSB medium without thiostrepton, and supernatant fractions were collected (Example 15). The harvested supernatant fractions were sterilized by filtration, and biological activity of the secreted SCF was determined by the ability to colonize bone marrow cells in culture. Mononuclear cells were purified from human bone marrow by density centrifugation. Approximately $10^5$ mononuclear cells were plated in 4 ml of medium containing 0.8% methylcellulose, 20% human plasma, 10% fetal calf serum, 0.05 mM 2-mercaptoethanol, and the appropriate SCF or control sample. Triplicate cultures for each growth condition were incubated for 12–14 days at 37° C. in a 5% $CO_2$ atmosphere. Colonies were then scored in situ under a microscope.

As shown in Table VII, culture supernatants of *S. lividans* containing pAPz.SCF had significant levels of granulocyte/macrophage colony forming units (CFU-GM), comparable to that observed with a standard preparation of SCF produced in mammalian cell culture. Levels of CFU-GM were similar from cultures harvested at either 18 or 30 h, indicating that the carboxy terminally truncated form of SCF is equally active. By comparison, no significant activity was observed in control cultures of *S. lividans* transformed with an expression vector lacking the SCF gene. However, the level of erythrocyte-burst forming units (BFU-E) was substantially lower for SCF from *S. lividans* than for the SCF standard.

TABLE VII

Colony stimulating activity of supernatants of *S. lividans* transformed with pAPz.SCF or a negative control vector without the SCF gene.

| Sample | Time (h) | Stimulated Colonies per $10^5$ Cells | |
|---|---|---|---|
| | | CFU-GM[1] | BFU-E[2] |
| pAPz.SCF | 18 | 71 | 5 |
| pAPz.SCF | 30 | 69 | 4 |
| pAP0.Control | 19 | 7 | 0 |
| No addition | N/A[3] | 8 | 0 |
| Human SCF (Cytomed) | N/A[3] | 83 | 150 |

[1]Colony Forming Units - Granulocyte Macrophage
[2]Burst Forming Units - Erythroid
[3]Not applicable

EXAMPLE 27

Use of the Streptomyces expression system for secretion of bioactive human interleukin-7 ("IL-7")

A synthetic DNA sequence was designed by reverse translation of the IL-7 amino acid sequence (Goodwin, R. G., et al., 1989, Proc. Natl. Acad. Sci. USA 86:302–306) using a codon selection optimized for Streptomyces. This DNA sequence and its reverse complement were used for synthesis of 15 oligonucleotides which were annealed and ligated together (Example 7). The completed 0.47-kb IL-7 gene was then ligated into the PstI and HindIII sites of pT7T3 19U, which was used to transform E. coli. After screening the transformants by restriction analysis of the plasmid DNA, the synthetic IL-7 gene was determined to be authentic by DNA sequence analysis. A DNA sequence encoding this IL-7 gene is presented in FIG. 25 and SEQ ID NO:83, and the amino acid sequence translated from nucleotides 5 to 460 is disclosed in SEQ ID NO:84. The PstI site contained a GCA codon for the alanine at the −1 position, which is compatible with the protease B and endo H expression systems.

As in Example 9, the 0.47-kb PstI-HindIII fragment of the resulting plasmid, pT7T3.IL7, containing the IL-7 gene, was ligated to the NsiI-HindIII vector fragment of pAP0.H, containing the aph promoter and encoding the protease B signal peptide. In the resulting expression vector, pAP0.IL7, the carboxy terminus of the encoded protease B signal peptide is fused directly to the amino terminus of the encoded IL-7 protein. As in Example 24, the same 0.47-kb PstI-HindIII fragment of pT7T3.IL7 was also ligated to the PstI-HindIII vector fragment of pAPz.H, containing the aph promoter and encoding the altered protease B signal peptide. In the resulting expression vector, pAPz.IL7, the carboxy terminus of the encoded altered protease B signal peptide is fused directly to the amino terminus of the encoded IL-7 protein. As in Example 10, the same 0.47-kb PstI-HindIII fragment of T7T3.IL7 was also ligated to the PstI-HindIII vector fragment of pAE0.SH, containing the aph promoter and encoding the protease B-endo H hybrid signal peptide, by using T4 DNA ligase. In the resulting expression vector, pAE0.IL7, the carboxy terminus of the encoded protease B-endo H hybrid signal peptide is fused directly to the amino terminus of the encoded IL-7 protein. As in Example 26, the same 0.47-kb PstI-HindIII fragment of pT7T3.IL7 was also ligated to the PstI-HindIII vector fragment of pAS0.SH, containing the aph promoter and encoding the protease B-streptavidin hybrid signal peptide. In the resulting expression vector, pAS0.IL7, the carboxy terminus of the encoded protease B-streptavidin hybrid signal peptide is fused directly to the amino terminus of the encoded IL-7 protein.

Protoplasts of S. lividans 66 were prepared and transformed with the IL-7 expression vectors (Example 14). Single colonies of the resulting transformants were grown in TSB medium without thiostrepton, and supernatant fractions were collected (Example 15). The proteins that were secreted into the culture supernatant fractions (30 µl aliquots) were analyzed by polyacrylamide gel electrophoresis (Example 22). The profile of separated proteins shows that a novel protein band was present in the culture supernatants of cells transformed with an IL-7 expression vector, but was absent in a supernatants from control cultures of cells containing an expression vector without the IL-7 gene. Western blot analysis of the proteins separated by gel electrophoresis indicates that the novel protein band found for IL-7 transformants reacts uniquely with the antibody raised against IL-7.

The highest level of secreted IL-7 was observed from S. lividans transformants containing either the altered protease B signal (pAPz.IL7) or the protease B-endo H hybrid signal (pAE0.IL7). The level of secreted SCF was approximately five times lower from S. lividans transformants containing either the protease B signal (pAP0.IL7) or the protease B-streptavidin hybrid signal (pAS0.IL7). The novel protein band present in the culture supernatant of S. lividans containing pAE0.IL7 migrated slower than 17,000 Daltons. A similar situation was observed with pAE0.IL6 (Example 24), in which an alternative processing site within the endo H signal peptide was utilized, resulting in a secreted protein with an additional two amino acids at the amino terminus.

The increases in the levels of secretion of both IL-7 and SCF resulting from the use of the altered protease B signal peptide compared with the natural protease B signal peptide cannot be due to the positions of prolines, since neither IL-7 nor SCF have prolines in their amino termini. The explanation for the increase in secretion may be due to the positions of the first disulfide bond in each protein. Cysteins which are involved in disulfide bonds are located at amino acid numbers +2 for IL-7, +4 for SCF and +7 for EPO. On this basis the altered protease B signal peptide may be more efficient than the natural protease B signal peptide for other proteins which have disulfide bonds involving cysteines near the amino terminus. In general, the altered protease B signal peptide may be useful for secreting a protein which has a structure that constrains the conformation near the amino terminus of the mature protein.

EXAMPLE 28

Use of the Streptomyces expression system for secretion of bioactive human tumour necrosis factor alpha ("TNFα")

A synthetic DNA sequence was designed by backtranslation of the TNFα amino acid sequence (Pennica, D., et al., 1984, Nature 312:724–729), using a codon selection for Streptomyces. This DNA sequence and its reverse complement were used for the synthesis of 16 oligonucleotides which were annealed and ligated together (Example 7). The completed 0.48-kb synthetic TNFα gene was then ligated into the PstI and XbaI sites of pUC18 and used to transform E. coli. After screening the transformants by restriction analysis of the plasmid DNA, the synthetic TNFα gene was determined to be authentic by DNA sequence analysis. A DNA sequence encoding this TNFα gene is presented in FIG. 26 and SEQ ID NO:85, and the amino acid sequence translated from nucleotides 5 through 475 is disclosed in SEQ ID NO:86. The PstI site contained a GCA codon for the alanine at the −1 position, which is compatible with the protease B and endo H expression systems.

The 0.48-kb PstI-XbaI fragment of the resulting plasmid, pUC.TNFα, containing the TNFα gene, was ligated to the PstI-XbaI vector fragment of pAE0.SX, containing the aph promoter and encoding the protease B-endo H hybrid signal peptide. In the resulting expression vector, pAE0.TNFα, the carboxy terminus of the encoded protease B-endo H hybrid signal peptide is fused directly to the amino terminus of the encoded TNFα protein. The same 0.48-kb PstI-XbaI fragment of pUC.TNFα was also ligated to the NsiI-XbaI vector fragment of pAE0.G, containing the aph promoter and encoding the protease B signal peptide. In the resulting expression vector, pAP0.TNFα, the carboxy terminus of the encoded protease B signal peptide is fused directly to the amino terminus of the encoded TNFα protein. The aph promoter of pAE0.TNFα was replaced with the agarase promoter (Example 21). In the resulting expression vector, pGE0.TNFα, the agarase promoter is joined to a sequence encoding the protease B signal peptide which is fused to the TNFα protein.

Protoplasts of *S. lividans* 66 were prepared and transformed with the TNFα expression vectors (Example 14). The resulting transformants were grown in liquid culture, and supernatant fractions were collected (Example 15). The proteins that were secreted into the culture supernatant fractions were concentrated by TCA precipitation and analyzed by polyacrylamide gel electrophoresis (Example 16). The profile of separated proteins, as visualized by staining with Coomassie Brilliant Blue shows that a novel protein band was present in the culture supernatants of cells transformed with a TNFα expression vector, but was absent in a control culture supernatant of cells containing an expression vector without the TNFα gene. The novel protein band migrated with an apparent molecular weight of approximately 17,000 Daltons.

Western blot analysis of the proteins separated by gel electrophoresis indicates that the novel protein band found for TNFα transformants reacts uniquely with the antibody raised against TNFα. The levels of secreted TNFα were approximately five times higher from the *S. lividans* transformants containing pAE0.TNFα than from those containing pAP0.TNFα. There was no significant difference in the levels of secreted TNFα from the *S. lividans* transformants containing either pAE0.TNFα or pGE0.TNFα.

The cells which contained the pAE0.TNFα expression vector were grown (Example 15). The proteins that were secreted into the culture supernatant fractions were purified (Example 18) and analyzed (Example 19). The protein from the pAE0.TNFα transformant had an amino terminal sequence of SRTPSDKPVA (SEQ ID NO:87), which agreed with the expected amino acid sequence of TNFα from positions 5 to 14.

Transformants of *S. lividans* containing either pAP0.TNFα or pAE0.TNFα were grown in liquid medium, and supernatant fractions were collected (Example 15). The harvested supernatant fractions were sterilized by filtration, and the biological activity of the secreted TNFα was assayed for cytolytic activity on mouse L-929 fibroblasts as described (Aggarwal, B., et al., 1984, *J. Biol. Chem.* 259:686–691). One unit of TNFα is defined as the amount required to give 50% cell lysis. As shown in Table VIII, culture supernatants of cells containing a TNFα expression vector had a level of activity corresponding to the estimated level of secreted TNFα protein. By comparison, no TNFα activity was observed in control cultures of *S. lividans* transformed with an expression vector lacking the TNFα gene.

TABLE VIII

Cytotoxic activity of culture supernatants of *S. lividans* which was tranformed with either pAE0.TNFα, pAP0.TNFα, or a negative control vector containing a different gene.

| EXPRESSION VECTOR | TIME (h) | TNF ACTIVITY (U/ml) |
|---|---|---|
| pAP0.TNFα | 28 | 128 |
| pAP0.TNFα | 32 | 64 |
| pAP0.TNFα | 45 | 3000 |
| pAE0.TNFα | 28 | 190 |
| pAE0.TNFα | 32 | 4000 |
| pAE0.TNFα | 45 | 256 |
| pAP0.control | 28 | <4 |
| pAP0.control | 45 | <4 |
| 25 ng recombinant human TNFα | | 2500 |

EXAMPLE 29

Use of the Streptomyces expression system for secretion of bioactive human interleukin-2 ( "IL-2")

A synthetic DNA sequence was designed by backtranslation of the IL-2 amino acid sequence (Taniguchi, T., et al., 1983, *Nature* 302:305–310), using a codon selection optimized for Streptomyces. This DNA sequence and its reverse complement were used for the synthesis of 12 oligonucleotides which were annealed and ligated together (Example 7). The completed 0.41-kb synthetic IL-2 gene was then ligated into the PstI and HindIII sites of pUC18 and used to transform *E. coli*. After screening the transformants by restriction analysis of the plasmid DNA, the synthetic IL-2 gene was determined to be authentic by DNA sequence analysis. A DNA sequence encoding this IL-2 gene is presented in FIG. 27 and SEQ ID NO:88, and the amino acid sequence translated from nucleotides 5 through 403 is disclosed in SEQ ID NO:89. The PstI site contained a GCA codon for the alanine at the −1 position, which is compatible with the protease B and endo H expression systems.

The 0.41-kb PstI-HindIII fragment of the resulting plasmid, pUC.IL2, containing the IL-2 gene, was ligated to the PstI-HindIII vector fragment of pAE0.SH, containing the aph promoter and encoding the protease B-endo H hybrid signal peptide. In the resulting expression vector, pAE0.IL2, the carboxy terminus of the encoded protease B-endo H hybrid signal peptide is fused directly to the amino terminus of the encoded IL-2 protein. The same 0.41-kb PstI-HindIII fragment of pUC.IL2 was also ligated to the NsiI-HindIII vector fragment of pAP0.H, containing the aph promoter and encoding the protease B signal peptide. In the resulting expression vector, pAP0.IL2, the carboxy terminus of the encoded protease B signal peptide is fused directly to the amino terminus of the encoded IL-2 protein. The amino terminus of the signal peptide in pAE0.IL2 was changed from protease B to endo H (Example 11). In the resulting expression vector, pAE0-1.IL2, the encoded endo H signal peptide is fused directly to the amino terminus of the encoded IL-2 protein.

Protoplasts of *S. lividans* 66 were prepared and transformed with the IL-2 expression vectors (Example 14). The resulting transformants were grown in liquid culture, and supernatant fractions were collected (Example 15). The proteins that were secreted into the culture supernatant fractions were concentrated by TCA precipitation and analyzed by polyacrylamide gel electrophoresis (Example 16). The profile of separated proteins, as visualized by staining with Coomassie Brilliant Blue, shows that a novel protein band was present in the culture supernatants of cells transformed with a IL-2 expression vector, but was absent in a control culture supernatant of cells containing an expression vector without the IL-2 gene. The novel protein band, in lanes 1 to 3, migrated with an apparent molecular weight of approximately 15,000 Daltons, and comigrated with a recombinant IL-2 standard.

Western blot analysis of the proteins separated by gel electrophoresis indicated that the novel protein band found for IL-2 transformants reacts uniquely with the antibody raised against IL-2. The levels of secreted IL-2 were approximately four times higher from the *S. lividans* transformants containing pAE0.IL2 than from those containing pAE0-1.IL2.

The cells which contained the pAE0.IL2 expression vector were grown (Example 15). The proteins that were secreted into the culture supernatant fractions were purified (Example 18) and analyzed (Example 19). The protein from the pAE0.IL2 transformant had an amino terminal sequence of APTSSSTKKT (SEQ ID NO:90), which agreed with the expected amino terminal sequence of IL-2.

Transformants of *S. lividans* containing either pAE0.IL2 or pAE0-1.IL2 were grown in liquid medium, and supernatant fractions were collected (Example 15). The harvested supernatant fractions were sterilized by filtration, and the biological activity of the secreted IL-2 was assayed for proliferation of MTL2.82 cells as described (Bleakley, R. C., et al., 1982, *J. Immunol.* 128:758–767). As shown in Table IX, culture supernatants of cells containing an IL-2 expression vector had a level of activity corresponding to the estimated level of secreted IL-2 protein. By comparison, no IL-2 activity was observed in control cultures of *S. lividans* transformed with an expression vector lacking the IL-2 gene.

TABLE IX

Cell proliferation activity of culture supernatants of *S. lividans* which was transformed with either pAE0.IL2, pAE0.IL2-1, or a negative control vector containing a different gene.

| EXPRESSION VECTOR | TIME (h) | IL-2 ACTIVITY (U/ml) |
|---|---|---|
| pAE0.IL2 | 22 | 2200 |
| pAE0.IL2 | 33 | 1500 |

TABLE IX-continued

Cell proliferation activity of culture supernatants of *S. lividans* which was transformed with either pAE0.IL2, pAE0.IL2-1, or a negative control vector containing a different gene.

| EXPRESSION VECTOR | TIME (h) | IL-2 ACTIVITY (U/ml) |
|---|---|---|
| pAE0.1.IL2 | 28 | 600 |
| pAE0.1.IL2 | 33 | 150 |
| pAP0.control | 28 | 0 |
| pAP0.control | 34 | 0 |
| 500 ng recombinant human IL-2 | | 5000. |

Although preferred embodiments of the invention have been described in detail, it will be understood by those skilled in the art that variations may be made to the preferred embodiments without departing from either the spirit of the invention or the scope of the appended claims.

What is claimed is:

1. A gene expression system comprising a regulatory polynucleotide molecule that is operatively linked to a second polynucleotide molecule encoding a eucaryotic protein, wherein
   (A) said regulatory polynucleotide molecule comprises
       (i) a promoter polynucleotide molecule and
       (ii) a signal polynucleotide molecule encoding a signal peptide capable of directing secretion of eucaryotic protein in bioactive form from a host selected from the genus Streptomyces;
   (B) said signal peptide comprises a 15-mer of *Streptomyces griseus* protease B, MRIKRTSNRSNAARR; and
   (C) wherein said promoter polynucleotide molecule is operably linked to said signal polynucleotide molecule.

2. A gene expression system according to claim 1, wherein said eukaryotic protein is selected from the group consisting of: interleukin-3 (IL-3), interleukin-6 (IL-6), tumor necrosis factor alpha (TNFα), human stem cell factor (SCF), interleukin-7 (IL-7), erythropoietin (EPO) and interleukin-2 (IL-2).

3. A gene expression system according to claim 1, wherein said eukaryotic protein is granulocyte macrophage colony stimulating factor (GM-CSF).

4. A gene expression system according to claim 1, wherein said signal peptide is *Streptomyces griseus* altered protease B, MRIKRTSNRSNAARRVRTTAVLAG-LAAVAALAVPTPAAA.

5. A gene expression system according to claim 4, wherein said eukaryotic protein is selected from the group consisting of: interleukin-3 (IL-3), interleukin-6 (IL-6), tumor necrosis factor alpha (TNFα), human stem cell factor (SCF), interleukin-7 (IL-7), erythropoietin (EPO) and interleukin-2 (IL-2).

6. A gene expression system according to claim 4, wherein said eukaryotic protein is granulocyte macrophage colony stimulating factor (GM-CSF).

7. A gene expression system according to claim 1, wherein said signal peptide is *Streptomyces griseus* protease B, MRIKRTSNRSNAARRVRTTAVLAG-LAAVAALAVPTANA.

8. A gene expression system according to claim 7, wherein said eukaryotic protein is selected from the group consisting of: interleukin-3 (IL-3), interleukin-6 (IL-6), tumor necrosis factor alpha (TNFα), human stem cell factor (SCF), interleukin-7 (IL-7), erythropoietin (EPO) and interleukin-2 (IL-2).

9. A gene expression system according to claim 7, wherein said eukaryotic protein is granulocyte macrophage colony stimulating factor (GM-CSF).

* * * * *

SEQUENCE LISTING ( 1 ) GENERAL INFORMATION:

( i i i ) NUMBER OF SEQUENCES: 91

( 2 ) INFORMATION FOR SEQ ID NO:1:

( i ) SEQUENCE CHARACTERISTICS:
        ( A ) LENGTH: 392 base pairs
        ( B ) TYPE: nucleic acid
        ( C ) STRANDEDNESS: double
        ( D ) TOPOLOGY: linear ( i i ) MOLECULE TYPE: Other nucleic acid;
        ( A ) DESCRIPTION: Synthetic DNA oligonucleotide ( i x ) FEATURE:
        ( A ) NAME/KEY: CDS
        ( B ) LOCATION: 5..385

( x i ) SEQUENCE DESCRIPTION: SEQ ID NO:1:

```
TGCA GCC CCC GCC CGG TCG CCC TCG CCG TCG ACC CAG CCG TGG GAG CAC        49
     Ala Pro Ala Arg Ser Pro Ser Pro Ser Thr Gln Pro Trp Glu His
     1               5                   10                  15

GTC AAC GCG ATC CAG GAG GCC CGC CGC CTG CTC AAC CTC TCG CGG GAC         97
Val Asn Ala Ile Gln Glu Ala Arg Arg Leu Leu Asn Leu Ser Arg Asp
                    20                  25                  30

ACG GCC GCC GAG ATG AAC GAG ACC GTG GAG GTG ATC TCG GAG ATG TTC        145
Thr Ala Ala Glu Met Asn Glu Thr Val Glu Val Ile Ser Glu Met Phe
                35                  40                  45

GAC TTG CAG GAG CCC ACG TGC CTC CAG ACC CGC CTC GAG CTG TAC AAG        193
Asp Leu Gln Glu Pro Thr Cys Leu Gln Thr Arg Leu Glu Leu Tyr Lys
            50                  55                  60

CAG GGG CTC CGG GGC AGC CTC ACC AAG CTC AAG GGG CCG CTG ACC ATG        241
Gln Gly Leu Arg Gly Ser Leu Thr Lys Leu Lys Gly Pro Leu Thr Met
        65                  70                  75

ATG GCG TCC CAC TAC AAA CAG CAC TGC CCC CCC ACG CCG GAG ACG TCG        289
```

|   |   |   |   |   |   |   |   |   |   |   |   |   |   |   |   |     |
|---|---|---|---|---|---|---|---|---|---|---|---|---|---|---|---|-----|
| Met | Ala | Ser | His | Tyr | Lys | Gln | His | Cys | Pro | Pro | Thr | Pro | Glu | Thr | Ser | |
| 80 |   |   |   |   | 85 |   |   |   | 90 |   |   |   |   |   | 95 | |
| TGC | GCC | ACC | CAG | ATC | ATC | ACG | TTC | GAG | TCG | TTC | AAG | GAG | AAC | CTG | AAG | 337 |
| Cys | Ala | Thr | Gln | Ile | Ile | Thr | Phe | Glu | Ser | Phe | Lys | Glu | Asn | Leu | Lys | |
|   |   |   |   | 100 |   |   |   |   | 105 |   |   |   |   | 110 |   | |
| GAC | TTC | CTC | CTC | GTG | ATC | CCC | TTC | GAC | TGC | TGG | GAG | CCG | GTG | CAG | GAG | 385 |
| Asp | Phe | Leu | Leu | Val | Ile | Pro | Phe | Asp | Cys | Trp | Glu | Pro | Val | Gln | Glu | |
|   |   |   | 115 |   |   |   |   | 120 |   |   |   |   | 125 |   |   | |
| TGAAGCT |   |   |   |   |   |   |   |   |   |   |   |   |   |   |   | 392 |

( 2 ) INFORMATION FOR SEQ ID NO:2:

( i ) SEQUENCE CHARACTERISTICS:
        ( A ) LENGTH: 127 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Ala | Pro | Ala | Arg | Ser | Pro | Ser | Pro | Ser | Thr | Gln | Pro | Trp | Glu | His | Val |
|---|---|---|---|---|---|---|---|---|---|---|---|---|---|---|---|
| 1 |   |   |   | 5 |   |   |   |   | 10 |   |   |   |   |   | 15 |

| Asn | Ala | Ile | Gln | Glu | Ala | Arg | Arg | Leu | Leu | Asn | Leu | Ser | Arg | Asp | Thr |
|---|---|---|---|---|---|---|---|---|---|---|---|---|---|---|---|
|   |   |   |   | 20 |   |   |   |   | 25 |   |   |   |   | 30 |   |

| Ala | Ala | Glu | Met | Asn | Glu | Thr | Val | Glu | Val | Ile | Ser | Glu | Met | Phe | Asp |
|---|---|---|---|---|---|---|---|---|---|---|---|---|---|---|---|
|   |   |   | 35 |   |   |   |   | 40 |   |   |   |   | 45 |   |   |

| Leu | Gln | Glu | Pro | Thr | Cys | Leu | Gln | Thr | Arg | Leu | Glu | Leu | Tyr | Lys | Gln |
|---|---|---|---|---|---|---|---|---|---|---|---|---|---|---|---|
|   | 50 |   |   |   |   | 55 |   |   |   |   | 60 |   |   |   |   |

| Gly | Leu | Arg | Gly | Ser | Leu | Thr | Lys | Leu | Lys | Gly | Pro | Leu | Thr | Met | Met |
|---|---|---|---|---|---|---|---|---|---|---|---|---|---|---|---|
| 65 |   |   |   |   | 70 |   |   |   |   | 75 |   |   |   |   | 80 |

| Ala | Ser | His | Tyr | Lys | Gln | His | Cys | Pro | Pro | Thr | Pro | Glu | Thr | Ser | Cys |
|---|---|---|---|---|---|---|---|---|---|---|---|---|---|---|---|
|   |   |   |   | 85 |   |   |   |   | 90 |   |   |   |   | 95 |   |

| Ala | Thr | Gln | Ile | Ile | Thr | Phe | Glu | Ser | Phe | Lys | Glu | Asn | Leu | Lys | Asp |
|---|---|---|---|---|---|---|---|---|---|---|---|---|---|---|---|
|   |   |   |   | 100 |   |   |   |   | 105 |   |   |   |   | 110 |   |

| Phe | Leu | Leu | Val | Ile | Pro | Phe | Asp | Cys | Trp | Glu | Pro | Val | Gln | Glu |
|---|---|---|---|---|---|---|---|---|---|---|---|---|---|---|
|   |   | 115 |   |   |   |   | 120 |   |   |   |   | 125 |   |   |

( 2 ) INFORMATION FOR SEQ ID NO:3:

( i ) SEQUENCE CHARACTERISTICS:
        ( A ) LENGTH: 38 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

| Met | Arg | Ile | Lys | Arg | Thr | Ser | Asn | Arg | Ser | Asn | Ala | Ala | Arg | Arg | Val |
|---|---|---|---|---|---|---|---|---|---|---|---|---|---|---|---|
| 1 |   |   |   | 5 |   |   |   |   | 10 |   |   |   |   | 15 |   |

| Arg | Thr | Thr | Ala | Val | Leu | Ala | Gly | Leu | Ala | Ala | Val | Ala | Ala | Leu | Ala |
|---|---|---|---|---|---|---|---|---|---|---|---|---|---|---|---|
|   |   |   | 20 |   |   |   |   | 25 |   |   |   |   | 30 |   |   |

| Val | Pro | Thr | Ala | Asn | Ala |
|---|---|---|---|---|---|
|   |   | 35 |   |   |   |

( 2 ) INFORMATION FOR SEQ ID NO:4:

( i ) SEQUENCE CHARACTERISTICS:
        ( A ) LENGTH: 41 amino acids
        ( B ) TYPE: amino acid
        ( D ) TOPOLOGY: linear ( i i ) MOLECULE TYPE: peptide (xi) SEQUENCE DESCRIPTION: SEQ ID NO:4:

| Met | Arg | Ile | Lys | Arg | Thr | Ser | Asn | Arg | Ser | Asn | Ala | Ala | Arg | Arg | Val |
| 1 | | | | 5 | | | | | 10 | | | | | | 15 |

| Arg | Thr | Ala | Ala | Leu | Ala | Leu | Ser | Ala | Ala | Ala | Ala | Leu | Val | Leu | Gly |
| | | | 20 | | | | | 25 | | | | | 30 | | |

| Ser | Thr | Ala | Ala | Ser | Gly | Ala | Ser | Ala |
| | | | 35 | | | | | 40 |

(2) INFORMATION FOR SEQ ID NO:5:

(i) SEQUENCE CHARACTERISTICS:
        (A) LENGTH: 34 amino acids
        (B) TYPE: amino acid
        (D) TOPOLOGY: linear (ii) MOLECULE TYPE: peptide (xi) SEQUENCE DESCRIPTION: SEQ ID NO:5:

| Met | Phe | Thr | Pro | Val | Arg | Arg | Arg | Val | Arg | Thr | Ala | Ala | Leu | Ala | Leu |
| 1 | | | | 5 | | | | | 10 | | | | | | 15 |

| Ser | Ala | Ala | Ala | Ala | Leu | Val | Leu | Gly | Ser | Thr | Ala | Ala | Ser | Gly | Ala |
| | | | 20 | | | | | 25 | | | | | 30 | | |

| Ser | Ala |

(2) INFORMATION FOR SEQ ID NO:6:

(i) SEQUENCE CHARACTERISTICS:
        (A) LENGTH: 40 amino acids
        (B) TYPE: amino acid
        (D) TOPOLOGY: linear (ii) MOLECULE TYPE: peptide (xi) SEQUENCE DESCRIPTION: SEQ ID NO:6:

| Met | Arg | Ile | Lys | Arg | Thr | Ser | Asn | Arg | Ser | Asn | Ala | Ala | Arg | Arg | Val |
| 1 | | | | 5 | | | | | 10 | | | | | | 15 |

| Trp | Ile | Ser | Leu | Leu | Phe | Ala | Leu | Ala | Leu | Ile | Phe | Thr | Met | Ala | Phe |
| | | | 20 | | | | | 25 | | | | | 30 | | |

| Gly | Ser | Thr | Ser | Ser | Ala | Gln | Ala |
| | | 35 | | | | | 40 |

(2) INFORMATION FOR SEQ ID NO:7:

(i) SEQUENCE CHARACTERISTICS:
        (A) LENGTH: 900 base pairs
        (B) TYPE: nucleic acid
        (C) STRANDEDNESS: double
        (D) TOPOLOGY: linear (ii) MOLECULE TYPE: Other nucleic acid;
        (A) DESCRIPTION: Synthetic DNA oligonucleotide (ix) FEATURE:
        (A) NAME/KEY: CDS
        (B) LOCATION: 399..893

(xi) SEQUENCE DESCRIPTION: SEQ ID NO:7:

```
GATCCGGCCG TTTCCCGCGC CGCCCGCGCC CACGTGGCGC GGTGGGGGAT TCCGGCCGAA    60
CGCGCCGACG CCCATGTGAC CGCCTGCGTG CTGCGCGGCG CCCGCGCCGC AGGCTCGCCG   120
GGGCGGACCC GGACCCGGCC GCCGAGGTCC TCGCCGCCGA CCGGGAGGCG TGCGGCCTCG   180
CCGCGAGACC GCCGTCCTGC TGCGGCTCAC GGAGGCGTAC CTCTCGCCCT GCGCGCGGGC   240
CCTCGACCCC GCCGGGACCT CCGGCACCGG GCCCGCGGGC GACGCCGGGC GCACCGGGTC   300
```

```
CGCCGGCGCC CCCCCACCCC GCACAAGAAT GTCCGAAACC CTACGGGCCC CGACGAAAGG         360
CGCGGAACGG CGTCTCCGCC TCTGCCATGA TGCCGCCC ATG AGG ATC AAG CGC             413
                                          Met Arg Ile Lys Arg
                                           1               5

ACC AGC AAC CGC TCG AAC GCG GCG AGA CGC GTC CGC ACC ACC GCC GTA           461
Thr Ser Asn Arg Ser Asn Ala Ala Arg Arg Val Arg Thr Thr Ala Val
                10              15                  20

CTC GCG GGG CTC GCC GCC GTC GCG GCG CTG GCC GTT CCC ACC GCC AAT           509
Leu Ala Gly Leu Ala Ala Val Ala Ala Leu Ala Val Pro Thr Ala Asn
            25              30              35

GCA GCC CCC GCC CGG TCG CCC TCG CCG TCG ACC CAG CCG TGG GAG CAC           557
Ala Ala Pro Ala Arg Ser Pro Ser Pro Ser Thr Gln Pro Trp Glu His
        40              45              50

GTC AAC GCG ATC CAG GAG GCC CGC CGC CTG CTC AAC CTC TCG CGG GAC           605
Val Asn Ala Ile Gln Glu Ala Arg Arg Leu Leu Asn Leu Ser Arg Asp
    55              60              65

ACG GCC GCC GAG ATG AAC GAG ACC GTG GAG GTG ATC TCG GAG ATG TTC           653
Thr Ala Ala Glu Met Asn Glu Thr Val Glu Val Ile Ser Glu Met Phe
70              75              80                          85

GAC TTG CAG GAG CCC ACG TGC CTC CAG ACC CGC CTC GAG CTG TAC AAG           701
Asp Leu Gln Glu Pro Thr Cys Leu Gln Thr Arg Leu Glu Leu Tyr Lys
            90              95                  100

CAG GGG CTC CGG GGC AGC CTC ACC AAG CTC AAG GGG CCG CTG ACC ATG           749
Gln Gly Leu Arg Gly Ser Leu Thr Lys Leu Lys Gly Pro Leu Thr Met
        105             110             115

ATG GCG TCC CAC TAC AAA CAG CAC TGC CCC CCG ACG CCG GAG ACG TCG           797
Met Ala Ser His Tyr Lys Gln His Cys Pro Pro Thr Pro Glu Thr Ser
        120             125             130

TGC GCC ACC CAG ATC ATC ACG TTC GAG TCG TTC AAG GAG AAC CTG AAG           845
Cys Ala Thr Gln Ile Ile Thr Phe Glu Ser Phe Lys Glu Asn Leu Lys
    135             140             145

GAC TTC CTC CTC GTG ATC CCC TTC GAC TGC TGG GAG CCG GTG CAG GAG           893
Asp Phe Leu Leu Val Ile Pro Phe Asp Cys Trp Glu Pro Val Gln Glu
150             155             160                         165

TGAAGCT                                                                   900
```

( 2 ) INFORMATION FOR SEQ ID NO:8:

( i ) SEQUENCE CHARACTERISTICS:
        ( A ) LENGTH: 165 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met Arg Ile Lys Arg Thr Ser Asn Arg Ser Asn Ala Ala Arg Arg Val
 1               5                  10                  15

Arg Thr Thr Ala Val Leu Ala Gly Leu Ala Ala Val Ala Ala Leu Ala
                20              25              30

Val Pro Thr Ala Asn Ala Ala Pro Ala Arg Ser Pro Ser Pro Ser Thr
            35              40              45

Gln Pro Trp Glu His Val Asn Ala Ile Gln Glu Ala Arg Arg Leu Leu
        50              55              60

Asn Leu Ser Arg Asp Thr Ala Ala Glu Met Asn Glu Thr Val Glu Val
    65              70              75                          80

Ile Ser Glu Met Phe Asp Leu Gln Glu Pro Thr Cys Leu Gln Thr Arg
                85              90                  95

Leu Glu Leu Tyr Lys Gln Gly Leu Arg Gly Ser Leu Thr Lys Leu Lys
```

|  |  |  |  | 100 |  |  |  | 105 |  |  |  | 110 |  |  |
|---|---|---|---|---|---|---|---|---|---|---|---|---|---|---|
| Gly | Pro | Leu | Thr | Met | Met | Ala | Ser | His | Tyr | Lys | Gln | His | Cys | Pro | Pro |
|  |  | 115 |  |  |  | 120 |  |  |  | 125 |  |  |

Thr Pro Glu Thr Ser Cys Ala Thr Gln Ile Ile Thr Phe Glu Ser Phe
130                 135                 140

Lys Glu Asn Leu Lys Asp Phe Leu Leu Val Ile Pro Phe Asp Cys Trp
145                 150                 155                 160

Glu Pro Val Gln Glu
                165

( 2 ) INFORMATION FOR SEQ ID NO:9:

( i ) SEQUENCE CHARACTERISTICS:
( A ) LENGTH: 909 base pairs
( B ) TYPE: nucleic acid
( C ) STRANDEDNESS: double
( D ) TOPOLOGY: linear ( i i ) MOLECULE TYPE: Other nucleic acid;
( A ) DESCRIPTION: Synthetic DNA oligonucleotide ( i x ) FEATURE:
( A ) NAME/KEY: CDS
( B ) LOCATION: 399..902

( x i ) SEQUENCE DESCRIPTION: SEQ ID NO:9:

```
GATCCGGCCG  TTTCCCGCGC  CGCCCGCGCC  CACGTGGCGC  GGTGGGGGAT  TCCGGCCGAA       60

CGCGCCGACG  CCCATGTGAC  CGCCTGCGTG  CTGCGCGGCG  CCCGCGCCGC  AGGCTCGCCG      120

GGGCGGACCC  GGACCCGGCC  GCCGAGGTCC  TCGCCGCCGA  CCGGGAGGCG  TGCGGCCTCG      180

CCGCGAGACC  GCCGTCCTGC  TGCGGCTCAC  GGAGGCGTAC  CTCTCGCCCT  GCGCGCGGGC      240

CCTCGACCCC  GCCGGGACCT  CCGGCACCGG  GCCCGCGGGC  GACGCCGGGC  GCACCGGGTC      300

CGCCGGCGCC  CCCCACCCC   GCACAAGAAT  GTCCGAAACC  CTACGGGCCC  CGACGAAAGG      360

CGCGGAACGG  CGTCTCCGCC  TCTGCCATGA  TGCCGCCC ATG AGG ATC AAG CGC           413
                                               Met Arg Ile Lys Arg
                                                 1               5
```

```
ACC AGC AAC CGC TCG AAC GCG GCG AGA CGC GTC CGC ACC GCG GCC CTG          461
Thr Ser Asn Arg Ser Asn Ala Ala Arg Arg Val Arg Thr Ala Ala Leu
               10                  15                  20

GCC CTC TCC GCT GCC GCC GCG CTC GTG CTG GGG TCG ACG GCC GCC TCC          509
Ala Leu Ser Ala Ala Ala Ala Leu Val Leu Gly Ser Thr Ala Ala Ser
           25                  30                  35

GGG GCG TCT GCA GCC CCC GCC CGG TCG CCC TCG CCG TCG ACC CAG CCG          557
Gly Ala Ser Ala Ala Pro Ala Arg Ser Pro Ser Pro Ser Thr Gln Pro
       40                  45                  50

TGG GAG CAC GTC AAC GCG ATC CAG GAG GCC CGC CGC CTG CTC AAC CTC          605
Trp Glu His Val Asn Ala Ile Gln Glu Ala Arg Arg Leu Leu Asn Leu
 55                  60                  65

TCG CGG GAC ACG GCC GCC GAG ATG AAC GAG ACC GTG GAG GTG ATC TCG          653
Ser Arg Asp Thr Ala Ala Glu Met Asn Glu Thr Val Glu Val Ile Ser
 70                  75                  80                  85

GAG ATG TTC GAC TTG CAG GAG CCC ACG TGC CTC CAG ACC CGC CTC GAG          701
Glu Met Phe Asp Leu Gln Glu Pro Thr Cys Leu Gln Thr Arg Leu Glu
                 90                  95                 100

CTG TAC AAG CAG GGG CTC CGG GGC AGC CTC ACC AAG CTC AAG GGG CCG          749
Leu Tyr Lys Gln Gly Leu Arg Gly Ser Leu Thr Lys Leu Lys Gly Pro
             105                 110                 115

CTG ACC ATG ATG GCG TCC CAC TAC AAA CAG CAC TGC CCC CCC ACG CCG          797
Leu Thr Met Met Ala Ser His Tyr Lys Gln His Cys Pro Pro Thr Pro
         120                 125                 130
```

```
GAG ACG TCG TGC GCC ACC CAG ATC ATC ACG TTC GAG TCG TTC AAG GAG      845
Glu Thr Ser Cys Ala Thr Gln Ile Ile Thr Phe Glu Ser Phe Lys Glu
    135                 140                 145

AAC CTG AAG GAC TTC CTC CTC GTG ATC CCC TTC GAC TGC TGG GAG CCG      893
Asn Leu Lys Asp Phe Leu Leu Val Ile Pro Phe Asp Cys Trp Glu Pro
150                 155                 160                 165

GTG CAG GAG TGAAGCT                                                  909
Val Gln Glu
```

( 2 ) INFORMATION FOR SEQ ID NO:10:

( i ) SEQUENCE CHARACTERISTICS:
        ( A ) LENGTH: 168 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Met Arg Ile Lys Arg Thr Ser Asn Arg Ser Asn Ala Ala Arg Arg Val
 1               5                  10                  15

Arg Thr Ala Ala Leu Ala Leu Ser Ala Ala Ala Leu Val Leu Gly
                 20                  25                  30

Ser Thr Ala Ala Ser Gly Ala Ser Ala Ala Pro Ala Arg Ser Pro Ser
             35                  40                  45

Pro Ser Thr Gln Pro Trp Glu His Val Asn Ala Ile Gln Glu Ala Arg
     50                  55                  60

Arg Leu Leu Asn Leu Ser Arg Asp Thr Ala Ala Glu Met Asn Glu Thr
 65                  70                  75                  80

Val Glu Val Ile Ser Glu Met Phe Asp Leu Gln Glu Pro Thr Cys Leu
                     85                  90                  95

Gln Thr Arg Leu Glu Leu Tyr Lys Gln Gly Leu Arg Gly Ser Leu Thr
                 100                 105                 110

Lys Leu Lys Gly Pro Leu Thr Met Met Ala Ser His Tyr Lys Gln His
                 115                 120                 125

Cys Pro Pro Thr Pro Glu Thr Ser Cys Ala Thr Gln Ile Ile Thr Phe
     130                 135                 140

Glu Ser Phe Lys Glu Asn Leu Lys Asp Phe Leu Leu Val Ile Pro Phe
145                 150                 155                 160

Asp Cys Trp Glu Pro Val Gln Glu
                 165
```

( 2 ) INFORMATION FOR SEQ ID NO:11:

( i ) SEQUENCE CHARACTERISTICS:
        ( A ) LENGTH: 535 base pairs
        ( B ) TYPE: nucleic acid
        ( C ) STRANDEDNESS: double
        ( D ) TOPOLOGY: linear ( i i ) MOLECULE TYPE: Other nucleic acid;
        ( A ) DESCRIPTION: Synthetic DNA oligonucleotide ( i x ) FEATURE:
        ( A ) NAME/KEY: CDS
        ( B ) LOCATION: 399..533

( x i ) SEQUENCE DESCRIPTION: SEQ ID NO:11:

```
GATCCGGCCG TTTCCCGCGC CGCCCGCGCC CACGTGGCGC GGTGGGGGAT TCCGGCCGAA      60

CGCGCCGACG CCCATGTGAC CGCCTGCGTG CTGCGCGGCG CCCGCGCCGC AGGCTCGCCG     120

GGGCGGACCC GGACCCGGCC GCCGAGGTCC TCGCCGCCGA CCGGGAGGCG TGCGGCCTCG     180
```

```
CCGCGAGACC  GCCGTCCTGC  TGCGGCTCAC  GGAGGCGTAC  CTCTCGCCCT  GCGCGCGGGC      240

CCTCGACCCC  GCCGGGACCT  CCGGCACCGG  GCCCGCGGGC  GACGCCGGGC  GCACCGGGTC      300

CGCCGGCGCC  CCCCCACCCC  GCACAAGAAT  GTCCGAAACC  CTACGGGCCC  CGACGAAAGG      360

CGCGGAACGG  CGTCTCCGCC  TCTGCCATGA  TGCCGCCC  ATG AGG ATC AAG CGC           413
                                              Met Arg Ile Lys Arg
                                               1               5

ACC AGC AAC CGC TCG AAC GCG GCG AGA CGC GTC CGC ACC ACC GCC GTA             461
Thr Ser Asn Arg Ser Asn Ala Ala Arg Arg Val Arg Thr Thr Ala Val
             10                  15                  20

CTC GCG GGG CTC GCC GCC GTC GCG GCG CTG GCC GTT CCC ACC GCC AAT             509
Leu Ala Gly Leu Ala Ala Val Ala Ala Leu Ala Val Pro Thr Ala Asn
             25                  30                  35

GCA TTC CCG ACC ATC CCG CTG TCT AG                                          535
Ala Phe Pro Thr Ile Pro Leu Ser
             40              45
```

( 2 ) INFORMATION FOR SEQ ID NO:12:

( i ) SEQUENCE CHARACTERISTICS:
       ( A ) LENGTH: 45 amino acids
       ( B ) TYPE: amino acid
       ( D ) TOPOLOGY: linear ( i i ) MOLECULE TYPE: protein ( x i ) SEQUENCE DESCRIPTION: SEQ ID NO:12:

```
Met Arg Ile Lys Arg Thr Ser Asn Arg Ser Asn Ala Ala Arg Arg Val
 1               5                  10                  15

Arg Thr Thr Ala Val Leu Ala Gly Leu Ala Ala Val Ala Ala Leu Ala
                 20                  25                  30

Val Pro Thr Ala Asn Ala Phe Pro Thr Ile Pro Leu Ser
                 35                  40              45
```

( 2 ) INFORMATION FOR SEQ ID NO:13:

( i ) SEQUENCE CHARACTERISTICS:
       ( A ) LENGTH: 838 base pairs
       ( B ) TYPE: nucleic acid
       ( C ) STRANDEDNESS: double
       ( D ) TOPOLOGY: linear ( i i ) MOLECULE TYPE: Other nucleic acid;
       ( A ) DESCRIPTION: Synthetic DNA oligonucleotide ( i x ) FEATURE:
       ( A ) NAME/KEY: CDS
       ( B ) LOCATION: 399..836

( x i ) SEQUENCE DESCRIPTION: SEQ ID NO:13:

```
GATCCGGCCG  TTTCCCGCGC  CGCCCGCGCC  CACGTGGCGC  GGTGGGGGAT  TCCGGCCGAA       60

CGCGCCGACG  CCCATGTGAC  CGCCTGCGTG  CTGCGCGGCG  CCCGCGCCGC  AGGCTCGCCG      120

GGGCGGACCC  GGACCCGGCC  GCCGAGGTCC  TCGCCGCCGA  CCGGGAGGCG  TGCGGCCTCG      180

CCGCGAGACC  GCCGTCCTGC  TGCGGCTCAC  GGAGGCGTAC  CTCTCGCCCT  GCGCGCGGGC      240

CCTCGACCCC  GCCGGGACCT  CCGGCACCGG  GCCCGCGGGC  GACGCCGGGC  GCACCGGGTC      300

CGCCGGCGCC  CCCCCACCCC  GCACAAGAAT  GTCCGAAACC  CTACGGGCCC  CGACGAAAGG      360

CGCGGAACGG  CGTCTCCGCC  TCTGCCATGA  TGCCGCCC  ATG AGG ATC AAG CGC           413
                                            Met Arg Ile Lys Arg
                                             1               5
```

```
ACC AGC AAC CGC TCG AAC GCG GCG AGA CGC GTC CGC ACC GCG GCC CTG    461
Thr Ser Asn Arg Ser Asn Ala Ala Arg Arg Val Arg Thr Ala Ala Leu
            10                  15                  20

GCC CTC TCC GCT GCC GCC GCG CTC GTG CTG GGG TCG ACG GCC GCC TCC    509
Ala Leu Ser Ala Ala Ala Ala Leu Val Leu Gly Ser Thr Ala Ala Ser
                25                  30                  35

GGG GCG TCT GCA GAG ATC ACT AGA ATC CCA TTG TAC AAG GGT AAG TCT    557
Gly Ala Ser Ala Glu Ile Thr Arg Ile Pro Leu Tyr Lys Gly Lys Ser
            40                  45                  50

TTG AGA AAG GCC TTG AAG GAA CAC GGT TTG TTG GAA GAC TTC TTG CAA    605
Leu Arg Lys Ala Leu Lys Glu His Gly Leu Leu Glu Asp Phe Leu Gln
        55                  60                  65

AAG CAA CAA TAC GGT ATC TCC TCC AAG TAC TCT GGT TTC GGT GAA GTC    653
Lys Gln Gln Tyr Gly Ile Ser Ser Lys Tyr Ser Gly Phe Gly Glu Val
70                  75                  80                  85

GCT TCC GTT CCA TTG ACC AAC TAC TTG GAC TCC CAA TAC TTC GGT AAG    701
Ala Ser Val Pro Leu Thr Asn Tyr Leu Asp Ser Gln Tyr Phe Gly Lys
                90                  95                  100

ATC TAC TTA GGT ACC CCA CCA CAA GAA TTC ACT GTC TTG TTC GAC ACC    749
Ile Tyr Leu Gly Thr Pro Pro Gln Glu Phe Thr Val Leu Phe Asp Thr
            105                 110                 115

GGT TCT TCT GAC TTC TGG GTC CCA TCG ATT TAC TGT AAG TCC AAC GCT    797
Gly Ser Ser Asp Phe Trp Val Pro Ser Ile Tyr Cys Lys Ser Asn Ala
        120                 125                 130

TGT AAG AAC CAC CAA AGA TTC GAC CCA AGA AAG AGC TCT AG             838
Cys Lys Asn His Gln Arg Phe Asp Pro Arg Lys Ser Ser
135                 140                 145
```

( 2 ) INFORMATION FOR SEQ ID NO:14:

( i ) SEQUENCE CHARACTERISTICS:
( A ) LENGTH: 146 amino acids
( B ) TYPE: amino acid
( D ) TOPOLOGY: linear ( i i ) MOLECULE TYPE: protein ( x i ) SEQUENCE DESCRIPTION: SEQ ID NO:14:

```
Met Arg Ile Lys Arg Thr Ser Asn Arg Ser Asn Ala Ala Arg Arg Val
1               5                   10                  15

Arg Thr Ala Ala Leu Ala Leu Ser Ala Ala Ala Leu Val Leu Gly
            20                  25                  30

Ser Thr Ala Ala Ser Gly Ala Ser Ala Glu Ile Thr Arg Ile Pro Leu
            35                  40                  45

Tyr Lys Gly Lys Ser Leu Arg Lys Ala Leu Lys Glu His Gly Leu Leu
        50                  55                  60

Glu Asp Phe Leu Gln Lys Gln Gln Tyr Gly Ile Ser Ser Lys Tyr Ser
65                  70                  75                  80

Gly Phe Gly Glu Val Ala Ser Val Pro Leu Thr Asn Tyr Leu Asp Ser
                85                  90                  95

Gln Tyr Phe Gly Lys Ile Tyr Leu Gly Thr Pro Pro Gln Glu Phe Thr
            100                 105                 110

Val Leu Phe Asp Thr Gly Ser Ser Asp Phe Trp Val Pro Ser Ile Tyr
        115                 120                 125

Cys Lys Ser Asn Ala Cys Lys Asn His Gln Arg Phe Asp Pro Arg Lys
        130                 135                 140

Ser Ser
145
```

( 2 ) INFORMATION FOR SEQ ID NO:15:

( i ) SEQUENCE CHARACTERISTICS:
  ( A ) LENGTH: 832 base pairs
  ( B ) TYPE: nucleic acid
  ( C ) STRANDEDNESS: double
  ( D ) TOPOLOGY: linear ( i i ) MOLECULE TYPE: Other nucleic acid;
  ( A ) DESCRIPTION: Synthetic DNA oligonucleotide ( i x ) FEATURE:
  ( A ) NAME/KEY: CDS
  ( B ) LOCATION: 399..830

( x i ) SEQUENCE DESCRIPTION: SEQ ID NO:15:

| | | | | | |
|---|---|---|---|---|---|
| GATCCGGCCG | TTTCCCGCGC | CGCCCGCGCC | CACGTGGCGC | GGTGGGGGAT | TCCGGCCGAA | 60 |
| CGCGCCGACG | CCCATGTGAC | CGCCTGCGTG | CTGCGCGGCG | CCCGCGCCGC | AGGCTCGCCG | 120 |
| GGGCGGACCC | GGACCCGGCC | GCCGAGGTCC | TCGCCGCCGA | CCGGGAGGCG | TGCGGCCTCG | 180 |
| CCGCGAGACC | GCCGTCCTGC | TGCGGCTCAC | GGAGGCGTAC | CTCTCGCCCT | GCGCGCGGGC | 240 |
| CCTCGACCCC | GCCGGGACCT | CCGGCACCGG | GCCCGCGGGC | GACGCCGGGC | GCACCGGGTC | 300 |
| CGCCGGCGCC | CCCCCACCCC | GCACAAGAAT | GTCCGAAACC | CTACGGGCCC | CGACGAAAGG | 360 |
| CGCGGAACGG | CGTCTCCGCC | TCTGCCATGA | TGCCGCCC | ATG AGG ATC AAG CGC | | 413 |

```
                                                                Met Arg Ile Lys Arg
                                                                 1               5

ACC AGC AAC CGC TCG AAC GCG GCG AGA CGC GTC CGC ACC ACC GCC GTA      461
Thr Ser Asn Arg Ser Asn Ala Ala Arg Arg Val Arg Thr Thr Ala Val
            10                  15                  20

CTC GCG GGG CTC GCC GCC GTC GCG GCG CTG GCC GTT CCC ACC GCG AAC      509
Leu Ala Gly Leu Ala Ala Val Ala Ala Leu Ala Val Pro Thr Ala Asn
        25                  30                  35

GCT GCA GAG ATC ACT AGA ATC CCA TTG TAC AAG GGT AAG TCT TTG AGA      557
Ala Ala Glu Ile Thr Arg Ile Pro Leu Tyr Lys Gly Lys Ser Leu Arg
    40                  45                  50

AAG GCC TTG AAG GAA CAC GGT TTG TTG GAA GAC TTC TTG CAA AAG CAA      605
Lys Ala Leu Lys Glu His Gly Leu Leu Glu Asp Phe Leu Gln Lys Gln
55                  60                  65

CAA TAC GGT ATC TCC TCC AAG TAC TCT GGT TTC GGT GAA GTC GCT TCC      653
Gln Tyr Gly Ile Ser Ser Lys Tyr Ser Gly Phe Gly Glu Val Ala Ser
70                  75                  80                  85

GTT CCA TTG ACC AAC TAC TTG GAC TCC CAA TAC TTC GGT AAG ATC TAC      701
Val Pro Leu Thr Asn Tyr Leu Asp Ser Gln Tyr Phe Gly Lys Ile Tyr
        90                  95                  100

TTA GGT ACC CCA CCA CAA GAA TTC ACT GTC TTG TTC GAC ACC GGT TCT      749
Leu Gly Thr Pro Pro Gln Glu Phe Thr Val Leu Phe Asp Thr Gly Ser
    105                 110                 115

TCT GAC TTC TGG GTC CCA TCG ATT TAC TGT AAG TCC AAC GCT TGT AAG      797
Ser Asp Phe Trp Val Pro Ser Ile Tyr Cys Lys Ser Asn Ala Cys Lys
        120                 125                 130

AAC CAC CAA AGA TTC GAC CCA AGA AAG AGC TCT AG                       832
Asn His Gln Arg Phe Asp Pro Arg Lys Ser Ser
        135                 140
```

( 2 ) INFORMATION FOR SEQ ID NO:16:

( i ) SEQUENCE CHARACTERISTICS:
    ( A ) LENGTH: 144 amino acids
    ( B ) TYPE: amino acid
    ( D ) TOPOLOGY: linear ( i i ) MOLECULE TYPE: protein ( x i ) SEQUENCE DESCRIPTION: SEQ ID NO:16:

| Met | Arg | Ile | Lys | Arg | Thr | Ser | Asn | Arg | Ser | Asn | Ala | Ala | Arg | Arg | Val |
|-----|-----|-----|-----|-----|-----|-----|-----|-----|-----|-----|-----|-----|-----|-----|-----|
| 1 |     |     |     | 5 |     |     |     |     | 10 |     |     |     |     | 15 |     |

| Arg | Thr | Thr | Ala | Val | Leu | Ala | Gly | Leu | Ala | Ala | Val | Ala | Ala | Leu | Ala |
|-----|-----|-----|-----|-----|-----|-----|-----|-----|-----|-----|-----|-----|-----|-----|-----|
|     |     |     | 20 |     |     |     |     | 25 |     |     |     |     | 30 |     |     |

| Val | Pro | Thr | Ala | Asn | Ala | Ala | Glu | Ile | Thr | Arg | Ile | Pro | Leu | Tyr | Lys |
|-----|-----|-----|-----|-----|-----|-----|-----|-----|-----|-----|-----|-----|-----|-----|-----|
|     |     | 35 |     |     |     |     | 40 |     |     |     |     | 45 |     |     |     |

| Gly | Lys | Ser | Leu | Arg | Lys | Ala | Leu | Lys | Glu | His | Gly | Leu | Leu | Glu | Asp |
|-----|-----|-----|-----|-----|-----|-----|-----|-----|-----|-----|-----|-----|-----|-----|-----|
|     | 50 |     |     |     |     | 55 |     |     |     |     | 60 |     |     |     |     |

| Phe | Leu | Gln | Lys | Gln | Gln | Tyr | Gly | Ile | Ser | Ser | Lys | Tyr | Ser | Gly | Phe |
|-----|-----|-----|-----|-----|-----|-----|-----|-----|-----|-----|-----|-----|-----|-----|-----|
| 65 |     |     |     |     | 70 |     |     |     |     | 75 |     |     |     |     | 80 |

| Gly | Glu | Val | Ala | Ser | Val | Pro | Leu | Thr | Asn | Tyr | Leu | Asp | Ser | Gln | Tyr |
|-----|-----|-----|-----|-----|-----|-----|-----|-----|-----|-----|-----|-----|-----|-----|-----|
|     |     |     |     | 85 |     |     |     |     | 90 |     |     |     |     | 95 |     |

| Phe | Gly | Lys | Ile | Tyr | Leu | Gly | Thr | Pro | Pro | Gln | Glu | Phe | Thr | Val | Leu |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Phe | Asp | Thr | Gly | Ser | Ser | Asp | Phe | Trp | Val | Pro | Ser | Ile | Tyr | Cys | Lys |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Ser | Asn | Ala | Cys | Lys | Asn | His | Gln | Arg | Phe | Asp | Pro | Arg | Lys | Ser | Ser |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

( 2 ) INFORMATION FOR SEQ ID NO:17:

( i ) SEQUENCE CHARACTERISTICS:
        ( A ) LENGTH: 401 base pairs
        ( B ) TYPE: nucleic acid
        ( C ) STRANDEDNESS: double
        ( D ) TOPOLOGY: linear ( i i ) MOLECULE TYPE: Other nucleic acid;
        ( A ) DESCRIPTION: Synthetic DNA oligonucleotide ( x i ) SEQUENCE DESCRIPTION: SEQ ID NO:17:

| GATCCGGCCG | TTTCCCGCGC | CGCCCGCGCC | CACGTGGCGC | GGTGGGGGAT | TCCGGCCGAA | 60 |
|---|---|---|---|---|---|---|
| CGCGCCGACG | CCCATGTGAC | CGCCTGCGTG | CTGCGCGGCG | CCCGCGCCGC | AGGCTCGCCG | 120 |
| GGGCGGACCC | GGACCCGGCC | GCCGAGGTCC | TCGCCGCCGA | CCGGGAGGCG | TGCGGCCTCG | 180 |
| CCGCGAGACC | GCCGTCCTGC | TGCGGCTCAC | GGAGGCGTAC | CTCTCGCCCT | GCGCGCGGGC | 240 |
| CCTCGACCCC | GCCGGGACCT | CCGGCACCGG | GCCCGCGGGC | GACGCCGGGC | GCACCGGGTC | 300 |
| CGCCGGCGCC | CCCCCACCCC | GCACAAGAAT | GTCCGAAACC | CTACGGGCCC | CGACGAAAGG | 360 |
| CGCGGAACGG | CGTCTCCGCC | TCTGCCATGA | TGCCGCCCAT | G | | 401 |

( 2 ) INFORMATION FOR SEQ ID NO:18:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( x i ) SEQUENCE DESCRIPTION: SEQ ID NO:18:

| GGCCTCGTCT | AGA | 13 |
|---|---|---|

( 2 ) INFORMATION FOR SEQ ID NO:19:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Other nucleic acid;
    ( A ) DESCRIPTION: Synthetic DNA oligonucleotide ( i v ) ANTI-SENSE: YES ( x i ) SEQUENCE DESCRIPTION: SEQ ID NO:19:

AGCTTCTAGA CGAGGCCTGC A    21

( 2 ) INFORMATION FOR SEQ ID NO:20:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( x i ) SEQUENCE DESCRIPTION: SEQ ID NO:20:

TGGCCGTTCC CACCGCCAAT GCATTCCCGA CCATCCCGCT GT    42

( 2 ) INFORMATION FOR SEQ ID NO:21:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( i v ) ANTI-SENSE: YES ( x i ) SEQUENCE DESCRIPTION: SEQ ID NO:21:

CTAGACAGCG GGATGGTCGG GAATGCATTG GCGGTGGGAA CGGCCAGCGC    50

( 2 ) INFORMATION FOR SEQ ID NO:22:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:22:

Ala Val Pro Thr Ala Asn Ala Phe Pro Thr Ile Pro Leu
    1               5               10

( 2 ) INFORMATION FOR SEQ ID NO:23:

( i ) SEQUENCE CHARACTERISTICS:
        ( A ) LENGTH: 501 base pairs
        ( B ) TYPE: nucleic acid
        ( C ) STRANDEDNESS: double
        ( D ) TOPOLOGY: linear ( i i ) MOLECULE TYPE: Other nucleic acid;
        ( A ) DESCRIPTION: Synthetic DNA oligonucleotide ( i x ) FEATURE:
        ( A ) NAME/KEY: CDS
        ( B ) LOCATION: 352..501

( x i ) SEQUENCE DESCRIPTION: SEQ ID NO:23:

GATCCACGCG CTGTGCCCGC CGTGCGCCTT CGCCGATCAC TTCATCTGCC CGTTCCCGCC    60

CCCGGGCAAC ACGCTCGCCG CGGCGGTTTT GGCGGGGGAG CGGAACCGGA TCGACGCCTG    120

```
ACCCGCGCGA GGCCCCACCG GCCCCGGCAG CCGCACGGCT CCCGGGGCCG GTGACGGATG      180

TGACCCGCGT GGCCGAAAGG CATTCTTGCG TCCCCCGTCC GGCCCCCTCG ATACTCCGGT      240

CAGCGATTGT CAGGGGCACG GCGAATTCGA AATCCGGACA GGCCCCCGAC TGCGCCTCAC      300

GGGCCCGCCA CCCCACAGGA GGGCCCCCGA TTCCCCTCGG AGGAACCCGA A GTG AGG       357
                                                          Val Arg
                                                            1

ATC AAG CGC ACC AGC AAC CGC TCG AAC GCG GCG AGA CGC GTC CGC ACC        405
Ile Lys Arg Thr Ser Asn Arg Ser Asn Ala Ala Arg Arg Val Arg Thr
        5               10                  15

ACC GCC GTA CTC GCG GGG CTC GCC GCC GTC GCG GCG CTG GCC GTT CCC        453
Thr Ala Val Leu Ala Gly Leu Ala Ala Val Ala Ala Leu Ala Val Pro
 20               25                  30

ACC GCG AAC GCC GAA ACC CCC CGG ACG TTC AGT GCC AAC CAG GCT GCA        501
Thr Ala Asn Ala Glu Thr Pro Arg Thr Phe Ser Ala Asn Gln Ala Ala
 35              40              45                      50
```

( 2 ) INFORMATION FOR SEQ ID NO:24:

( i ) SEQUENCE CHARACTERISTICS:
        ( A ) LENGTH: 50 amino acids
        ( B ) TYPE: amino acid
        ( D ) TOPOLOGY: linear ( i i ) MOLECULE TYPE: protein ( x i ) SEQUENCE DESCRIPTION: SEQ ID NO:24:

```
Val Arg Ile Lys Arg Thr Ser Asn Arg Ser Asn Ala Ala Arg Arg Val
 1               5                  10                  15

Arg Thr Thr Ala Val Leu Ala Gly Leu Ala Ala Val Ala Ala Leu Ala
          20              25                  30

Val Pro Thr Ala Asn Ala Glu Thr Pro Arg Thr Phe Ser Ala Asn Gln
          35              40                  45

Ala Ala
 50
```

( 2 ) INFORMATION FOR SEQ ID NO:25:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( x i ) SEQUENCE DESCRIPTION: SEQ ID NO:25:

```
CATGAGGATC AAGCGCACCA GCAACCGCTC GAACGCGGCG AGA                        43
```

( 2 ) INFORMATION FOR SEQ ID NO:26:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( i v ) ANTI-SENSE: YES ( x i ) SEQUENCE DESCRIPTION: SEQ ID NO:26:

```
CGCGTCTCGC CGCGTTCGAG CGGTTGCTGG TGCGCTTGAT CCT                              43
```

(2) INFORMATION FOR SEQ ID NO:27:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:27:

```
Met Arg Ile Lys Arg Thr Ser Asn Arg Ser Asn Ala Ala Arg
 1               5                   10
```

(2) INFORMATION FOR SEQ ID NO:28:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Synthetic DNA oligonucleotide (xi) SEQUENCE DESCRIPTION: SEQ ID NO:28:

```
TGGCCGTTCC CACCGCGAAC GCTGCA                                                26
```

(2) INFORMATION FOR SEQ ID NO:29:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Synthetic DNA oligonucleotide (iv) ANTI-SENSE: YES (xi) SEQUENCE DESCRIPTION: SEQ ID NO:29:

```
GCGTTCGCGG TGGGAACGGC CAGCGC                                                26
```

(2) INFORMATION FOR SEQ ID NO:30:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:30:

```
Ala Val Pro Thr Ala Asn Ala Ala
 1               5
```

(2) INFORMATION FOR SEQ ID NO:31:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Synthetic DNA oligonucleotide (xi) SEQUENCE DESCRIPTION: SEQ ID NO:31:

```
CGCGTCCGCA  CCGCGGCCCT  GGCCCTCTCC  GCTGCCGCCG  CGCTCGTGCT  GGGGTCGACG    60

GCCGCCTCCG  GGGCGTCTGC  A                                                 81
```

(2) INFORMATION FOR SEQ ID NO:32:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Synthetic DNA oligonucleotide (iv) ANTI-SENSE: YES (xi) SEQUENCE DESCRIPTION: SEQ ID NO:32:

```
GACGCCCCGG  AGGCGGCCGT  CGACCCCAGC  ACGAGCGCGG  CGGCAGCGGA  GAGGGCCAGG    60

GCCGCGGTGC  GGA                                                           73
```

(2) INFORMATION FOR SEQ ID NO:33:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (xi) SEQUENCE DESCRIPTION: SEQ ID NO:33:

```
Arg  Val  Arg  Thr  Ala  Ala  Leu  Ala  Leu  Ser  Ala  Ala  Ala  Ala  Leu  Val
1                   5                        10                         15

Leu  Gly  Ser  Thr  Ala  Ala  Ser  Gly  Ala  Ser  Ala
               20                  25
```

(2) INFORMATION FOR SEQ ID NO:34:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Synthetic DNA oligonucleotide (xi) SEQUENCE DESCRIPTION: SEQ ID NO:34:

```
CATGTTCACT  CCCGTTCGGA  GA                                                22
```

(2) INFORMATION FOR SEQ ID NO:35:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Synthetic DNA oligonucleotide (iv) ANTI-SENSE: YES (xi) SEQUENCE DESCRIPTION: SEQ ID NO:35:

```
CGCGTCTCCG  AACCGGAGTG  AA                                                22
```

(2) INFORMATION FOR SEQ ID NO:36:

(i) SEQUENCE CHARACTERISTICS:

(A) LENGTH: 7 amino acids
(B) TYPE: amino acid
(D) TOPOLOGY: linear (i i) MOLECULE TYPE: peptide (x i) SEQUENCE DESCRIPTION: SEQ ID NO:36:

Met Phe Thr Pro Val Arg Arg
1               5

(2) INFORMATION FOR SEQ ID NO:37:

(i) SEQUENCE CHARACTERISTICS:
(A) LENGTH: 81 base pairs
(B) TYPE: nucleic acid
(C) STRANDEDNESS: single
(D) TOPOLOGY: linear (i i) MOLECULE TYPE: Other nucleic acid;
(A) DESCRIPTION: Synthetic DNA oligonucleotide (x i) SEQUENCE DESCRIPTION: SEQ ID NO:37:

CGCGTGTGGA TCTCCCTCCT GTTCGCGCTC GCCCTGATCT TCACCATGGC CTTCGGGTCG    60

ACGTCCTCCG CCCAGGCTGC A                                              81

(2) INFORMATION FOR SEQ ID NO:38:

(i) SEQUENCE CHARACTERISTICS:
(A) LENGTH: 73 base pairs
(B) TYPE: nucleic acid
(C) STRANDEDNESS: single
(D) TOPOLOGY: linear (i i) MOLECULE TYPE: Other nucleic acid;
(A) DESCRIPTION: Synthetic DNA oligonucleotide (i v) ANTI-SENSE: YES (x i) SEQUENCE DESCRIPTION: SEQ ID NO:38:

GCCTGGGCGG AGGACGTCGA CCCGAAGGCC ATGGTGAAGA TCAGGGCGAG CGCGAACAGG    60

AGGGAGATCC ACA                                                       73

(2) INFORMATION FOR SEQ ID NO:39:

(i) SEQUENCE CHARACTERISTICS:
(A) LENGTH: 27 amino acids
(B) TYPE: amino acid
(D) TOPOLOGY: linear (i i) MOLECULE TYPE: peptide (x i) SEQUENCE DESCRIPTION: SEQ ID NO:39:

Arg Val Trp Ile Ser Leu Leu Phe Ala Leu Ala Leu Ile Phe Thr Met
1               5                   10                  15

Ala Phe Gly Ser Thr Ser Ser Ala Gln Ala Ala
            20                  25

(2) INFORMATION FOR SEQ ID NO:40:

(i) SEQUENCE CHARACTERISTICS:
(A) LENGTH: 21 base pairs
(B) TYPE: nucleic acid
(C) STRANDEDNESS: single
(D) TOPOLOGY: linear (i i) MOLECULE TYPE: Other nucleic acid;
(A) DESCRIPTION: Synthetic DNA oligonucleotide (x i) SEQUENCE DESCRIPTION: SEQ ID NO:40:

CCCGCCCGGT CGCCCTCGCC G                                                                                           21

( 2 ) INFORMATION FOR SEQ ID NO:41:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( i v ) ANTI-SENSE: YES ( x i ) SEQUENCE DESCRIPTION: SEQ ID NO:41:

TCGACGGCGA GGGCGACCGG GCGGGTGCA                                                                                   29

( 2 ) INFORMATION FOR SEQ ID NO:42:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:42:

Pro Ala Arg Ser Pro Ser Pro
1               5

( 2 ) INFORMATION FOR SEQ ID NO:43:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:43:

Ala Pro Ala Arg Ser Pro Ser Pro Ser
1               5

( 2 ) INFORMATION FOR SEQ ID NO:44:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( x i ) SEQUENCE DESCRIPTION: SEQ ID NO:44:

CGCGTGCGGA CGGCCATCGC CATCGCGGTC GCCCTGGCCG GCTTCGCCAC CGTCGCGCAG                                                  60

GCTGCA                                                                                                            66

( 2 ) INFORMATION FOR SEQ ID NO:45:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( i v ) ANTI-SENSE: YES ( x i ) SEQUENCE DESCRIPTION: SEQ ID NO:45:

GCCTGCGCGA CGGTGGCGAA GCCGGCCAGG GCGACCGCGA TGGCGATGGC CGTCCGCA    58

( 2 ) INFORMATION FOR SEQ ID NO:46:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:46:

```
Arg Val Arg Thr Ala Ile Ala Ile Ala Val Ala Leu Ala Gly Phe Ala
1               5                   10                  15
Thr Val Ala Gln Ala Ala
            20
```

( 2 ) INFORMATION FOR SEQ ID NO:47:

( i ) SEQUENCE CHARACTERISTICS:
        ( A ) LENGTH: 35 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:47:

```
Met Arg Ile Lys Arg Thr Ser Asn Arg Ser Asn Ala Ala Arg Arg Val
1               5                   10                  15
Arg Thr Ala Ile Ala Ile Ala Val Ala Leu Ala Gly Phe Ala Thr Val
            20                  25                  30
Ala Gln Ala
        35
```

( 2 ) INFORMATION FOR SEQ ID NO:48:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( x i ) SEQUENCE DESCRIPTION: SEQ ID NO:48:

CCCGCGCGCT CCCCCAGCCC G    21

( 2 ) INFORMATION FOR SEQ ID NO:49:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( i v ) ANTI-SENSE: YES ( x i ) SEQUENCE DESCRIPTION: SEQ ID NO:49:

TCGACGGGCT GGGGGAGCGC GCGGGTGCA    29

( 2 ) INFORMATION FOR SEQ ID NO:50:

( i ) SEQUENCE CHARACTERISTICS:
        ( A ) LENGTH: 137 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( x i ) SEQUENCE DESCRIPTION: SEQ ID NO:50:

```
AGCTCTCGAA TTTTGGCGCC CAGGGTCTGC GGAAGTCATT GCCAAATATA AGATTCTTCA      60

GCCAGGCGGG AATCGAAGAA GGAGAACGAT CATGAGGATC AAGCGCACCA GCAACCGCTC     120

GAACGCGGCG AGAGCGC                                                    137
```

( 2 ) INFORMATION FOR SEQ ID NO:51:

( i ) SEQUENCE CHARACTERISTICS:
        ( A ) LENGTH: 194 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( x i ) SEQUENCE DESCRIPTION: SEQ ID NO:51:

```
GATCCGTCGA CCTGCAGCCG TACCGATTGT CACCCTGCGA CACTCCGCTG TAGCATTCGG      60

GAAACCGGTT CACCTCATTG AATGATCAGG CGAGCGAAAG CCCAGAAACT TACCTCCTGG     120

AGCCTAGCTC CTCCTGCGCC GTGGAATGAT CGTGCCACGT GGGCGTTCCG GAACTTTTTG     180

CACGCACGCG AGCT                                                       194
```

( 2 ) INFORMATION FOR SEQ ID NO:52:

( i ) SEQUENCE CHARACTERISTICS:
        ( A ) LENGTH: 406 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( i x ) FEATURE:
        ( A ) NAME/KEY: CDS
        ( B ) LOCATION: 5..403

( x i ) SEQUENCE DESCRIPTION: SEQ ID NO:52:

```
TGCA GCG CCG ATG ACG CAG ACC ACG TCG CTG AAG ACG TCG TGG GTG AAC       49
     Ala Pro Met Thr Gln Thr Thr Ser Leu Lys Thr Ser Trp Val Asn
      1               5                  10                  15

TGC TCC AAC ATG ATC GAC GAG ATC ATC ACG CAC CTG AAG CAG CCC CCG        97
Cys Ser Asn Met Ile Asp Glu Ile Ile Thr His Leu Lys Gln Pro Pro
             20                  25                  30

CTC CCC CTG CTC GAC TTC AAC AAC CTG AAC GGC GAG GAC CAG GAC ATC       145
Leu Pro Leu Leu Asp Phe Asn Asn Leu Asn Gly Glu Asp Gln Asp Ile
         35                  40                  45

CTC ATG GAG AAC AAC CTC CGC CGC CCG AAC CTC GAG GCC TTC AAC CGG       193
Leu Met Glu Asn Asn Leu Arg Arg Pro Asn Leu Glu Ala Phe Asn Arg
     50                  55                  60

GCC GTC AAG TCC CTC CAG AAC GCC TCG GCC ATC GAG AGC ATC CTG AAG       241
Ala Val Lys Ser Leu Gln Asn Ala Ser Ala Ile Glu Ser Ile Leu Lys
 65                  70                  75
```

```
AAC  CTG  CTG  CCC  TGC  CTG  CCG  CTC  GCC  ACG  GCG  GCC  CCC  ACC  CGG  CAC            289
Asn  Leu  Leu  Pro  Cys  Leu  Pro  Leu  Ala  Thr  Ala  Ala  Pro  Thr  Arg  His
 80                  85                       90                       95

CCC  ATC  CAC  ATC  AAG  GAC  GGG  GAC  TGG  AAC  GAG  TTC  CGG  CGC  AAG  CTC            337
Pro  Ile  His  Ile  Lys  Asp  Gly  Asp  Trp  Asn  Glu  Phe  Arg  Arg  Lys  Leu
                    100                      105                      110

ACG  TTC  TAC  CTC  AAG  ACG  CTG  GAG  AAC  GCG  CAG  GCC  CAG  CAG  ACG  ACC            385
Thr  Phe  Tyr  Leu  Lys  Thr  Leu  Glu  Asn  Ala  Gln  Ala  Gln  Gln  Thr  Thr
               115                      120                      125

CTC  TCC  CTC  GCG  ATC  TTC  TAG                                                         406
Leu  Ser  Leu  Ala  Ile  Phe
          130
```

( 2 ) INFORMATION FOR SEQ ID NO:53:

( i ) SEQUENCE CHARACTERISTICS:
        ( A ) LENGTH: 133 amino acids
        ( B ) TYPE: amino acid
        ( D ) TOPOLOGY: linear ( i i ) MOLECULE TYPE: protein ( x i ) SEQUENCE DESCRIPTION: SEQ ID NO:53:

```
Ala  Pro  Met  Thr  Gln  Thr  Thr  Ser  Leu  Lys  Thr  Ser  Trp  Val  Asn  Cys
 1                    5                      10                      15

Ser  Asn  Met  Ile  Asp  Glu  Ile  Ile  Thr  His  Leu  Lys  Gln  Pro  Pro  Leu
               20                       25                      30

Pro  Leu  Leu  Asp  Phe  Asn  Asn  Leu  Asn  Gly  Glu  Asp  Gln  Asp  Ile  Leu
          35                       40                      45

Met  Glu  Asn  Asn  Leu  Arg  Arg  Pro  Asn  Leu  Glu  Ala  Phe  Asn  Arg  Ala
     50                       55                      60

Val  Lys  Ser  Leu  Gln  Asn  Ala  Ser  Ala  Ile  Glu  Ser  Ile  Leu  Lys  Asn
 65                      70                      75                      80

Leu  Leu  Pro  Cys  Leu  Pro  Leu  Ala  Thr  Ala  Ala  Pro  Thr  Arg  His  Pro
                85                       90                      95

Ile  His  Ile  Lys  Asp  Gly  Asp  Trp  Asn  Glu  Phe  Arg  Arg  Lys  Leu  Thr
               100                      105                     110

Phe  Tyr  Leu  Lys  Thr  Leu  Glu  Asn  Ala  Gln  Ala  Gln  Gln  Thr  Thr  Leu
          115                      120                     125

Ser  Leu  Ala  Ile  Phe
          130
```

( 2 ) INFORMATION FOR SEQ ID NO:54:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( x i ) SEQUENCE DESCRIPTION: SEQ ID NO:54:

```
GCGCCGATGA CGCAGACCAC GCCGCTGAAG ACGT                                                      34
```

( 2 ) INFORMATION FOR SEQ ID NO:55:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear 5,641,663

77

78

-continued ( i i ) MOLECULE TYPE: Other nucleic acid;
   ( A ) DESCRIPTION: Synthetic DNA oligonucleotide ( i v ) ANTI-SENSE: YES ( x i ) SEQUENCE DESCRIPTION: SEQ ID NO:55:

CTTCAGCGGC GTGGTCTGCG TCATCGGCGC TGCA                                    34

( 2 ) INFORMATION FOR SEQ ID NO:56:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:56:

Ala Pro Met Thr Gln Thr Thr Pro Leu Lys Thr
1               5                   10

( 2 ) INFORMATION FOR SEQ ID NO:57:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:57:

Xaa Pro Met Thr Gln Thr Thr Ser Xaa Lys
1               5                   10

( 2 ) INFORMATION FOR SEQ ID NO:58:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:58:

Xaa Pro Met Thr Gln Thr Thr Pro Xaa Xaa
1               5                   10

( 2 ) INFORMATION FOR SEQ ID NO:59:

( i ) SEQUENCE CHARACTERISTICS:
        ( A ) LENGTH: 498 base pairs
        ( B ) TYPE: nucleic acid
        ( C ) STRANDEDNESS: double
        ( D ) TOPOLOGY: linear ( i i ) MOLECULE TYPE: Other nucleic acid;
        ( A ) DESCRIPTION: Synthetic DNA oligonucleotide ( i x ) FEATURE:
        ( A ) NAME/KEY: CDS
        ( B ) LOCATION: 1..492

( x i ) SEQUENCE DESCRIPTION: SEQ ID NO:59:

AGC TCC GAG CGC ATC GAC AAG CAG ATC CGG TAC ATC CTC GAC GGC ATC      48
Ser Ser Glu Arg Ile Asp Lys Gln Ile Arg Tyr Ile Leu Asp Gly Ile
1               5                   10                  15

TCG GCG CTG CGG AAG GAG ACG TGC AAC AAG TCC AAC ATG TGC GAG TCG      96
Ser Ala Leu Arg Lys Glu Thr Cys Asn Lys Ser Asn Met Cys Glu Ser
            20                  25                  30

```
TCG  AAG  GAG  GCC  CTC  GCG  GAG  AAC  AAC  CTC  AAC  CTC  CCC  AAG  ATG  GCC      144
Ser  Lys  Glu  Ala  Leu  Ala  Glu  Asn  Asn  Leu  Asn  Leu  Pro  Lys  Met  Ala
          35                       40                      45

GAG  AAG  GAC  GGG  TGC  TTC  CAG  AGC  GGG  TTC  AAC  GAA  GAG  ACC  TGC  CTG      192
Glu  Lys  Asp  Gly  Cys  Phe  Gln  Ser  Gly  Phe  Asn  Glu  Glu  Thr  Cys  Leu
          50                       55                      60

GTC  AAG  ATC  ATC  ACC  GGG  CTG  CTC  GAG  TTC  GAG  GTC  TAC  CTG  GAG  TAC      240
Val  Lys  Ile  Ile  Thr  Gly  Leu  Leu  Glu  Phe  Glu  Val  Tyr  Leu  Glu  Tyr
 65                           70                      75                      80

CTG  CAA  AAC  CGC  TTC  GAG  TCG  AGC  GAG  GAG  CAG  GCG  CGG  GCC  GTG  CAG      288
Leu  Gln  Asn  Arg  Phe  Glu  Ser  Ser  Glu  Glu  Gln  Ala  Arg  Ala  Val  Gln
                    85                       90                          95

ATG  TCG  ACC  AAG  GTC  CTC  ATC  CAG  TTC  TTG  CAG  AAG  AAG  GCG  AAG  AAC      336
Met  Ser  Thr  Lys  Val  Leu  Ile  Gln  Phe  Leu  Gln  Lys  Lys  Ala  Lys  Asn
               100                      105                     110

CTG  GAC  GCG  ATC  ACC  ACG  CCC  GAC  CCC  ACG  ACG  AAC  GCC  TCC  CTG  CTG      384
Leu  Asp  Ala  Ile  Thr  Thr  Pro  Asp  Pro  Thr  Thr  Asn  Ala  Ser  Leu  Leu
               115                      120                     125

ACG  AAG  CTG  CAG  GCC  CAG  AAC  CAG  TGG  CTC  CAG  GAC  ATG  ACC  ACC  CAC      432
Thr  Lys  Leu  Gln  Ala  Gln  Asn  Gln  Trp  Leu  Gln  Asp  Met  Thr  Thr  His
 130                          135                     140

CTG  ATC  CTG  CGG  AGC  TTC  AAG  GAG  TTC  CTC  CAG  TCC  AGC  CTC  CGG  GCC      480
Leu  Ile  Leu  Arg  Ser  Phe  Lys  Glu  Phe  Leu  Gln  Ser  Ser  Leu  Arg  Ala
 145                     150                     155                     160

CTG  CGC  CAG  ATG  TAAGCT                                                          498
Leu  Arg  Gln  Met
```

( 2 ) INFORMATION FOR SEQ ID NO:60:

( i ) SEQUENCE CHARACTERISTICS:
        ( A ) LENGTH: 164 amino acids
        ( B ) TYPE: amino acid
        ( D ) TOPOLOGY: linear ( i i ) MOLECULE TYPE: protein ( x i ) SEQUENCE DESCRIPTION: SEQ ID NO:60:

```
Ser  Ser  Glu  Arg  Ile  Asp  Lys  Gln  Ile  Arg  Tyr  Ile  Leu  Asp  Gly  Ile
 1                    5                       10                      15

Ser  Ala  Leu  Arg  Lys  Glu  Thr  Cys  Asn  Lys  Ser  Asn  Met  Cys  Glu  Ser
               20                       25                      30

Ser  Lys  Glu  Ala  Leu  Ala  Glu  Asn  Asn  Leu  Asn  Leu  Pro  Lys  Met  Ala
          35                       40                      45

Glu  Lys  Asp  Gly  Cys  Phe  Gln  Ser  Gly  Phe  Asn  Glu  Glu  Thr  Cys  Leu
          50                       55                      60

Val  Lys  Ile  Ile  Thr  Gly  Leu  Leu  Glu  Phe  Glu  Val  Tyr  Leu  Glu  Tyr
 65                           70                      75                      80

Leu  Gln  Asn  Arg  Phe  Glu  Ser  Ser  Glu  Glu  Gln  Ala  Arg  Ala  Val  Gln
                    85                       90                          95

Met  Ser  Thr  Lys  Val  Leu  Ile  Gln  Phe  Leu  Gln  Lys  Lys  Ala  Lys  Asn
               100                      105                     110

Leu  Asp  Ala  Ile  Thr  Thr  Pro  Asp  Pro  Thr  Thr  Asn  Ala  Ser  Leu  Leu
               115                      120                     125

Thr  Lys  Leu  Gln  Ala  Gln  Asn  Gln  Trp  Leu  Gln  Asp  Met  Thr  Thr  His
 130                          135                     140

Leu  Ile  Leu  Arg  Ser  Phe  Lys  Glu  Phe  Leu  Gln  Ser  Ser  Leu  Arg  Ala
 145                     150                     155                     160

Leu  Arg  Gln  Met
```

(2) INFORMATION FOR SEQ ID NO:61:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Synthetic DNA oligonucleotide (xi) SEQUENCE DESCRIPTION: SEQ ID NO:61:

```
CCGTCCCCC CCGGCGAGGA CTCCAAGGAC GTCGCCGCCC CCCACCGCCA GCCGCTCACG        60

AGCTCCTAA                                                               69
```

(2) INFORMATION FOR SEQ ID NO:62:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Synthetic DNA oligonucleotide (iv) ANTI-SENSE: YES (xi) SEQUENCE DESCRIPTION: SEQ ID NO:62:

```
AGCTTTAGGA GCTCGTGAGC GGCTGGCGGT GGGGGGCGGC GACGTCCTTG GAGTCCTCGC        60

CGGGGGGGAC CGGTGCA                                                       77
```

(2) INFORMATION FOR SEQ ID NO:63:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO:63:

```
Pro Val Pro Pro Gly Glu Asp Ser Lys Asp Val Ala Ala Pro His Arg
1               5                   10                  15

Gln Pro Leu Thr
            20
```

(2) INFORMATION FOR SEQ ID NO:64:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Synthetic DNA oligonucleotide (xi) SEQUENCE DESCRIPTION: SEQ ID NO:64:

```
TCGACGGCCG CCTCCGGGGC GTCGGCTGCA                                         30
```

(2) INFORMATION FOR SEQ ID NO:65:

(i) SEQUENCE CHARACTERISTICS:
        (A) LENGTH: 22 base pairs
        (B) TYPE: nucleic acid
        (C) STRANDEDNESS: single
        (D) TOPOLOGY: linear ( i i ) MOLECULE TYPE: Other nucleic acid;
 ( A ) DESCRIPTION: Synthetic DNA oligonucleotide ( i v ) ANTI-SENSE: YES ( x i ) SEQUENCE DESCRIPTION: SEQ ID NO:65:

GCCGACGCCC CGGAGGCGGC CG                                                    22

( 2 ) INFORMATION FOR SEQ ID NO:66:

( i ) SEQUENCE CHARACTERISTICS:
  ( A ) LENGTH: 10 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:66:

Ser Thr Ala Ala Ser Gly Ala Ser Ala Ala
  1               5                   10

( 2 ) INFORMATION FOR SEQ ID NO:67:

( i ) SEQUENCE CHARACTERISTICS:
  ( A ) LENGTH: 10 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:67:

Xaa Pro Val Pro Pro Gly Glu Asp Ser Lys
  1               5                   10

( 2 ) INFORMATION FOR SEQ ID NO:68:

( i ) SEQUENCE CHARACTERISTICS:
  ( A ) LENGTH: 10 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:68:

Xaa Xaa Pro Val Pro Pro Gly Glu Asp Ser
  1               5                   10

( 2 ) INFORMATION FOR SEQ ID NO:69:

( i ) SEQUENCE CHARACTERISTICS:
  ( A ) LENGTH: 508 base pairs
  ( B ) TYPE: nucleic acid
  ( C ) STRANDEDNESS: double
  ( D ) TOPOLOGY: linear ( i i ) MOLECULE TYPE: Other nucleic acid;
  ( A ) DESCRIPTION: Synthetic DNA oligonucleotide ( i x ) FEATURE:
  ( A ) NAME/KEY: CDS
  ( B ) LOCATION: 5..502

( x i ) SEQUENCE DESCRIPTION: SEQ ID NO:69:

TGCA GCC CCC CCG CGC CTC ATC TGC GAC AGC CGC GTC CTC GAG CGG TAC            49
     Ala Pro Pro Arg Leu Ile Cys Asp Ser Arg Val Leu Glu Arg Tyr
     1               5                   10                  15

CTG CTC GAA GCC AAG GAG GCG GAG AAT ATC ACG ACG GGG TGC GCC GAG             97
Leu Leu Glu Ala Lys Glu Ala Glu Asn Ile Thr Thr Gly Cys Ala Glu

|  |  |  |  |  |  |  |  |  |  |  |  |  |  |  |  |
|---|---|---|---|---|---|---|---|---|---|---|---|---|---|---|---|
| CAC | TGC | TCC | CTC | AAC | GAG | AAC | ATC | ACC | GTC | CCC | GAC | ACC | AAG | GTC | AAC | 145
| His | Cys | Ser | Leu | Asn | Glu | Asn | Ile | Thr | Val | Pro | Asp | Thr | Lys | Val | Asn |
|  |  | 35 |  |  |  | 40 |  |  |  |  | 45 |  |  |  |  |
| TTC | TAC | GCC | TGG | AAG | CGC | ATG | GAG | GTG | GGC | CAG | CAG | GCG | GTC | GAG | GTC | 193
| Phe | Tyr | Ala | Trp | Lys | Arg | Met | Glu | Val | Gly | Gln | Gln | Ala | Val | Glu | Val |
|  |  | 50 |  |  |  |  | 55 |  |  |  | 60 |  |  |  |  |
| TGG | CAG | GGG | CTC | GCG | CTC | CTC | TCC | GAG | GCG | GTC | CTC | CGC | GGC | CAG | GCC | 241
| Trp | Gln | Gly | Leu | Ala | Leu | Leu | Ser | Glu | Ala | Val | Leu | Arg | Gly | Gln | Ala |
|  | 65 |  |  |  |  | 70 |  |  |  | 75 |  |  |  |  |  |
| CTC | CTG | GTG | AAC | TCG | TCC | CAG | CCG | TGG | GAG | CCG | CTC | CAG | CTG | CAC | GTC | 289
| Leu | Leu | Val | Asn | Ser | Ser | Gln | Pro | Trp | Glu | Pro | Leu | Gln | Leu | His | Val |
| 80 |  |  |  |  | 85 |  |  |  | 90 |  |  |  |  |  | 95 |
| GAC | AAG | GCC | GTC | TCC | GGG | CTC | CGG | TCC | CTG | ACC | ACG | CTG | CTG | CGC | GCC | 337
| Asp | Lys | Ala | Val | Ser | Gly | Leu | Arg | Ser | Leu | Thr | Thr | Leu | Leu | Arg | Ala |
|  |  |  |  | 100 |  |  |  | 105 |  |  |  |  | 110 |  |  |
| CTC | GGT | GCC | CAG | AAG | GAG | GCC | ATC | TCG | CCC | CCG | GAC | GCC | GCC | AGC | GCC | 385
| Leu | Gly | Ala | Gln | Lys | Glu | Ala | Ile | Ser | Pro | Pro | Asp | Ala | Ala | Ser | Ala |
|  |  |  | 115 |  |  |  |  | 120 |  |  |  |  | 125 |  |  |
| GCC | CCG | CTG | CGG | ACG | ATC | ACG | GCG | GAC | ACC | TTC | CGC | AAG | CTG | TTC | CGG | 433
| Ala | Pro | Leu | Arg | Thr | Ile | Thr | Ala | Asp | Thr | Phe | Arg | Lys | Leu | Phe | Arg |
|  |  | 130 |  |  |  |  | 135 |  |  |  |  | 140 |  |  |  |
| GTC | TAC | TCG | AAC | TTC | CTG | CGG | GGG | AAG | CTG | AAG | CTC | TAC | ACC | GGC | GAG | 481
| Val | Tyr | Ser | Asn | Phe | Leu | Arg | Gly | Lys | Leu | Lys | Leu | Tyr | Thr | Gly | Glu |
|  | 145 |  |  |  |  | 150 |  |  |  |  | 155 |  |  |  |  |
| GCC | TGC | CGC | ACG | GGC | GAC | CGG | TAAGCT |  |  |  |  |  |  |  |  | 508
| Ala | Cys | Arg | Thr | Gly | Asp | Arg |  |  |  |  |  |  |  |  |  |
| 160 |  |  |  |  | 165 |  |  |  |  |  |  |  |  |  |  |

( 2 ) INFORMATION FOR SEQ ID NO:70:

( i ) SEQUENCE CHARACTERISTICS:
        ( A ) LENGTH: 166 amino acids
        ( B ) TYPE: amino acid
        ( D ) TOPOLOGY: linear ( i i ) MOLECULE TYPE: protein ( x i ) SEQUENCE DESCRIPTION: SEQ ID NO:70:

| Ala | Pro | Pro | Arg | Leu | Ile | Cys | Asp | Ser | Arg | Val | Leu | Glu | Arg | Tyr | Leu |
|---|---|---|---|---|---|---|---|---|---|---|---|---|---|---|---|
| 1 |  |  |  | 5 |  |  |  |  | 10 |  |  |  |  | 15 |  |
| Leu | Glu | Ala | Lys | Glu | Ala | Glu | Asn | Ile | Thr | Thr | Gly | Cys | Ala | Glu | His |
|  |  |  | 20 |  |  |  |  | 25 |  |  |  |  | 30 |  |  |
| Cys | Ser | Leu | Asn | Glu | Asn | Ile | Thr | Val | Pro | Asp | Thr | Lys | Val | Asn | Phe |
|  |  | 35 |  |  |  |  | 40 |  |  |  |  | 45 |  |  |  |
| Tyr | Ala | Trp | Lys | Arg | Met | Glu | Val | Gly | Gln | Gln | Ala | Val | Glu | Val | Trp |
|  | 50 |  |  |  |  | 55 |  |  |  |  | 60 |  |  |  |  |
| Gln | Gly | Leu | Ala | Leu | Leu | Ser | Glu | Ala | Val | Leu | Arg | Gly | Gln | Ala | Leu |
| 65 |  |  |  |  | 70 |  |  |  |  | 75 |  |  |  |  | 80 |
| Leu | Val | Asn | Ser | Ser | Gln | Pro | Trp | Glu | Pro | Leu | Gln | Leu | His | Val | Asp |
|  |  |  |  | 85 |  |  |  |  | 90 |  |  |  |  | 95 |  |
| Lys | Ala | Val | Ser | Gly | Leu | Arg | Ser | Leu | Thr | Thr | Leu | Leu | Arg | Ala | Leu |
|  |  |  | 100 |  |  |  |  | 105 |  |  |  |  | 110 |  |  |
| Gly | Ala | Gln | Lys | Glu | Ala | Ile | Ser | Pro | Pro | Asp | Ala | Ala | Ser | Ala | Ala |
|  |  | 115 |  |  |  |  | 120 |  |  |  |  | 125 |  |  |  |
| Pro | Leu | Arg | Thr | Ile | Thr | Ala | Asp | Thr | Phe | Arg | Lys | Leu | Phe | Arg | Val |
|  | 130 |  |  |  |  | 135 |  |  |  |  | 140 |  |  |  |  |
| Tyr | Ser | Asn | Phe | Leu | Arg | Gly | Lys | Leu | Lys | Leu | Tyr | Thr | Gly | Glu | Ala |
| 145 |  |  |  |  | 150 |  |  |  |  | 155 |  |  |  |  | 160 |

Cys Arg Thr Gly Asp Arg
165

( 2 ) INFORMATION FOR SEQ ID NO:71:

( i ) SEQUENCE CHARACTERISTICS:
        ( A ) LENGTH: 39 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:71:

Met Arg Ile Lys Arg Thr Ser Asn Arg Ser Asn Ala Ala Arg Arg Val
1               5                   10                  15

Arg Thr Thr Ala Val Leu Ala Gly Leu Ala Ala Val Ala Ala Leu Ala
            20              25                  30

Val Pro Thr Pro Ala Ala Ala
            35

( 2 ) INFORMATION FOR SEQ ID NO:72:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( x i ) SEQUENCE DESCRIPTION: SEQ ID NO:72:

CGCGTCCGCA CCACCGCCGT ACTCGCGGGC CTGGCGGCCG TCGCGGCGCT AGCCGTTCCC    60

ACGCCCGCCG CTGCA    75

( 2 ) INFORMATION FOR SEQ ID NO:73:

( i ) SEQUENCE CHARACTERISTICS:
        ( A ) LENGTH: 67 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( i v ) ANTI-SENSE: YES ( x i ) SEQUENCE DESCRIPTION: SEQ ID NO:73:

GCGGCGGGCG TGGGAACGGC TAGCGCCGCG ACGGCCGCCA GGCCCGCGAG TACGGCGGTG    60

GTGCGGA    67

( 2 ) INFORMATION FOR SEQ ID NO:74:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:74:

Arg Val Arg Thr Thr Ala Val Leu Ala Gly Leu Ala Ala Val Ala Ala
1               5                   10                  15

Leu Ala Val Pro Thr Pro Ala Ala Ala
            20                  25

( 2 ) INFORMATION FOR SEQ ID NO:75:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:75:

```
Xaa  Pro  Pro  Xaa  Leu  Ile  Xaa  Asp  Ser  Arg
 1              5                         10
```

( 2 ) INFORMATION FOR SEQ ID NO:76:

( i ) SEQUENCE CHARACTERISTICS:
        ( A ) LENGTH: 501 base pairs
        ( B ) TYPE: nucleic acid
        ( C ) STRANDEDNESS: double
        ( D ) TOPOLOGY: linear ( i i ) MOLECULE TYPE: Other nucleic acid;
        ( A ) DESCRIPTION: Synthetic DNA oligonucleotide ( i x ) FEATURE:
        ( A ) NAME/KEY: CDS
        ( B ) LOCATION: 5..496

( x i ) SEQUENCE DESCRIPTION: SEQ ID NO:76:

```
TGCA GAG GGG ATC TGC CGC AAC CGG GTC ACG AAC AAC GTG AAG GAC GTG         49
     Glu Gly Ile Cys Arg Asn Arg Val Thr Asn Asn Val Lys Asp Val
      1           5                  10                  15

ACG AAG CTC GTC GCG AAC CTG CCG AAG GAC TAC ATG ATC ACG CTC AAG          97
Thr Lys Leu Val Ala Asn Leu Pro Lys Asp Tyr Met Ile Thr Leu Lys
             20                  25                  30

TAC GTC CCC GGC ATG GAC GTG CTC CCG TCC CAC TGC TGG ATC AGC GAG         145
Tyr Val Pro Gly Met Asp Val Leu Pro Ser His Cys Trp Ile Ser Glu
                 35                  40                  45

ATG GTG GTG CAG CTG AGC GAC AGC CTG ACG GAC CTC CTG GAC AAG TTC         193
Met Val Val Gln Leu Ser Asp Ser Leu Thr Asp Leu Leu Asp Lys Phe
                     50                  55                  60

TCG AAC ATC TCC GAG GGC CTC TCC AAC TAC TCC ATC ATC GAC AAG CTG         241
Ser Asn Ile Ser Glu Gly Leu Ser Asn Tyr Ser Ile Ile Asp Lys Leu
             65                  70                  75

GTC AAC ATC GTG GAC GAC CTG GTG GAG TGC GTC AAG GAG AAC TCG AGC         289
Val Asn Ile Val Asp Asp Leu Val Glu Cys Val Lys Glu Asn Ser Ser
 80                  85                  90                  95

AAG GAC CTC AAG AAG AGC TTC AAG TCC CCC GAG CCC CGC CTG TTC ACG         337
Lys Asp Leu Lys Lys Ser Phe Lys Ser Pro Glu Pro Arg Leu Phe Thr
                    100                 105                 110

CCC GAG GAG TTC TTC CGG ATC TTC AAC CGC TCG ATC GAC GCC TTC AAG         385
Pro Glu Glu Phe Phe Arg Ile Phe Asn Arg Ser Ile Asp Ala Phe Lys
                115                 120                 125

GAC TTC GTC GTG GCG TCC GAG ACC TCC GAC TGC GTG GTC AGC TCG ACC         433
Asp Phe Val Val Ala Ser Glu Thr Ser Asp Cys Val Val Ser Ser Thr
                    130                 135                 140

CTC AGC CCG GAG AAG GAC TCG CGG GTG TCG GTC ACC AAG CCG TTC ATG         481
Leu Ser Pro Glu Lys Asp Ser Arg Val Ser Val Thr Lys Pro Phe Met
        145                 150                 155

CTG CCC CCC GTC GCC AAGCT                                                501
Leu Pro Pro Val Ala
160
```

( 2 ) INFORMATION FOR SEQ ID NO:77:

( i ) SEQUENCE CHARACTERISTICS:
    ( A ) LENGTH: 164 amino acids
    ( B ) TYPE: amino acid
    ( D ) TOPOLOGY: linear ( i i ) MOLECULE TYPE: protein ( x i ) SEQUENCE DESCRIPTION: SEQ ID NO:77:

```
Glu Gly Ile Cys Arg Asn Arg Val Thr Asn Asn Val Lys Asp Val Thr
 1               5                  10                  15
Lys Leu Val Ala Asn Leu Pro Lys Asp Tyr Met Ile Thr Leu Lys Tyr
                20                  25                  30
Val Pro Gly Met Asp Val Leu Pro Ser His Cys Trp Ile Ser Glu Met
            35                  40                  45
Val Val Gln Leu Ser Asp Ser Leu Thr Asp Leu Leu Asp Lys Phe Ser
    50                  55                  60
Asn Ile Ser Glu Gly Leu Ser Asn Tyr Ser Ile Ile Asp Lys Leu Val
65                  70                  75                  80
Asn Ile Val Asp Asp Leu Val Glu Cys Val Lys Glu Asn Ser Ser Lys
                85                  90                  95
Asp Leu Lys Lys Ser Phe Lys Ser Pro Glu Pro Arg Leu Phe Thr Pro
            100                 105                 110
Glu Glu Phe Phe Arg Ile Phe Asn Arg Ser Ile Asp Ala Phe Lys Asp
        115                 120                 125
Phe Val Val Ala Ser Glu Thr Ser Asp Cys Val Val Ser Ser Thr Leu
    130                 135                 140
Ser Pro Glu Lys Asp Ser Arg Val Ser Val Thr Lys Pro Phe Met Leu
145                 150                 155                 160
Pro Pro Val Ala
```

( 2 ) INFORMATION FOR SEQ ID NO:78:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( x i ) SEQUENCE DESCRIPTION: SEQ ID NO:78:

```
CGCGTCCGGA TCGTCGTTGC AGCCATCGCC GTTTCCCTGA CCACGGTCTC GATTACGGCC    60
AGCGCGTCTG CA                                                       72
```

( 2 ) INFORMATION FOR SEQ ID NO:79:

( i ) SEQUENCE CHARACTERISTICS:
        ( A ) LENGTH: 64 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( i v ) ANTI-SENSE: YES ( x i ) SEQUENCE DESCRIPTION: SEQ ID NO:79:

```
GACGCGCTGG CCGTAATCGA GACCGTGGTC AGGGAAACGG CGATGGCTGC AACGACGATC    60
CGGA                                                                64
```

(2) INFORMATION FOR SEQ ID NO:80:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (xi) SEQUENCE DESCRIPTION: SEQ ID NO:80:

```
Arg Val Arg Ile Val Val Ala Ala Ile Ala Val Ser Leu Thr Thr Val
1               5                   10                  15
Ser Ile Thr Ala Ser Ala Ser Ala
            20
```

(2) INFORMATION FOR SEQ ID NO:81:

(i) SEQUENCE CHARACTERISTICS:
        (A) LENGTH: 38 amino acids
        (B) TYPE: amino acid
        (D) TOPOLOGY: linear (ii) MOLECULE TYPE: peptide (xi) SEQUENCE DESCRIPTION: SEQ ID NO:81:

```
Met Arg Ile Lys Arg Thr Ser Asn Arg Ser Asn Ala Ala Arg Arg Val
1               5                   10                  15
Arg Ile Val Val Ala Ala Ile Ala Val Ser Leu Thr Thr Val Ser Ile
            20                  25                  30
Thr Ala Ser Ala Ser Ala
            35
```

(2) INFORMATION FOR SEQ ID NO:82:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:82:

```
Xaa Gly Ile Xaa Xaa Asn Xaa Val Thr Asn
1               5                   10
```

(2) INFORMATION FOR SEQ ID NO:83:

(i) SEQUENCE CHARACTERISTICS:
        (A) LENGTH: 467 base pairs
        (B) TYPE: nucleic acid
        (C) STRANDEDNESS: double
        (D) TOPOLOGY: linear (ii) MOLECULE TYPE: Other nucleic acid;
        (A) DESCRIPTION: Synthetic DNA oligonucleotide (ix) FEATURE:
        (A) NAME/KEY: CDS
        (B) LOCATION: 5..460

(xi) SEQUENCE DESCRIPTION: SEQ ID NO:83:

```
TGCA GAC TGC GAC ATC GAG GGG AAG GAC GGC AAG CAG TAC GAG TCG GTG         49
     Asp Cys Asp Ile Glu Gly Lys Asp Gly Lys Gln Tyr Glu Ser Val
     1               5                   10                  15
CTG ATG GTG TCC ATC GAC CAG TTG CTG GAC TCG ATG AAG GAG ATC GGC          97
Leu Met Val Ser Ile Asp Gln Leu Leu Asp Ser Met Lys Glu Ile Gly
                20                  25                  30
```

```
TCC AAC TGC CTC AAC AAC GAG TTC AAC TTC TTC AAG CGC CAC ATC TGC    145
Ser Asn Cys Leu Asn Asn Glu Phe Asn Phe Phe Lys Arg His Ile Cys
        35                  40                  45

GAC GCC AAC AAG GAG GGA ATG TTC CTG TTC CGG GCC GCG CGC AAG CTG    193
Asp Ala Asn Lys Glu Gly Met Phe Leu Phe Arg Ala Ala Arg Lys Leu
        50                  55                  60

CGC CAG TTC CTC AAG ATG AAT TCC ACC GGG GAC TTC GAC CTC CAC CTG    241
Arg Gln Phe Leu Lys Met Asn Ser Thr Gly Asp Phe Asp Leu His Leu
        65                  70                  75

CTC AAG GTC TCG GAG GGC ACG ACC ATC CTG CTG AAC TGC ACG GGC CAG    289
Leu Lys Val Ser Glu Gly Thr Thr Ile Leu Leu Asn Cys Thr Gly Gln
80                  85                  90                  95

GTC AAG GGA CGG AAG CCC GCC GCC CTC GGG GAG GCC CAG CCG ACG AAG    337
Val Lys Gly Arg Lys Pro Ala Ala Leu Gly Glu Ala Gln Pro Thr Lys
            100                 105                 110

AGC TTG GAG GAA AAC AAG TCC CTG AAG GAG CAG AAG AAG CTC AAC GAC    385
Ser Leu Glu Glu Asn Lys Ser Leu Lys Glu Gln Lys Lys Leu Asn Asp
            115                 120                 125

CTG TGC TTC CTG AAG CGG TTG CTC CAG GAG ATC AAG ACG TGC TGG AAC    433
Leu Cys Phe Leu Lys Arg Leu Leu Gln Glu Ile Lys Thr Cys Trp Asn
            130                 135                 140

AAG ATC CTC ATG GGC ACC AAG GAA CAC TGAAGCT                        467
Lys Ile Leu Met Gly Thr Lys Glu His
            145                 150
```

( 2 ) INFORMATION FOR SEQ ID NO:84:

( i ) SEQUENCE CHARACTERISTICS:
    ( A ) LENGTH: 152 amino acids
    ( B ) TYPE: amino acid
    ( D ) TOPOLOGY: linear ( i i ) MOLECULE TYPE: protein ( x i ) SEQUENCE DESCRIPTION: SEQ ID NO:84:

```
Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Phe Asn Phe Phe Lys Arg His Ile Cys Asp
        35                  40                  45

Ala Asn Lys Glu Gly Met Phe Leu Phe Arg Ala Ala Arg Lys Leu Arg
        50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
            85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
            115                 120                 125

Cys Phe Leu Lys Arg Leu Leu Gln Glu Ile Lys Thr Cys Trp Asn Lys
        130                 135                 140

Ile Leu Met Gly Thr Lys Glu His
145                 150
```

( 2 ) INFORMATION FOR SEQ ID NO:85:

( i ) SEQUENCE CHARACTERISTICS:
    ( A ) LENGTH: 478 base pairs (B) TYPE: nucleic acid
(C) STRANDEDNESS: double
(D) TOPOLOGY: linear (ii) MOLECULE TYPE: Other nucleic acid;
(A) DESCRIPTION: Synthetic DNA oligonucleotide (ix) FEATURE:
(A) NAME/KEY: CDS
(B) LOCATION: 5..475

(xi) SEQUENCE DESCRIPTION: SEQ ID NO:85:

| TGCA | GTG | CGG | TCC | TCG | TCC | CGC | ACC | CCG | TCC | GAC | AAG | CCC | GTG | GCG | CAC | 49 |
|---|---|---|---|---|---|---|---|---|---|---|---|---|---|---|---|---|
| | Val | Arg | Ser | Ser | Ser | Arg | Thr | Pro | Ser | Asp | Lys | Pro | Val | Ala | His | |
| | 1 | | | | 5 | | | | | 10 | | | | | 15 | |

| GTG | GTG | GCG | AAC | CCC | CAG | GCG | GAG | GGC | CAG | CTC | CAG | TGG | CTG | AAC | CGG | 97 |
|---|---|---|---|---|---|---|---|---|---|---|---|---|---|---|---|---|
| Val | Val | Ala | Asn | Pro | Gln | Ala | Glu | Gly | Gln | Leu | Gln | Trp | Leu | Asn | Arg | |
| | | | 20 | | | | | 25 | | | | | | 30 | | |

| CGC | GCG | AAC | GCG | CTG | CTC | GCC | AAC | GGC | GTC | GAG | CTC | CGC | GAC | AAC | CAG | 145 |
|---|---|---|---|---|---|---|---|---|---|---|---|---|---|---|---|---|
| Arg | Ala | Asn | Ala | Leu | Leu | Ala | Asn | Gly | Val | Glu | Leu | Arg | Asp | Asn | Gln | |
| | | | 35 | | | | | 40 | | | | | 45 | | | |

| CTC | GTG | GTC | CCG | AGC | GAG | GGC | CTG | TAC | CTC | ATC | TAC | TCG | CAG | GTG | CTG | 193 |
|---|---|---|---|---|---|---|---|---|---|---|---|---|---|---|---|---|
| Leu | Val | Val | Pro | Ser | Glu | Gly | Leu | Tyr | Leu | Ile | Tyr | Ser | Gln | Val | Leu | |
| | | 50 | | | | | 55 | | | | | 60 | | | | |

| TTC | AAG | GGC | CAG | GGG | TGC | CCG | TCG | ACC | CAC | GTC | CTG | CTG | ACG | CAC | ACC | 241 |
|---|---|---|---|---|---|---|---|---|---|---|---|---|---|---|---|---|
| Phe | Lys | Gly | Gln | Gly | Cys | Pro | Ser | Thr | His | Val | Leu | Leu | Thr | His | Thr | |
| | 65 | | | | | 70 | | | | | 75 | | | | | |

| ATC | TCG | CGC | ATC | GCG | GTG | TCC | TAC | CAG | ACC | AAG | GTG | AAC | CTC | CTG | TCC | 289 |
|---|---|---|---|---|---|---|---|---|---|---|---|---|---|---|---|---|
| Ile | Ser | Arg | Ile | Ala | Val | Ser | Tyr | Gln | Thr | Lys | Val | Asn | Leu | Leu | Ser | |
| 80 | | | | | 85 | | | | | 90 | | | | | 95 | |

| GCC | ATC | AAG | TCC | CCG | TGC | CAG | CGG | GAG | ACG | CCC | GAG | GGC | GCG | GAG | GCC | 337 |
|---|---|---|---|---|---|---|---|---|---|---|---|---|---|---|---|---|
| Ala | Ile | Lys | Ser | Pro | Cys | Gln | Arg | Glu | Thr | Pro | Glu | Gly | Ala | Glu | Ala | |
| | | | | 100 | | | | | 105 | | | | | 110 | | |

| AAG | CCC | TGG | TAC | GAG | CCG | ATC | TAC | CTG | GGC | GGC | GTG | TTC | CAG | CTC | GAG | 385 |
|---|---|---|---|---|---|---|---|---|---|---|---|---|---|---|---|---|
| Lys | Pro | Trp | Tyr | Glu | Pro | Ile | Tyr | Leu | Gly | Gly | Val | Phe | Gln | Leu | Glu | |
| | | | 115 | | | | | 120 | | | | | 125 | | | |

| AAG | GGG | GAC | CGG | CTG | AGC | GCC | GAG | ATC | AAC | CGC | CCC | GAC | TAC | CTC | GAC | 433 |
|---|---|---|---|---|---|---|---|---|---|---|---|---|---|---|---|---|
| Lys | Gly | Asp | Arg | Leu | Ser | Ala | Glu | Ile | Asn | Arg | Pro | Asp | Tyr | Leu | Asp | |
| | | | 130 | | | | | 135 | | | | | 140 | | | |

| TTC | GCC | GAG | TCC | GGG | CAG | GTG | TAC | TTC | GGC | ATC | ATC | GCG | CTC | | | 475 |
|---|---|---|---|---|---|---|---|---|---|---|---|---|---|---|---|---|
| Phe | Ala | Glu | Ser | Gly | Gln | Val | Tyr | Phe | Gly | Ile | Ile | Ala | Leu | | | |
| | 145 | | | | | 150 | | | | | 155 | | | | | |

TAG                                                                                           478

(2) INFORMATION FOR SEQ ID NO:86:

(i) SEQUENCE CHARACTERISTICS:
(A) LENGTH: 157 amino acids
(B) TYPE: amino acid
(D) TOPOLOGY: linear (ii) MOLECULE TYPE: protein (xi) SEQUENCE DESCRIPTION: SEQ ID NO:86:

| Val | Arg | Ser | Ser | Ser | Arg | Thr | Pro | Ser | Asp | Lys | Pro | Val | Ala | His | Val |
|---|---|---|---|---|---|---|---|---|---|---|---|---|---|---|---|
| 1 | | | | 5 | | | | | 10 | | | | | 15 | |

| Val | Ala | Asn | Pro | Gln | Ala | Glu | Gly | Gln | Leu | Gln | Trp | Leu | Asn | Arg | Arg |
|---|---|---|---|---|---|---|---|---|---|---|---|---|---|---|---|
| | | | 20 | | | | | 25 | | | | | 30 | | |

| Ala | Asn | Ala | Leu | Leu | Ala | Asn | Gly | Val | Glu | Leu | Arg | Asp | Asn | Gln | Leu |
|---|---|---|---|---|---|---|---|---|---|---|---|---|---|---|---|
| | | 35 | | | | | 40 | | | | | 45 | | | |

| Val | Val | Pro | Ser | Glu | Gly | Leu | Tyr | Leu | Ile | Tyr | Ser | Gln | Val | Leu | Phe |
|---|---|---|---|---|---|---|---|---|---|---|---|---|---|---|---|
| | 50 | | | | | 55 | | | | | 60 | | | | |

```
Lys Gly Gln Gly Cys Pro Ser Thr His Val Leu Thr His Thr Ile
 65              70                  75                  80

Ser Arg Ile Ala Val Ser Tyr Gln Thr Lys Val Asn Leu Leu Ser Ala
                 85                  90                  95

Ile Lys Ser Pro Cys Gln Arg Glu Thr Pro Glu Gly Ala Glu Ala Lys
                100             105                 110

Pro Trp Tyr Glu Pro Ile Tyr Leu Gly Gly Val Phe Gln Leu Glu Lys
            115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155
```

(2) INFORMATION FOR SEQ ID NO:87:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:87:

```
Ser Arg Thr Pro Ser Asp Lys Pro Val Ala
 1               5                   10
```

(2) INFORMATION FOR SEQ ID NO:88:

(i) SEQUENCE CHARACTERISTICS:
        (A) LENGTH: 412 base pairs
        (B) TYPE: nucleic acid
        (C) STRANDEDNESS: double
        (D) TOPOLOGY: linear (ii) MOLECULE TYPE: Other nucleic acid;
        (A) DESCRIPTION: Synthetic DNA oligonucleotide (ix) FEATURE:
        (A) NAME/KEY: CDS
        (B) LOCATION: 5..403

(xi) SEQUENCE DESCRIPTION: SEQ ID NO:88:

```
TGCA GCC CCG ACG TCC TCG TCG ACC AAG AAG ACC CAG CTC CAG CTC GAA    49
     Ala Pro Thr Ser Ser Ser Thr Lys Lys Thr Gln Leu Gln Leu Glu
      1               5                  10                  15

CAC CTG CTG CTC GAC CTC CAG ATG ATC CTG AAC GGG ATC AAC AAC TAC    97
His Leu Leu Leu Asp Leu Gln Met Ile Leu Asn Gly Ile Asn Asn Tyr
                 20                  25                  30

AAG AAC CCG AAG CTC ACC CGC ATG CTG ACG TTC AAG TTC TAC ATG CCG    145
Lys Asn Pro Lys Leu Thr Arg Met Leu Thr Phe Lys Phe Tyr Met Pro
             35                  40                  45

AAG AAG GCC ACC GAG CTG AAG CAC CTC CAG TGC CTG GAG GAG GAG CTC    193
Lys Lys Ala Thr Glu Leu Lys His Leu Gln Cys Leu Glu Glu Glu Leu
         50                  55                  60

AAG CCG CTC GAG GAG GTC CTG AAC CTC GCG CAG AGC AAG AAC TTC CAC    241
Lys Pro Leu Glu Glu Val Leu Asn Leu Ala Gln Ser Lys Asn Phe His
     65                  70                  75

CTG CGC CCC CGG GAC CTG ATC TCC AAC ATC AAC GTG ATC GTC CTG GAA    289
Leu Arg Pro Arg Asp Leu Ile Ser Asn Ile Asn Val Ile Val Leu Glu
 80                  85                  90                  95

CTG AAG GGG TCG GAG ACC ACC TTC ATG TGC GAG TAC GCC GAC GAG ACC    337
Leu Lys Gly Ser Glu Thr Thr Phe Met Cys Glu Tyr Ala Asp Glu Thr
                100                 105                 110
```

```
GCC ACC ATC GTC GAA TTC CTC AAC CGG TGG ATC ACC TTC TGC CAG AGC        385
Ala Thr Ile Val Glu Phe Leu Asn Arg Trp Ile Thr Phe Cys Gln Ser
            115                 120                 125

ATC ATC AGC ACC CTC ACC TAGGAAGCT                                      412
Ile Ile Ser Thr Leu Thr
        130
```

(2) INFORMATION FOR SEQ ID NO:89:

(i) SEQUENCE CHARACTERISTICS:
        (A) LENGTH: 133 amino acids
        (B) TYPE: amino acid
        (D) TOPOLOGY: linear (ii) MOLECULE TYPE: protein (xi) SEQUENCE DESCRIPTION: SEQ ID NO:89:

```
Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr
        130
```

(2) INFORMATION FOR SEQ ID NO:90:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:90:

```
Ala Pro Thr Ser Ser Ser Thr Lys Lys Thr
 1               5                  10
```

(2) INFORMATION FOR SEQ ID NO:91:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Synthetic DNA oligonucleotide (xi) SEQUENCE DESCRIPTION: SEQ ID NO:91:

```
CTAGCAAGCT TG                                                           12
```